United States Patent
Pogue-Geile et al.

(10) Patent No.: US 10,166,210 B2
(45) Date of Patent: Jan. 1, 2019

(54) METHODS OF SUBTYPING CRC AND THEIR ASSOCIATION WITH TREATMENT OF COLON CANCER PATIENTS WITH OXALIPLATIN

(71) Applicant: NSABP Foundation, Inc., Pittsburgh, PA (US)

(72) Inventors: Katherine Lea Pogue-Geile, Pittsburgh, PA (US); Nan Song, Pittsburgh, PA (US); Soonmyung Paik, Pittsburgh, PA (US)

(73) Assignee: NSABP Foundation, Inc., Pittsburgh, PA (US)

( * ) Notice: Subject to any disclaimer, the term of this patent is extended or adjusted under 35 U.S.C. 154(b) by 233 days.

(21) Appl. No.: 14/738,757

(22) Filed: Jun. 12, 2015

(65) Prior Publication Data
US 2015/0366835 A1  Dec. 24, 2015

Related U.S. Application Data

(60) Provisional application No. 62/011,571, filed on Jun. 12, 2014.

(51) Int. Cl.
*C12Q 1/68* (2018.01)
*A61K 31/282* (2006.01)
*C12Q 1/6886* (2018.01)

(52) U.S. Cl.
CPC .......... *A61K 31/282* (2013.01); *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

PUBLICATIONS

Andre, T., C. Boni, et al. (2009). "Improved overall survival with oxaliplatin, fluorouracil, and leucovorin as adjuvant treatment in stage II or III colon cancer in the MOSAIC trial." J Clin Oncol 27(19): 3109-3116.

De Sousa, E. M. F., X. Wang, et al. (2013). "Poor-prognosis colon cancer is defined by a molecularly distinct subtype and develops from serrated precursor lesions." Nat Med 19(5): 614-618.

Isella, C., A. Terrasi, et al. (2015). "Stromal contribution to the colorectal cancer transcriptome." Nat Genet 47(4): 312-319.

Kuebler, J. P., H. S. Wieand, et al. (2007). "Oxaliplatin combined with weekly bolus fluorouracil and leucovorin as surgical adjuvant chemotherapy for stage II and III colon cancer: results from NSABP C-07." J Clin Oncol 25(16): 2198-2204.

Marisa, L., A. de Reynies, et al. (2013). "Gene expression classification of colon cancer into molecular subtypes: characterization, validation, and prognostic value." PLoS Med 10(5): e1001453.

Sadanandam, A., C. A. Lyssiotis, et al. (2013). "A colorectal cancer classification system that associates cellular phenotype and responses to therapy." Nat Med 19(5): 619-625.

Tournigand, C., T. Andre, et al. (2012). "Adjuvant therapy with fluorouracil and oxaliplatin in stage II and elderly patients (between ages 70 and 75 years) with colon cancer: subgroup analyses of the Multicenter International Study of Oxaliplatin, Fluorouracil, and Leucovorin in the Adjuvant Treatment of Colon Cancer trial." J Clin Oncol 30(27): 3353-3360.

*Primary Examiner* — Jehanne S Sitton
(74) *Attorney, Agent, or Firm* — Vinson & Elkins LLP

(57) ABSTRACT

A gene expression signature identifies stage II colon cancer patients who will receive benefit from oxaliplatin. Oxaliplatin has been shown to lengthen the survival of colon cancer patients, when it is combined with 5-fluorouracil plus leucovorin (FULV) in NSABP clinical trial C-07. Gene expression signatures are used first to classify tumors with regard to their respective subtypes, enterocyte, TA, goblet, inflammatory and stem-like and detection of expression of the enterocyte subtype directs treatment of the patient with oxaliplatin.

6 Claims, 5 Drawing Sheets

METHODS OF SUBTYPING CRC AND THEIR ASSOCIATION WITH TREATMENT OF COLON CANCER PATIENTS WITH OXALIPLATIN

CROSS-REFERENCE TO RELATED APPLICATION

This application claims benefit of priority to U.S. provisional application No. 62/011,571 filed Jun. 12, 2014, the entire contents of winch are incorporated herein by reference for all purposes.

BACKGROUND

Clinical trials MOSAIC (Andre, Boni et al, 2009)[1] (Multicenter International Study of Oxaliplatin, Fluorouracil, and Leueovorin trial) and C-07 (Kuebler, Wieand et al. 2007)[2] showed that oxaliplatin added to fluorouracil (FU) and leucovorin (LV) significantly improved disease free survival (DFS) and established oxaliplatin as part of the standard of care for the adjuvant treatment of early-stage colon cancer. In the C-07 trial, 2,409 patients diagnosed with stage II and III colon adenocarcinoma who had undergone potentially curative surgical resection with no evidence of residual malignant disease were randomly assigned to receive either FULV (FU 500 mg/m2 by intravenous [IV] bolus weekly for 6 weeks; leucovorin 500 mg/m2 IV weekly for 0 weeks of each 8-week cycle for three cycles) or FLOX (FULV plus oxaliplatin 85 mg/m2 IV on days 1, 15, and 29 of each cycle). Based on the 2011 analysis with median follow-up of 8 years, FLOX demonstrated superior DFS (HR; 0.82; P=002)(Kuebler, Wieand et at 2007)[2]. Current NCCN guidelines recommend that all stage III patients, and high risk stage II patients be treated with oxaliplatin. High risk stage II includes patients with perforation, or obstruction or rumors with lymphovascular or perineural invasion, T4 lesions, less than 12 Lymph nodes examined, or grade 3-4 lesions. However, recent analysis of MOSAIC analysis found no statistically significant benefit for either all stage II or high risk stage II patients (Tournigand, Andre et al. 2012)[3]. The use of oxatiplatin in all early stage colon cancer patients remains controversial not only because it is uncertain which patients actually receive benefit but also because of the toxic side effects associated with oxaliplatin (Cersosimo 2005)[4]. Thus, stratifying patients with regard to their oxaliplatin benefit is of significant clinical interest.

Recently, several studies (De Sousa, Wang et al. 2013; Marisa, de Reynies et al. 2013; Sadanandam, Lyssiotis et al. 2013) have used unsupervised clustering methods to develop genomic signatures to classify colorectal cancer to different intrinsic subtypes and showed that each subtype has distinct molecular features, clinical significance and prognosis. These groups identified either 3 or 5 intrinsic subtypes with the CCS3, Stem-Like as the poorest prognostic group. The different number of clusters in these publications is not surprising given that different methods and different training, datasets were used. Sadanandam et al's (Sadanandam, Lyssiotis et at 2013)[9] five subtypes were correlated, to gene expression patterns of the different cell types located within the normal colonic crypts. De Sousa et al also demonstrated that most of the published gene expression based prognostic assays identify essentially the same group of tumors (mostly stem-like or CCS3 subtypes) as those associated with high risk of relapse. Given that it is now well established that breast cancer subtypes differ regarding their prognosis and their response to treatment, it was reasonable to hypothesize that the clinical behavior of the different colon subtypes may also differ with respect to prognosis and importantly with response to treatment. However, it was not possible to test treatment response in these published studies because the patient cohorts were treated with a variety of agents and were not part of a randomized clinical trial designed to test a particular agent. In contrast the gene expression data which was profiled on archived tumor blocks from NSABP clinical trial C-07 represented an ideal experimental cohort to test whether colon cancer subtypes could be used to predict oxidiplatin benefit. Before the publication of these colon cancer subtypes we had completed the gene expression profiling of 1846 patients from C-07 using our custom nCounter code set using nCounter assays from Nanostring Technologies.

SUMMARY

The initial study described here provides a gene expression signature which identifies stage II and III colon cancer patients who will receive benefit from oxaliplatin. Oxaliplatin has been shown to lengthen the survival of colon cancer patients, when it is combined with 5fluorouracil plus leucovorin (FULV) in NSABP clinical trial C-07. However, mounting evidence suggest that not all early stage colon cancer patients benefit from oxaliplatin treatment and the toxicities associated with oxaliplatin highlights the importance of identifying patients who will actually receive benefit from oxaliplatin treatment. We have used gene expression signatures to first classify tumors in C-07 with regard to their respective subtypes, enterocyte, TA, goblet, inflammatory and stem-like and shown that only the enterocyte subtype received benefit from oxaliplatin. Comparing the benefit in the enterocyte subtype to a second group consisting of all four other subtypes, (Goblet-like, Inflammatory, Stem-like and TA) as a non-benefit group, showed a significant treatment-group interaction (p=0.012). In a second step we showed that the stem-like subtype can be further sub-typed into patients who do and do not receive benefit from oxaliplatin. Identification of this sub-subtype which received benefit from oxaliplatin is also of clinical interest in that the stem-like subtype has a very poor prognosis.

We have profiled 296 genes in 1840 patients from NSABP clinical trial C-07 using a custom nCounter code set using the nCounter Assay system from Nanostring Technologies (Seattle Wash.). Genes selected for inclusion on our custom nCounter code set were a result of our own gene expression analysis of the C-07 discovery cohort or other published studies. Gene expression profiling was conducted on tumor blocks from patients with follow-up information and proper consent. Samples within C-07 were split into non-overlapping discovery (N=848) and validation cohorts (N=992). The current description involves only the use of the discovery cohort. Clinical data and nCounter data for the discovery dataset were merged and anonyinized by the honest broker at the University of Pittsburgh as defined by standard operations under IRB approval of the NSABP Biospecimen Bank and Biostatistics Center.

We have developed a predictive algorithm to classify tumors into oxaliplatin benefit or no benefit group using discovery cohort of 848 patients without access to the data from the remaining 992 patients (validation cohort). The nCounter genes used for this analysis are 72 genes included in both our custom nCounter code set (N=296) and in the intrinsic subtype signature described by Sadanandam et al. (Sadanandam, Lyssiotis et al. 2013)

The current disclosure can be described therefore as a method for treating colon cancer in a patient in need thereof said method comprising obtaining a tumor tissue sample from said patient determining a gene expression signature of said sample identifying a tumor tissue subtype from said gene expression signature; and administering oxaliplatin when the identified tumor tissue subtype is an oxaliplatin responsive subtype. As used herein subtype can refer to one of five colon cancer subtypes, enterocyte, TA, goblet, inflammatory and stem-like, and sub-subtype can refer to a division within one of the 5 subtypes that is more enterocyte-like or that is more responsive to oxaliplatin, for example, than other genes within the subtype.

The methods can be further described therefore as determining a gene expression signature by steps including contacting a genetic sample from the tumor tissue sample with a plurality of specific genetic sequence binding targets and measuring the amount of genetic material expressed by the tumor tissue for a panel of selected genes, wherein the panel of genes are selected from those listed in Table 5. A gene binding target can be a polynucleotide, a protein, a peptide or a peptide nucleic acid, and as such can be synthesized based on a complementary sequence or on a synthetic molecule designed to specifically bind to the RNA. The sample or the target can be affixed to a solid surface such as a planar surface, contained in or affixed to a bead or contained in an oil droplet, for example, or in other forms known in the art such as but not limited to next-generation sequencing technologies such as RNA-Seq or whole transcriptome sequencing.

In certain preferred embodiments the genetic sample comprises degraded or intact RNA and can be mRNA or total RNA or whole tissue lysates from selected genes from Table 5. In certain embodiments the panel of genes for determination of a gene signature are selected by a process that includes Weighted Gene Correlation Network Analysis (WGCNA), to identify members of oxaliplatin responsive gene modules.

Disclosed methods of treatment include administration of oxaliplatin is administered in combination with 5-fluorouracil plus leucovorin (FULV), and can include administration to a stage II or stage III colon cancer patient. The tumor sample can be subtype enterocyte or TA or a sub-subtype of enterocyte or TA. In certain embodiments cancer tumor sample is subtype stem-like or a sub-subtype of stem-like.

The disclosure can also be described in certain embodiments as method for treating colon cancer in as patient in need thereof said method comprising, obtaining a tumor tissue sample from said patient; isolating RNA from the tumor tissue sample; contacting the RNA sample with a plurality of sequence specific probes effective to determine levels of expression or a panel of selected genes in the tumor sample to obtain a gene signature identifying a colon cancer subtype or sub-subtype tumor subtype based on the gene signature; and administering oxaliplatin or causing oxaliplatin to be administered to said patient when the cancer subtype or sub-subtype is an oxaliplatin responsive subtype or sub-subtype. Gene specific probes can include complementary nucleic acid sequences or other probes that do not necessarily bind to a site within the gene such as those used for Next-generation sequencing technologies which quantitate RNA by sequencing RNA molecules directly, for example.

The method can include utilizing a panel of selected genes are selected from the genes listed in Table 5. The methods can further include administering oxaliplatin or causing oxaliplatin to be is administered in combination with 5-fluorouracil plus leucovorin (FULV) to a stage II or stage III colon cancer patient, were the patient's tumor tissue is determined to be subtype enterocyte or TA or a sub-subtype of enterocyte or TA, or subtype stem-like or a sub-subtype of stem-like.

BRIEF DESCRIPTION OF THE DRAWINGS

The following drawings form part of the present specification and are included to further demonstrate certain aspects of the present inventions. The disclosure can be better understood by reference to one or more of these drawings in combination with the detailed description of specific embodiments presented herein.

DETAILED DESCRIPTION

The present invention provides methods for identifying tumors which are responsive to oxaliplatin in individuals. The methods involves the gene expression analysis of RNA isolated from tissue or other biological sources such as blood, urine or feces using nCounter Assays from Nanostring Technologies Inc. or other gene expression methodologies such as microarray, RNA-Seq, hybrid capture RNA sequencing or other state of the art RNA expression profiling methodologies, identifying the colon cancer intrinsic subtypes, identifying the subtypes that received benefit from oxaliplatin. As used herein isolated RNA is meant to convey any separation of RNA from its environment in a cell, including any fractionation, binding, filtration, degradation or even cell rupture such as a lysate.

Clinical Samples and Histological Evaluation Used in this Description.

Samples used in this disclosure were from NSABP clinical trial C-07. This trial enrolled patients between 02/2000 and 11/2002 to compare oxaliplatin and bolus 5-FU/LV to bolus 5FU/LV alone for resected stage II and III colon cancer[2]. C-07 was approved by an Institutional Review Board and informed consent was obtained from each subject for biomedical research.

I. nCounter Assays Used to Determine Gene Expression

The nCounter platform by Nanostring Technologies was used to profile gene expression in RNAs isolated from rumors collected in NSABP clinical trial C-07 which is an ideal platform for a clinical assay for chemically modified and degraded RNAs isolated from FFPE because it requires no enzymology, requires small amounts of total RNA, capture and detection probes target less than 100 bp sequence, and the process is largely automated requiring little hands on time.

The C-07 customized nCounter code set consisted of 296 genes plus 6 positive and 8 negative technical control genes. The 2% genes included in this nCounter code set were selected for the following reasons; the genes were prognostic or predictive for oxaliplatin benefit in the C-07 discovery cohort using whole genuine DASL arrays (WG_DASL) from Illumina Inc or were part of significant pathways identified in C07 DASL data analysis or were from the literature or other internal data.

We have profiled 296 genes in 1840 patients using the nCounter Assay system (Nanostring Technologies, Seattle Wash.). Clinical data and nCounter data for the discovery dataset were merged and anonymized by the honest broker at the University of Pittsburgh as defined by standard operations under IRB approval of NSABP Biospecimen Bank and Biostatistics Center. We have developed a predictive algorithm to classify tumors into oxaliplatin benefit or no benefit group using discovery cohort of 848 patients without access to the data from the remaining 992 patients (validation cohort).

II. Study Design

Figure 1:
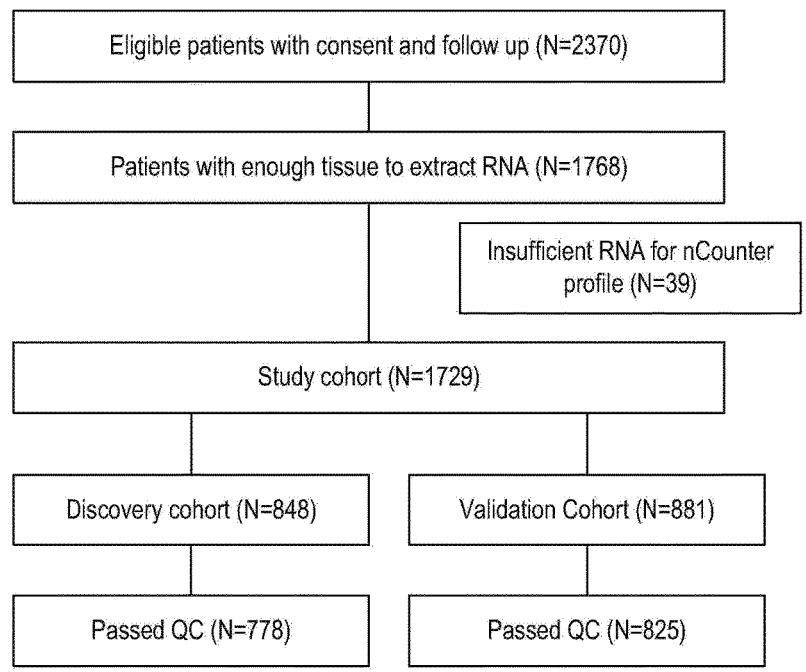
FIG. 1 Design of Study for discovery and validation of a signature to identify patients who will benefit from oxaliplatin. In this description only the discovery cohort has been used for signature development.

For C07, 2409 patients were enrolled in C-07 and all cases with tumor blocks, proper consent, clinical follow-up information and sufficient RNA yields were used in this study (N=1840). These cases were split into a discovery (N=848) and a validation (N=992) cohort (FIG. 1). The present signature was developed with the discovery cohort.

Figure 2:
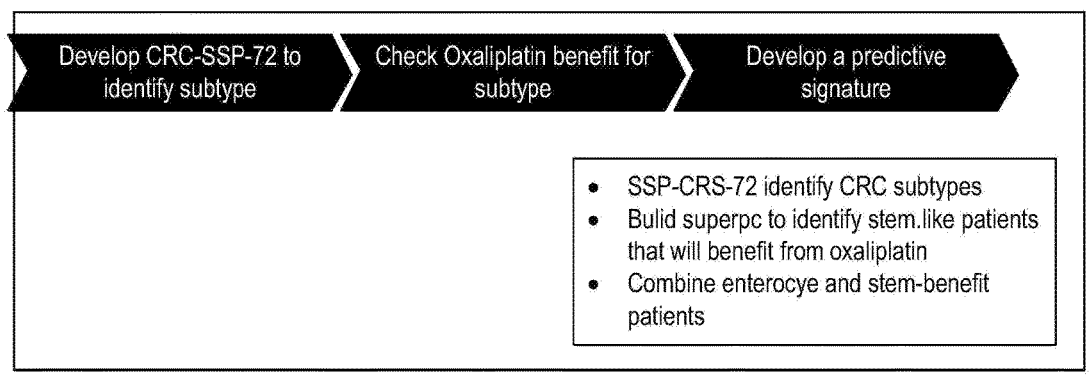
FIG. 2 shows the steps that were taken to develop predictive algorithm using nCounter data from the discovery cohort of C-07.

A. Intrinsic Subtype and Oxaliplatin Benefit:

The steps for signature development are summarized in FIG. 2.

With the goal of developing genomic predictive biomarker for oxaliplatin benefit, we first identified intrinsic subtypes and tested oxaliplatin benefit in each subtype. The disclosed methods focused on the CRC intrinsic subtypes identified by Sadanandam[6], and the CCS intrinsic subtypes identified by De Sousa[7]. Since nCounter assay was designed before the publication of the above papers, only a small proportion of intrinsic genes were matched to genes included in the nCounter assay. For example, for the CRC study[6], among 1262 non-specific filtered genes, only 72 exist in the nCounter code dataset, and among 786 identified intrinsic subtyping genes, only 56 exist in the nCounter code dataset. Our analysis indicated that subtype can be identified with a subset of 786 genes. Based on the 56 genes, using SSP method, specifically, we checked the Spearman correlation between each sample and the subtype centroid, and then assigned each sample to the subtype to which it was most correlated. This method correctly identified subtype in 79% of the samples.

To improve the robustness of subtype identification, we redeveloped centroid for each subtype based on the 72 genes that overlap between C-07 nCounter code dataset and the original CRC training dataset. We then applied SSP method to the C-07 training data i.e., we checked the Spearman correlation between each sample and the subtype centroid using the 72 genes (Table 1), then assigned each sample to the most correlated subtypes. We can correctly identify the subtype in 80% of the samples (Table 2). Clinical variables such as T stage, nodal status perforation and mutation status of BRAF, KRAS, NRAS and PIK3CA of each subtype are shown in Table 3.

TABLE 1

Centroid of CRC-SSP-72.

| | Enterocyte | Goblet.like | Inflammatory | Stem-like | TA |
|---|---|---|---|---|---|
| AKAP12 | −0.1564 | −0.3258 | −1.00E−04 | 0.6652 | −0.1946 |
| ANKRD44 | 0.0701 | −0.1685 | 0.2335 | 0.0874 | −0.1798 |
| BGN | −0.2625 | −0.3363 | 0.1203 | 0.684 | −0.2285 |
| BHLHE4I | 0.1079 | 0.075 | 0.0015 | 0.2663 | −0.3092 |
| BMP7 | −0.2046 | −0.0645 | −0.143 | 0.04 | 0.2408 |
| C8orf84 | −0.4073 | 0.5791 | −0.0724 | −0.1541 | 0.0682 |
| CAB39L | −0.0904 | −0.2837 | −0.4717 | 0.1316 | 0.4798 |
| CDKN2B | 0.6162 | −0.4035 | −0.0118 | 0.222 | −0.2867 |
| CKMT2 | 0.0206 | −0.2473 | −0.2254 | −0.0649 | 0.3515 |
| COL11AI | −0.4436 | −0.3797 | 0.189 | 0.7476 | −0.1898 |
| COMP | −0.4057 | −0.202 | −0.1175 | 0.7747 | −0.1101 |
| CPE | 0.091 | 0.1071 | −0.4766 | 0.2741 | 0.0311 |
| CSGALNACT1 | −0.2585 | −0.0478 | −0.0254 | 0.2363 | 0.0324 |
| CXCL10 | −0.1897 | −0.1776 | 0.7137 | −0.0052 | −0.302 |
| CXCL11 | −0.203 | −0.115 | 0.6691 | −0.0649 | −0.2545 |
| CXCL13 | 0.11 | −0.2356 | 0.8126 | −0.1015 | −0.4541 |
| CXCL2 | −0.1416 | 0.0466 | 0.1917 | −0.2284 | 0.0826 |
| CXCL9 | −0.2303 | −0.2078 | 0.7334 | −0.006 | −0.2731 |
| CYP1B1 | −0.3509 | −0.242 | 0.0875 | 0.8449 | −0.3248 |
| DAPK1 | −0.2495 | 0.3342 | 0.3441 | 0.1757 | −0.4336 |
| DCBLD2 | −0.2662 | −0.1791 | 0.1036 | 0.335 | −0.0522 |
| DPEP1 | −0.1993 | 0.0196 | −0.4644 | −0.0446 | 0.4881 |
| EPB41L4B | 0.1808 | −0.0063 | −0.2888 | −0.3419 | 0.3594 |
| ERAP2 | −0.0712 | 0.0416 | 0.4002 | −0.1821 | −0.1445 |
| F5 | −0.2002 | 0.0195 | 0.2094 | −0.0196 | −0.03 |
| FAP | −0.2881 | −0.2525 | 0.1586 | 0.6969 | −0.301 |
| FGL2 | 0.1732 | −0.1883 | 0.3211 | 0.1058 | −0.3093 |
| FN1 | −0.2859 | −0.4114 | 0.1302 | 0.5476 | −0.0764 |
| FNDC1 | −0.2566 | −0.3827 | −0.0213 | 0.8409 | −0.2125 |
| GBP1 | −0.1684 | −0.2325 | 0.6939 | 0.0308 | −0.2952 |
| GBP4 | −0.1999 | −0.1174 | 0.7101 | −0.1899 | −0.1937 |
| GPX3 | 0.0253 | −0.1816 | −0.0432 | 0.4493 | −0.203 |
| GRM8 | −0.0273 | −0.1092 | −0.3808 | −0.2021 | 0.5153 |
| GZMB | −0.2513 | −0.4275 | 0.3314 | −0.167 | 0.2865 |

TABLE 1-continued

Centroid of CRC-SSP-72.

| | Enterocyte | Goblet.like | Inflammatory | Stem-like | TA |
|---|---|---|---|---|---|
| HGD | 0.2535 | 0.3355 | −0.0656 | −0.3365 | −0.0593 |
| HOXA13 | −0.0301 | 0.1091 | −0.0917 | −0.2152 | 0.1795 |
| HSD17B2 | 0.6687 | −0.0054 | 0.1407 | −0.3991 | −0.2153 |
| ID4 | −0.1789 | 0.0325 | −0.2977 | 0.4248 | 0 |
| IDO1 | −0.2064 | −0.1664 | 0.7754 | −0.2062 | −0.1969 |
| IL8 | −0.166 | −0.0459 | 0.3226 | 0.0624 | −0.156 |
| INHBA | −0.3224 | −0.2377 | 0.1021 | 0.6646 | −0.2233 |
| MFAP5 | 1.00E−04 | −0.3641 | −0.1964 | 0.8067 | −0.2264 |
| MGP | 0.0509 | −0.4134 | −0.1745 | 0.8961 | −0.3097 |
| MMP11 | −0.1743 | −0.2439 | −0.1581 | 0.462 | 0.0318 |
| MMP28 | 0.4253 | 0.2425 | 0.1082 | −0.1931 | −0.3441 |
| NFIB | 0.0535 | −0.0317 | −0.5168 | 0.0032 | 0.3672 |
| OAS2 | −0.1136 | 0.0199 | 0.4392 | −0.0611 | −0.2234 |
| PAPPA | −0.0641 | −0.2033 | 0.0437 | 0.3593 | −0.1342 |
| PIGR | 0.2984 | 0.2771 | 0.2527 | −0.4536 | −0.2038 |
| PLA2G12B | −0.0591 | −0.2634 | −0.3123 | −0.1001 | 0.5015 |
| POU2AF1 | 0.3543 | 0.2138 | 0.147 | −0.1889 | −0.3155 |
| PRAP1 | −0.0074 | −0.2188 | −0.4551 | 0.0767 | 0.4181 |
| PROM2 | 0.2046 | 0.1593 | −0.0655 | −0.2981 | 0.0462 |
| PSMB9 | −0.1726 | −0.0019 | 0.4983 | −0.2105 | −0.1072 |
| PTPRC | 0.0416 | −0.252 | 0.5649 | 0.1694 | −0.4187 |
| ROBO1 | −0.1221 | −0.2991 | 0.0818 | 0.2661 | −0.0014 |
| SDC2 | −0.0982 | −0.2924 | −0.0399 | 0.5358 | −0.1257 |
| SELL | 0.0788 | −0.1222 | 0.2456 | 0.0016 | −0.1589 |
| SERPINE1 | −0.1613 | −0.116 | 0.0757 | 0.3678 | −0.1574 |
| SFRP2 | −0.2103 | −0.5022 | 0.0497 | 1.0716 | −0.3926 |
| SGK2 | 0.2445 | −0.2138 | −0.4084 | −0.2707 | 0.4818 |
| SLC4A4 | 1.099 | 0.1349 | 0.0933 | −0.461 | −0.4826 |
| SPARC | −0.1227 | −0.3431 | 0.0146 | 0.6662 | −0.218 |
| SPP1 | −0.3134 | −0.1681 | 0.4032 | 0.4321 | −0.3238 |
| SSPN | −0.0575 | −0.0801 | −0.1318 | 0.5308 | −0.206 |
| STC1 | −0.3185 | −0.1163 | 0.2305 | 0.2822 | −0.1135 |
| TACSTD2 | −0.0954 | 0.2113 | −0.0379 | 0.109 | −0.1196 |
| TGFBR3 | −0.1721 | −0.0829 | −0.016 | 0.04 | 0.1378 |
| TM4SF1 | −0.1527 | −0.1754 | −0.0883 | 0.0963 | 0.1938 |
| TYMS | −0.1895 | 0.1904 | 0.4728 | −0.3805 | −0.0701 |
| VCAN | −0.1637 | −0.3038 | −0.0031 | 0.7104 | −0.2344 |
| VNN1 | 0.0753 | 0.2341 | 0.4957 | −0.2096 | −0.4016 |

TABLE 2

Consistency between CRC-SSP-72 and original algorithm in identifying CRC subtypes.

| | | Truth | | | | |
|---|---|---|---|---|---|---|
| | | Enterocyte | Goblet-like | Inflam-matory | Stem-like | TA |
| Prediction | Enterocyte | 40 | 0 | 0 | 0 | 4 |
| | Goblet.like | 5 | 42 | 2 | 0 | 3 |
| | Inflammatory | 11 | 9 | 68 | 2 | 4 |
| | Stem-like | 8 | 8 | 6 | 75 | 10 |
| | TA | 0 | 4 | 2 | 0 | 84 |

TABLE 3

Patient characteristics by intrinsic subtype identified by CRC-SSP-72.

| | | Enterocyte | Goblet-like | Inflammatory | Stem-like | TA |
|---|---|---|---|---|---|---|
| Gender | F | 43 (47.3%) | 22 (34.9%) | 89 (44.1%) | 95 (39.7%) | 79 (43.2%) |
| | M | 48 (52.7%) | 41 (65.1%) | 113 (55.9%) | 144 (60.3%) | 104 (56.8%) |
| Stage | II | 26 (28.6%) | 20 (31.7%) | 88 (43.6%) | 57 (23.8%) | 42 (23%) |
| | III | 65 (71.4%) | 43 (68.3%) | 114 (56.4%) | 182 (76.2%) | 141 (77%) |
| Grade | Diff | 80 (87.9%) | 51 (81%) | 126 (62.4%) | 194 (81.2%) | 168 (91.8%) |
| | undiff | 11 (12.1%) | 12 (19%) | 76 (37.6%) | 45 (18.8%) | 15 (8.2%) |
| TStage | T12 | 15 (16.5%) | 11 (17.5%) | 17 (8.4%) | 7 (2.9%) | 28 (15.3%) |
| | T3 | 71 (78%) | 46 (73%) | 176 (87.1%) | 213 (89.1%) | 144 (78.7%) |
| | T4 | 5 (5.5%) | 6 (9.5%) | 9 (4.5%) | 19 (7.9%) | 11 (6%) |
| Perforation | 0 | 89 (97.8%) | 62 (98.4%) | 196 (97%) | 231 (96.7%) | 179 (97.8%) |
| | 1 | 2 (2.2%) | 1 (1.6%) | 6 (3%) | 8 (3.3%) | 4 (2.2%) |
| Nodes positive detected | 0 | 26 (28.6%) | 20 (31.7%) | 88 (43.6%) | 57 (23.8%) | 42 (23%) |

TABLE 3-continued

Patient characteristics by intrinsic subtype identified by CRC-SSP-72.

|  |  | Enterocyte | Goblet-like | Inflammatary | Stem-like | TA |
|---|---|---|---|---|---|---|
|  | 1-3 | 43 (47.3%) | 32 (50.8%) | 78 (38.6%) | 107 (44.8%) | 108 (59%) |
|  | 4+ | 22 (24.2%) | 11 (17.5%) | 36 (17.8%) | 75 (31.4%) | 33 (18%) |
| MSI status | MSS | 77 (100%) | 50 (87.7%) | 131 (72.4%) | 193 (94.1%) | 162 (97.6%) |
|  | MSI | 0 (0%) | 7 (12.3%) | 50 (27.6%) | 12 (5.9%) | 4 (2.4%) |
| BRAFmutated | w | 83 (91.2%) | 48 (78.7%) | 145 (72.9%) | 205 (86.1%) | 177 (96.7%) |
|  | m | 8 (8.8%) | 13 (21.3%) | 54 (27.1%) | 33 (13.9%) | 6 (3.3%) |
| KRASmutated | w | 64 (71.9%) | 26 (44.1%) | 129 (66.8%) | 126 (54.1%) | 121 (66.9%) |
|  | m | 25 (28.1%) | 33 (55.9%) | 64 (33.2%) | 107 (45.9%) | 60 (33.1%) |
| METmutated | w | 85 (96.6%) | 56 (94.9%) | 184 (95.3%) | 227 (97.4%) | 174 (96.1%) |
|  | m | 3 (3.4%) | 3 (5.1%) | 9 (4.7%) | 6 (2.6%) | 7 (3.9%) |
| NRASmutated | w | 85 (96.6%) | 56 (94.9%) | 190 (99%) | 226 (97%) | 176 (97.2%) |
|  | m | 3 (3.4%) | 3 (5.1%) | 2 (1%) | 7 (3%) | 5 (2.8%) |
| PIK3CAmutated | w | 74 (84.1%) | 46 (76.7%) | 142 (73.2%) | 175 (74.8%) | 158 (87.3%) |
|  | m | 14 (15.9%) | 14 (23.3%) | 52 (26.8%) | 59 (25.2%) | 23 (12.7%) |
| RFI Status | 0 | 59 (64.8%) | 4 (74.6%) | 173 (85.6%) | 141 (59%) | 132 (72.1%) |
|  | 1 | 32 (35.2%) | 16 (25.4%) | 29 (14.4%) | 98 (41%) | 51 (27.9%) |
| OS Status | 0 | 54 (59.3%) | 40 (63.5%) | 156 (77.2%) | 138 (57.7%) | 121 (66.1%) |
|  | 1 | 37 (40.7%) | 23 (36.5%) | 46 (22.8%) | 101 (42.3%) | 62 (33.9%) |

Figure 3:
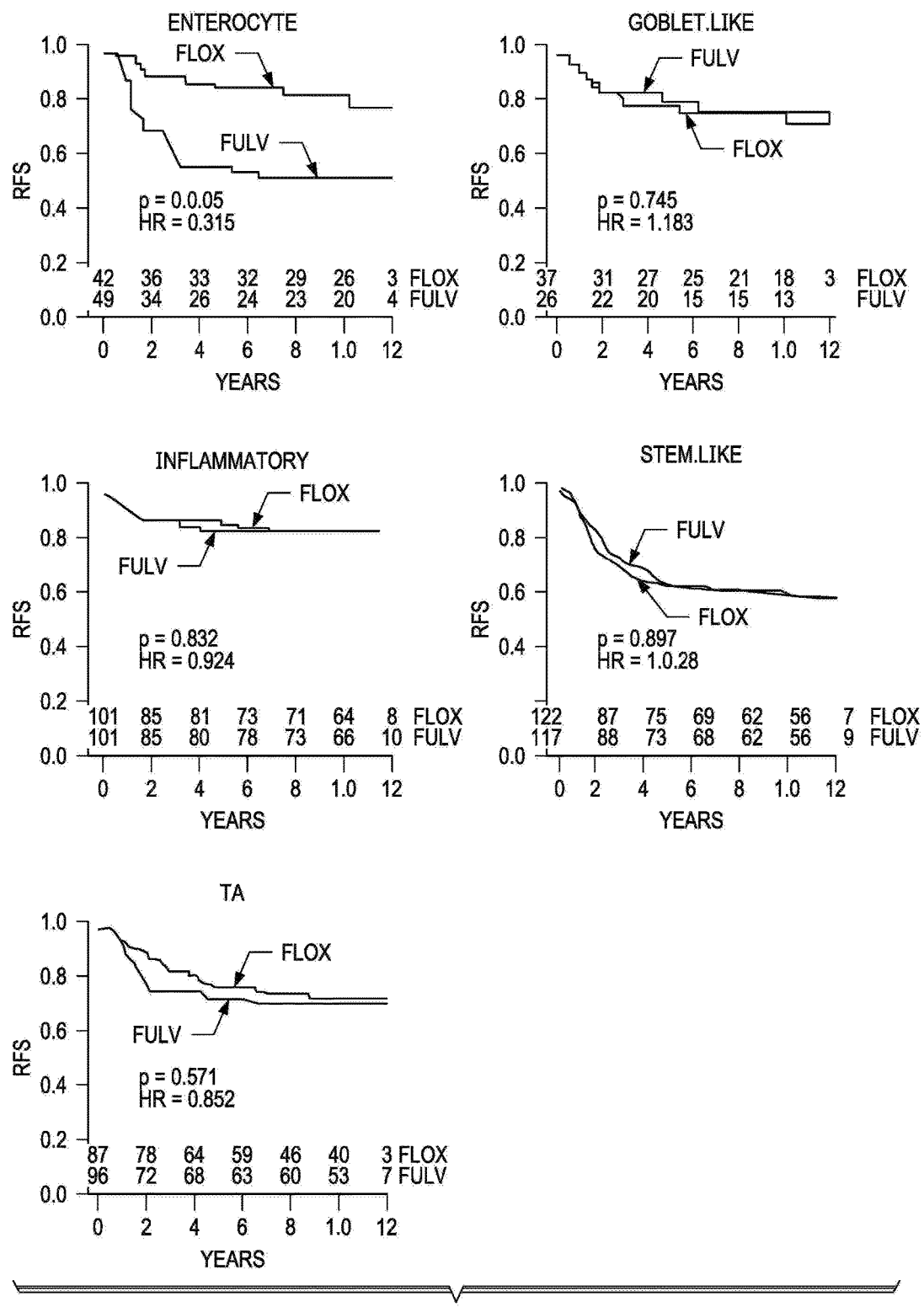
FIG. 3 Kaplan Meier Plots of each CRC subtype using our gene signature by CRC-SSP-72 according to treatment (FULV versus FOLFOX) using recurrence free survival (RFS) as the end point. Among identified CRC subtypes, only Enterocyte received significant benefit (HR=0.315, p=0.005).
Figure 4:
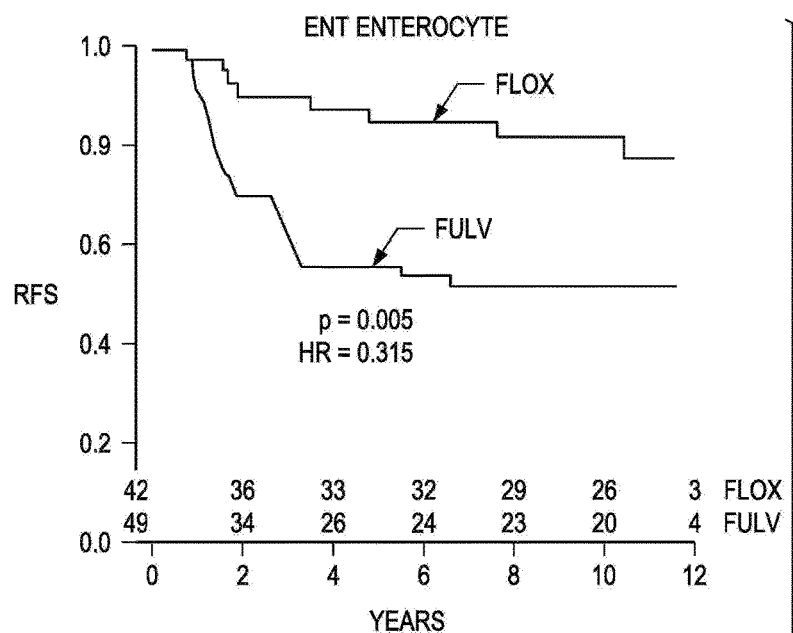
FIG. 4 Kaplan Meier Plots of the Enterocyte subtype and of all of the other subtypes (Goblet-like, Inflammatory, Stem-like and TA) combined into one group (Others) There is significant treatment-group interaction (p=0.012)
Figure 4:
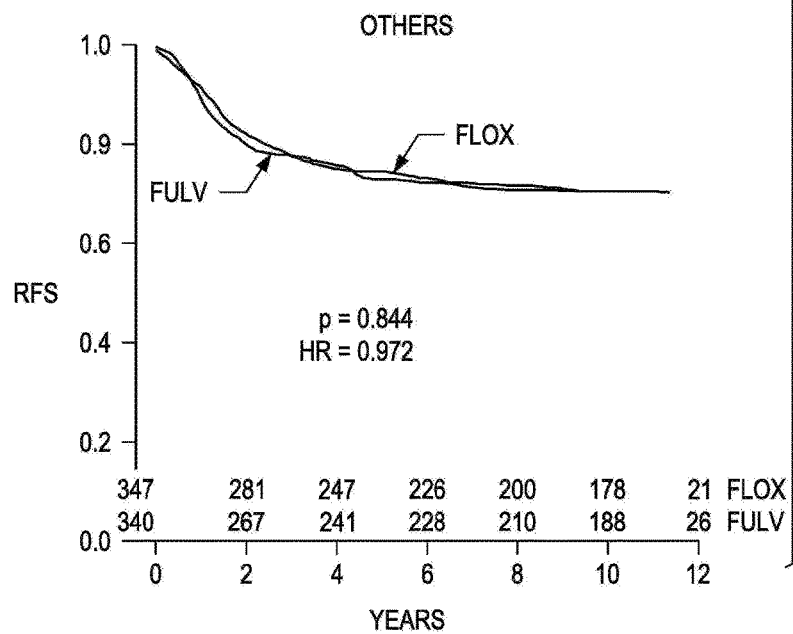
Figure 5:
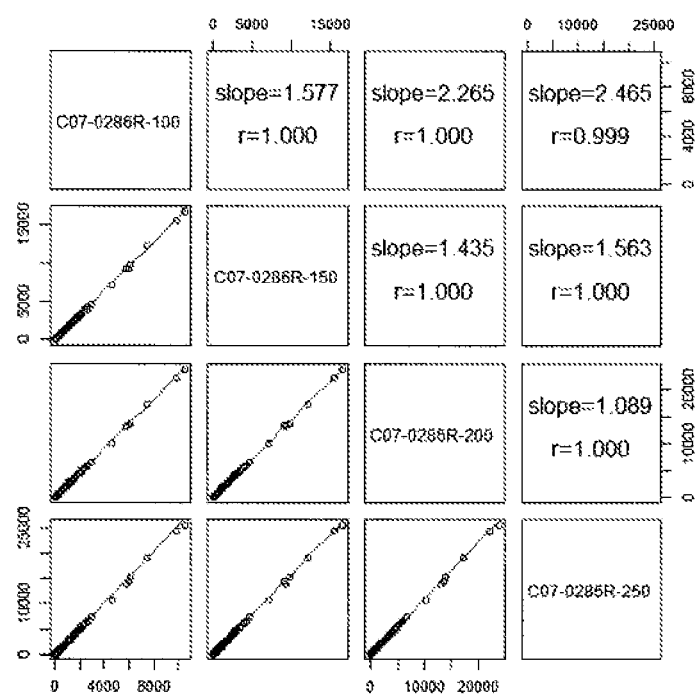
FIG. 5 Reproducibility of a C07 sample (C-07-0286) measured by nCounter. This sample was tested using 100, 150, 200, and 250 ng of total RNA as input.

As shown in FIG. 3, among identified CRC subtypes, only Enterocyte received significant benefit (HR=0.315, p=0.005). In combining all other four subtypes. Goblet-like, Inflammatory, Stem-like and TA as a non-benefit group, there is significant treatment-group interaction (p=0.012) (FIG. 4). However when stage II and III CRC patients were tested separately only stage III patients showed differential benefit from oxaliplatin when subtyped with our 72 gene signature (FIG. 5).

Similarly, we also identified CCS colon cancer subtypes which include CCS1, CCS2 and CCS3[7]. Consistent with other studies the CRC clustering and CCS clustering are correlated with each other, i.e., most CCS1 patients are TA or Enterocyte patients, most CCS2 patients are inflammatory and most CCS3 are stem-like patients. Since CCS did not separate Enterocyte which received significant benefit from oxaliplatin from other TA patients, we decided to use SSP-72 to identify CRC subtypes.

III. RNA Expression Profiling using nCounter Assay System
Gene Expression Profiling by nCounter Assay System.

The nCounter platform was selected as the platform for a clinical assay for degraded RNAs isolated from FFPE because it requires no enzymology, requires only 100 to 300 ng of total RNA, capture and detection probes target less than 100 bp sequences, and the process is largely automated requiring little hands on time. The C-07 customized nCounter code set consisted of 296 genes plus 6 positive and 8 negative technical control genes. The 296 genes included in this nCounter code set were selected for the following reasons: the genes were prognostic or predictive for oxaliplatin benefit in the C07 discovery cohort using DASL data or were part of significant pathways identified in C07 DASL data analysis or were from the literature. nCounter assay data processing QC of the nCounter Assay Data:
Quality control of the data was performed using default flags in the NSolver software that is provided by the manufacturer:
1) Imaging flag—sample removed if less than ¾ of the expected fields of view are captured by the camera (0.75*600=450 minimum FOVs)
2) Binding Density—sample removed if the binding density falls outside the range 0.05–2.25
3) Positive Control Flag—sample removed if the positive spikes do not follow the expected linear trend (r^2<0.95)
4) 0.5 fm Detection Flag—sample removed if the 0.5 fm positive control is within two standard deviations of the negative controls
5) Tech Normalization Flag—for the raw data, median (sum(pos(controls))/sum(positive control); sample removed if the technological normalization factor >3 or <0.3
6) Biological Normalization Flag—after adjusted by technical normalization, median (geomean(pos(housekeeping controls)/geomean(house-keeping control); sample removed if the biological normalization factor <0.1 or >10. In this data, KIAA1539, MADD, RAB1A, C17orf79, PDCD10, NFYC were selected as housekeeping genes.
7) If repeated measurements for an individual both pass above criteria, the lane with the lesser total counts will be removed With the above criteria, 778 out of 848 samples (91.75%) pass QC and were used for signature development.

1. Nanostring Data Normalization

After preprocessing data, we normalized each tumor for technical variability with the stint of the positive controls inherent to nCounter assay and within sample reference normalized with the geometric mean of 6 internal reference genes (KIAA1539, MADD, RAB1A, C17orf79, PDCD10, NFYC).

2. Analytical Performance of mRNA Expression Profile by nCounter:

Dynamic range and limit of detection for the nCounter assay can be estimated from synthetic, spike-in controls included with every sample. Positive controls are spiked into the reaction at concentrations from 0.125-128 fM, representing a fold-change of 1024. Measurements of these controls are highly linear (median $r^2$=0.99 across all discovery samples) in this range. Eight negative control probes, representing sequences not found in the human transcriptome, are also included in each reaction. The lowest positive control, 0.125 fm, represents approximately 0.2 copies per cell, and is detected at least 2 standard deviations above the mean of the negative controls. If $r^2$ for the positive spikes drops below 0.95 or the 0.125 fm spike is not detected 2 standard deviations above the mean of the negative controls, the reaction is considered failed and that sample is repeated or removed from further analysis.

We also tested 11 pairs of samples as duplicate. For these duplicate samples, we calculated the correlation coefficients for the gene expression, the minimum of correlation coefficient is 0.9912, and mean is 0.9925, standard deviation is 0.0021.

To address assay reproducibility and required amount of input RNA, we first performed several samples using 100, 150, 200, and 250 ng of total RNA as input. Results for one representative sample are shown in FIG. 5. The raw data demonstrates an almost linear increase in signal with increased input material. However, normalized data were nearly identical demonstrating that we can use 100 ng of total RNA as the starting material for the nCounter assay.

In the C-07 discovery cohort the enterocyte subtype in CRCA subtype received benefit from oxaliplatin, however, this signature failed to validate in the independent data set. One reason that the signature failed to validate, may be due to the non-optimal identification of the enterocyte subtype. Our nCounter code set was created before the CRCA subtypes were described and therefore was not designed for subtype identification and unfortunately only includes a very small number of genes for enterocyte identification. Thus accurate identification of the enterocyte subtype was not optimal with the current code set Another potential problem that may have contributed to the failure to validate our signature was the possibility that other subtypes could include patients who benefited from oxaliplatin. For example the stem-like and TA subtypes may need to be further split into sub-subtypes. TA is heterogeneous group which has a gene expression pattern similar to transit-amplifying progenitor cells which differentiate into goblet and enterocyte cells in the normal colonic crypt. Thus TA may be further refined into sub-subtypes based on their future potential fate, i.e., TA cells that are more likely to differentiate into enterocytes and those that differentiate into goblet. We would hypothesize that only the enterocyte-like subtype within TA would receive benefit from oxaliplatin. However, because our nCounter code set only includes a small number of genes for enterocyte and goblet-like identification, we could not exploit this hypothesis in the nCounter data. We also attempted to split the stem-like subtype but were unable to find a satisfactory split for oxaliplatin benefit in this subtype.

As discussed above, the basis of our previous work is that subtypes have different molecular properties, which determine the degree of benefit they receive from treatment. However, because the identification of CRC subtypes is still in an exploratory phase, it is uncertain how to be identify relevant subtypes for oxaliplatin benefit.

Disclosed herein are a description of the genes and methods for identifying the association of gene modules with CRC subtypes and their association with clinical behavior with an emphasis on identifying patients who receive benefit from oxaliplatin. Identification of modular gene sets and their association to particular CRC subtypes allows not only for subtype identification but also a description of those subtypes, how they are similar and how they are different which will enable a better understanding of clinical behavior, In the second study, we took a well-established systematic approach, Weighted Gene Correlation Network Analysis (WGCNA), to identify acne modules, i.e., correlated gene expression networks and evaluated how these modules are related to subtypes. Gene modules are generally comprised of functionally related genes. Understanding, the gene modules which characterize subtypes will enable us to understand how each subtype is correlated to each other, and the molecular mechanisms of different prognostic or predictive behavior of each subtype. We have selected genes for a new code set which will enable us to better identify functional, clinically relevant CRC subtypes.

Additional studies profile C-07 with this new code set which provides better understanding of how each module is related to oxaliplatin benefit. Then we reevaluate which current subtype system (among CCS, CRCA, CCMS) is the best for identifying patients that will get benefit from oxaliplatin or we develop a better classification system to define subtypes M terms of oxaliplatin benefit. In addition, we also develop signatures based on other approaches by combining, information obtained from gene module analyses.

Study Design II

We have downloaded the original training datasets for CCS, CCMS and CRCA classifier. The original training dataset for CCS and CCMS includes 90 and 566 patients respectively. Note the original CRCA training dataset is the combination of two datasets, to avoid the impact of batch effect, in our analyses; we analyzed the two datasets for CRCA analysis separately.

Figure 6:
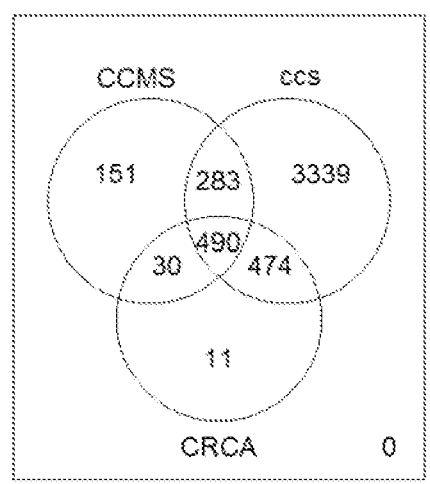
FIG. 6 Venn diagram of genes used for developing subtype classifiers.

For each dataset, we performed WGCNA analysis on the genes used for the specific classifier. In addition, although these three classifiers all started with genes having large variance, the list of genes is different (FIG. 2). We also performed WGCNA analysis on the union of genes used for all three classifiers (4510). A Venn diagram of genes used for developing subtype classifiers appear in FIG. 6.

WGCNA constructed a network using adjacency matrix, which is constructed by using the soft-threshold approach ($\beta=8$) on the matrix of pair-wise correlation coefficients. Topological overlap distance was then calculated from the adjacency matrix, and used to build a hierarchical clustering tree. Modules were defined, as branches of a hierarchical clustering tree, with a minimum module size of 50 genes. A module eigengene distance threshold of 0.4 was also used to merge highly similar modules. Each module is assigned a unique color label. For the convenience of comparison, we matched the module colors from different training dataset based on modules identified in CCMS training dataset. WGCNA analysis was done using WGCNA R package We assigned each patient to different subtype in CCS, CRCA or CCMS clustering system using SSP method, the centroid was obtained from the original publications. We further identified differentially expressed genes for each subtype using SAM method, and plotted such information underneath the WGCNA tree.

Results

For each dataset, we performed WGCNA analysis on the genes used for the specific classifier (data not shown) and the union of genes used for training three classifiers (4510 genes) in the WGCNA analysis in CCMS training datasets. The module colors are assigned by WGCNA algorithm automatically, based on the ranking of module size.

To understand how these modules are related to subtype, information of genes' expression in each subtype was added in the tree plot. In CCMS training dataset( ), six lame modules were: identified, and these gene modules express differently in different subtypes. Turquoise module, the largest module, includes 1424 genes, and most of these over expressed in step-like/ccs3/CCMS4 and CCMS6. Importantly, the turquoise module contains stromal and epithelial to mesenchymal related genes demonstrating the functional information that can be inferred with modular analysis. The black module includes 866 genes, they overexpressed in stem-like/ccs3/CCMS4, and inflammatory/ccs2/CCMS2.

The brown module includes 649 genes, overexpressed in inflammatory/ccs/CCMS2. The yellow module includes 613 genes, overexpressed in TA/ccs1/CCMS1/CCMS5. The green module includes 506 genes, doesn't seem to have a clear pattern. The red module includes 451 genes, overexpressed in goblet/CCM3, enterocyte/CCMS6.

TABLE 4

| | # genes | Enterocyte | Goblet-like | Inflammatory | Stem-like | TA |
|---|---|---|---|---|---|---|
| Turquoise | 1424 | | | | | + |
| Black | 866 | | | + | + | |
| Brown | 649 | | | + | | |
| Yellow | 613 | | | | | + |
| Green | 506 | | | | | |
| Red | 452 | + | + | | | |

Similar analyses were performed for other datasets. For the convenience of comparison, we have matched the module color from other datasets to module colors in CCMS training dataset. As shown in FIG. 3B-D, although modules identified in other datasets are different from modules identified in CCMS training datasets, there is significant overlap for modules identified from different datasets, and these modules have distinct expression pattern in different subtypes.

To identify genes that are preserved in different datasets in terms of module membership, we further laid out the significant overlap modules identified in different datasets in the same tree, i.e., genes that are from modules that don't have significant overlap are colored gray.

The data (not shown) shows significant overlap among modules from other datasets, especially for turquoise and black modules identified from CCMS dataset. For brown, yellow and red modules identified in CCMS dataset, they are moderately preserved in other datasets, and sometimes they were further split into smaller modules. For example, in ccs datasets, the brown module in CCMS dataset split into both brown and green modules. Gene selection focuses on gene, that are preserved hi modules with particular locus on hub genes, i.e., genes which have strong correlation with a large number of genes.

We have identified a list of genes that will be used for identification of subtypes and sub-subtypes with differential benefit from oxaliplatin Table 6, Genes will be selected from this table to include in our code set to profile C-07, further refinement of the code set will be determined by additional criteria such as a gene's correlation between fresh and FFPE isolated RNA, the preservation in other datasets, and functional analysis.

TABLE 5

Genes for identification of subtypes and sub-subtypes

| | CCMS | ccs | CRCA1 | CRCA2 | potential 1 |
|---|---|---|---|---|---|
| RGL3 | black | black | black | gray | |
| GABRB2 | black | gray | black | black | |
| ZDHHC11 | turquoise | gray | gray | gray | |
| HOTTIP | black | gray | gray | gray | |
| TCTE3 | black | gray | black | black | |
| FAM185A | black | gray | black | black | |
| NKAIN2 | turquoise | turquoise | turquoise | gray | |
| SV2C | turquoise | gray | turquoise | turquoise | |
| C17orf78 | turquoise | turquoise | turquoise | gray | |
| ERVMER34-1 | turquoise | turquoise | turquoise | turquoise | |
| ZNF395 | turquoise | gray | gray | gray | |
| NTRK2 | brown | gray | gray | gray | |
| SH3TC2 | turquoise | turquoise | gray | turquoise | |
| SLC7A8 | turquoise | gray | gray | turquoise | |
| LURAP1L | turquoise | gray | gray | turquoise | |
| EDAR | turquoise | turquoise | turquoise | turquoise | |
| SLC6A20 | black | gray | gray | gray | |
| FLVCR1-AS1 | brown | gray | brown | brown | |
| RUSC1-AS1 | turquoise | turquoise | gray | gray | |
| LCN15 | turquoise | gray | gray | gray | |
| PLEKHS1 | black | black | black | gray | |
| CLDN2 | brown | brown | brown | brown | |
| CYP4X1 | brown | green | brown | brown | |
| TRIB1 | turquoise | gray | turquoise | turquoise | |
| LSS | brown | green | brown | gray | |
| ZDHHC5 | brown | green | gray | gray | |
| LRRC8E | brown | green | gray | brown | |
| OTUB2 | brown | brown | brown | brown | |
| SCARNA2 | yellow | gray | gray | gray | |
| CAMTA1 | brown | gray | gray | gray | |
| IL1A | black | magenta | gray | black | |
| CCL20 | yellow | red | green | red | |
| NFKBIZ | black | black | black | black | |
| ZC3H12A | black | black | black | black | |
| CXCL1 | black | black | black | black | |
| CXCL2 | black | black | black | black | |
| CXCL3 | brown | brown | gray | gray | |
| C11orf71 | black | gray | black | black | |
| KRTAP4-1 | yellow | yellow | yellow | gray | |
| MACROD1 | brown | green | gray | gray | |
| SAMD12 | turquoise | gray | gray | turquoise | |
| GABRA2 | turquoise | gray | gray | turquoise | |
| IRS2 | turquoise | gray | gray | gray | |

TABLE 5-continued

Genes for identification of subtypes and sub-subtypes

| | CCMS | ccs | CRCA1 | CRCA2 | potential 1 |
|---|---|---|---|---|---|
| SLC44A5 | green | yellow | gray | red | |
| SEC16B | green | gray | yellow | gray | |
| DEPTOR | turquoise | turquoise | gray | turquoise | |
| EPPK1 | brown | green | gray | gray | |
| ALDH7A1 | brown | green | gray | gray | |
| UTS2 | black | gray | black | black | |
| MYCN | brown | gray | brown | brown | |
| CLCN4 | black | black | black | gray | |
| RGMB | brown | green | brown | gray | |
| NMNAT3 | brown | gray | gray | gray | |
| DCDC2 | black | gray | gray | gray | |
| HIPK2 | black | gray | black | gray | |
| ANKRD17 | green | green | gray | gray | |
| HINT3 | turquoise | gray | gray | turquoise | |
| AIG1 | turquoise | gray | gray | gray | |
| TPD52L1 | brown | gray | gray | gray | |
| ERO1L | black | magenta | black | gray | |
| SPTBN1 | black | gray | black | gray | |
| CD9 | brown | green | gray | gray | |
| ENC1 | black | gray | gray | gray | |
| DNAJC16 | brown | green | gray | gray | |
| NNT | green | green | gray | red | |
| LRRC6 | brown | gray | gray | gray | |
| NETO2 | brown | green | brown | brown | |
| STK31 | green | yellow | yellow | gray | |
| EPB41L2 | green | green | gray | gray | |
| SULT1C2 | brown | gray | gray | gray | |
| ANKRD18A | brown | gray | gray | brown | |
| SAMD5 | brown | gray | brown | brown | |
| NRD1 | black | gray | black | gray | |
| 6-Mar | turquoise | gray | gray | turquoise | |
| PLCB1 | green | yellow | yellow | gray | |
| ZNF678 | green | yellow | yellow | red | |
| ZNF738 | green | gray | gray | gray | |
| ZNF702P | green | gray | gray | gray | |
| DEPDC7 | green | gray | gray | yellow | |
| ALPK1 | green | yellow | gray | gray | |
| FAM221A | green | gray | gray | red | |
| RBM11 | green | yellow | gray | red | |
| FAM213A | green | gray | gray | gray | |
| RHOBTB3 | green | yellow | gray | gray | |
| SLC22A15 | green | gray | gray | gray | |
| NT5C2 | green | yellow | gray | gray | |
| ZNF124 | green | gray | yellow | red | |
| KDM4C | green | green | yellow | red | |
| RALGPS1 | green | yellow | yellow | red | |
| TJP2 | green | yellow | gray | gray | |
| MBOAT2 | green | gray | gray | gray | |
| VEGFA | green | green | gray | gray | |
| ZNF320 | green | gray | gray | gray | |
| EEF1A1 | green | yellow | gray | gray | |
| TOB1 | green | yellow | gray | red | |
| PIK3R1 | green | yellow | gray | gray | |
| GK | green | gray | gray | gray | |
| MET | green | yellow | gray | gray | |
| ITPR2 | green | gray | gray | gray | |
| GRAMD1C | green | gray | gray | red | |
| DDX26B | green | gray | gray | gray | |
| PRRG1 | green | gray | gray | gray | |
| TAF9B | green | green | yellow | gray | |
| ZNF711 | green | gray | gray | gray | |
| ZNF614 | green | yellow | gray | red | |
| TRIM13 | green | yellow | gray | red | |
| ZNF652 | green | yellow | gray | gray | |
| ARID2 | green | yellow | yellow | red | |
| TIPRL | green | green | yellow | gray | |
| FAM92A1 | green | gray | yellow | gray | |
| SQLE | green | green | yellow | gray | |
| LACTB2 | green | green | gray | gray | |
| NUBPL | green | yellow | yellow | red | |
| PDE7A | green | green | yellow | yellow | |
| FAM84B | green | yellow | yellow | gray | |
| YWHAZ | green | green | gray | yellow | |
| PDP1 | green | green | gray | gray | |
| HRSP12 | green | green | yellow | gray | |
| C8orf59 | green | green | yellow | yellow | |

TABLE 5-continued

Genes for identification of subtypes and sub-subtypes

| | CCMS | ccs | CRCA1 | CRCA2 | potential 1 |
|---|---|---|---|---|---|
| OXR1 | green | yellow | yellow | gray | |
| ARFGEF1 | green | green | yellow | yellow | |
| EIF3H | green | yellow | yellow | yellow | |
| AZIN1 | green | gray | yellow | yellow | |
| UTP23 | green | green | yellow | yellow | |
| E2F5 | green | green | yellow | gray | |
| MED30 | green | green | yellow | gray | |
| HCG11 | green | yellow | yellow | yellow | |
| TMEM170B | green | gray | yellow | gray | |
| ZNF439 | green | gray | gray | gray | |
| PIWIL4 | green | yellow | yellow | red | |
| CCDC146 | green | gray | gray | gray | |
| TMEM245 | green | yellow | yellow | gray | |
| TAPT1-AS1 | green | yellow | yellow | gray | |
| ZNF420 | green | yellow | yellow | gray | |
| SMARCE1 | green | yellow | yellow | gray | |
| PLA2R1 | green | yellow | yellow | gray | |
| RBM6 | green | yellow | yellow | gray | |
| DDX17 | green | green | gray | gray | |
| EFHC1 | green | yellow | gray | gray | |
| HERPUD2 | green | green | yellow | yellow | |
| KLHL7 | green | gray | gray | gray | |
| 7-Sep | green | gray | yellow | gray | |
| ENPP5 | green | yellow | yellow | red | |
| SESN3 | green | gray | gray | gray | |
| HNMT | green | gray | gray | red | |
| ZBTB38 | green | yellow | gray | red | |
| CEP68 | green | yellow | yellow | gray | |
| RPL15 | green | yellow | yellow | red | |
| ZNF605 | green | yellow | yellow | red | |
| KCNH8 | green | yellow | yellow | gray | |
| GPCPD1 | green | yellow | yellow | gray | |
| LPCAT2 | green | gray | yellow | yellow | |
| ORMDL1 | green | gray | gray | gray | |
| CLHC1 | green | gray | gray | gray | |
| ASXL2 | green | yellow | gray | yellow | |
| NR1D2 | green | yellow | yellow | gray | |
| TULP4 | green | yellow | yellow | yellow | |
| PAN3-AS1 | green | yellow | yellow | yellow | |
| ZNF141 | green | yellow | yellow | yellow | |
| MLLT4-AS1 | green | yellow | yellow | yellow | |
| ZNF226 | green | gray | gray | red | |
| ZNF302 | green | yellow | gray | red | |
| JPX | green | yellow | yellow | yellow | |
| SKIL | green | yellow | yellow | gray | |
| MBNL2 | green | yellow | yellow | gray | |
| PCMTD1 | green | yellow | gray | gray | |
| TMEM106B | green | yellow | yellow | gray | |
| ATF6 | green | yellow | gray | gray | |
| VAMP4 | green | gray | gray | gray | |
| ANKRD10 | green | yellow | yellow | gray | |
| NFAT5 | green | yellow | gray | yellow | |
| TRAF5 | green | yellow | yellow | gray | |
| ZKSCAN1 | green | yellow | yellow | yellow | |
| RNF170 | green | yellow | yellow | yellow | |
| SRSF6 | green | green | yellow | yellow | |
| RBM26 | green | yellow | yellow | yellow | |
| MIR17HG | green | yellow | yellow | yellow | |
| SLC25A27 | green | yellow | yellow | yellow | |
| AHSA2 | green | gray | gray | gray | |
| PNISR | green | yellow | gray | gray | |
| SOS1 | green | yellow | gray | gray | |
| KIAA0907 | green | yellow | yellow | gray | |
| ATRX | green | gray | yellow | gray | |
| MKLN1 | green | green | yellow | gray | |
| FNBP4 | green | green | gray | gray | |
| LUC7L3 | green | yellow | yellow | gray | |
| OGT | green | green | yellow | gray | |
| MBTD1 | green | yellow | yellow | yellow | |
| SLC25A36 | green | yellow | yellow | yellow | |
| ANKRD10-IT1 | green | yellow | yellow | yellow | |
| COMMD6 | green | yellow | yellow | gray | |
| DNAJC3-AS1 | green | yellow | yellow | yellow | |
| DOCK9 | green | yellow | yellow | yellow | |
| NHLRC3 | green | yellow | yellow | yellow | |
| UGGT2 | green | yellow | yellow | yellow | |

TABLE 5-continued

Genes for identification of subtypes and sub-subtypes

| | CCMS | ccs | CRCA1 | CRCA2 | potential 1 |
|---|---|---|---|---|---|
| DLEU2 | green | yellow | yellow | yellow | |
| ARHGEF7 | green | yellow | yellow | yellow | |
| ZMYM2 | green | yellow | yellow | yellow | |
| ARGLU1 | green | yellow | gray | yellow | |
| N4BP2L2 | green | yellow | yellow | gray | |
| MTRF1 | green | yellow | yellow | gray | |
| UFM1 | green | green | yellow | yellow | |
| COG3 | green | yellow | yellow | yellow | |
| VPS36 | green | yellow | yellow | yellow | |
| SUPT20H | green | yellow | yellow | yellow | |
| MED4 | green | green | yellow | yellow | |
| TUBGCP3 | green | green | yellow | yellow | |
| CDK8 | green | green | yellow | yellow | |
| PDS5B | green | yellow | yellow | yellow | |
| RC3H2 | green | green | gray | yellow | |
| ZNF44 | green | yellow | gray | red | |
| MB21D1 | green | gray | gray | gray | |
| ZNF75A | green | gray | yellow | gray | |
| C9orf64 | green | green | yellow | red | |
| ZNF160 | green | yellow | yellow | yellow | |
| SAMD4B | green | yellow | yellow | gray | |
| FTX | green | yellow | yellow | yellow | |
| TUG1 | green | yellow | yellow | gray | |
| GATAD1 | green | yellow | yellow | yellow | |
| RAP2A | green | yellow | yellow | yellow | |
| INO80D | green | yellow | yellow | red | |
| PHACTR2 | green | yellow | yellow | gray | |
| PRKCI | green | yellow | yellow | yellow | |
| ZNF148 | green | yellow | yellow | yellow | |
| TXNDC9 | green | yellow | yellow | yellow | |
| LTN1 | green | yellow | yellow | red | |
| SLC5A3 | green | yellow | yellow | yellow | |
| ZNF397 | green | yellow | yellow | gray | |
| ZNF573 | green | yellow | yellow | yellow | |
| TMEM19 | green | yellow | gray | red | |
| IL7 | green | gray | gray | gray | |
| NPNT | green | gray | gray | gray | |
| GDPD1 | green | gray | gray | red | |
| RAB2A | green | yellow | gray | gray | |
| INPP4B | green | gray | gray | gray | |
| SCARB2 | green | green | gray | gray | |
| KDM6A | green | green | gray | gray | |
| B3GALNT2 | green | green | yellow | gray | |
| LRIG3 | green | green | gray | gray | |
| SETD9 | green | gray | gray | red | |
| LONRF1 | green | yellow | yellow | gray | |
| EFCAB2 | green | green | gray | gray | |
| NET1 | green | green | gray | gray | |
| BTBD3 | green | gray | gray | gray | |
| LINC00342 | green | gray | gray | gray | |
| CANX | green | green | gray | red | |
| CDC14B | green | yellow | gray | red | |
| SYNJ2BP | green | gray | gray | red | |
| NCOA7 | green | gray | gray | gray | |
| FZD3 | green | gray | gray | gray | |
| VMP1 | green | yellow | gray | gray | |
| ZNF268 | green | yellow | gray | red | |
| SCAPER | green | gray | gray | gray | |
| LRIF1 | green | yellow | yellow | red | |
| ZHX1 | green | yellow | yellow | yellow | |
| GDAP1 | green | gray | gray | gray | |
| MBIP | green | green | gray | gray | |
| KIAA0368 | green | yellow | gray | gray | |
| NAMPT | green | gray | gray | gray | |
| DNAJC3 | green | gray | gray | gray | |
| OTUD3 | green | green | gray | gray | |
| PPM1L | green | gray | gray | gray | |
| MLH3 | green | gray | gray | gray | |
| RAD52 | green | green | gray | red | |
| MSI2 | green | green | yellow | gray | |
| B3GNT2 | green | green | gray | gray | |
| CRYZ | green | gray | gray | gray | |
| MPZL2 | green | green | gray | red | |
| ARMC8 | green | gray | gray | gray | |
| STAMBPL1 | green | green | gray | gray | |
| RPL31 | green | gray | gray | gray | |

TABLE 5-continued

Genes for identification of subtypes and sub-subtypes

| | CCMS | ccs | CRCA1 | CRCA2 | potential 1 |
|---|---|---|---|---|---|
| CNOT6L | green | green | gray | gray | |
| BTC | green | gray | gray | gray | |
| ZNF432 | green | gray | gray | gray | |
| SLC39A10 | green | gray | yellow | gray | |
| ACTR2 | green | green | yellow | yellow | |
| PIGN | green | green | gray | gray | |
| CDK6 | green | green | gray | gray | |
| FAM179B | green | gray | gray | gray | |
| BCKDHB | green | green | gray | red | |
| PELI1 | green | gray | gray | gray | |
| STX6 | green | green | gray | gray | |
| ARHGAP18 | green | green | yellow | red | |
| PGAP1 | green | green | gray | red | |
| ITGA2 | green | gray | gray | gray | |
| ITGA6 | green | green | gray | gray | |
| SNX25 | green | green | gray | gray | |
| ZNF112 | green | yellow | gray | gray | |
| EIF5A2 | green | gray | gray | gray | |
| HMGN5 | green | gray | gray | gray | |
| EIF3F | green | green | gray | gray | |
| DPY19L1 | green | green | gray | gray | |
| PTPLB | green | green | gray | red | |
| C1GALT1 | green | green | gray | gray | |
| RRM2B | green | green | gray | gray | |
| CEP70 | green | gray | gray | gray | |
| ADAM9 | green | green | gray | gray | |
| PDK1 | green | green | gray | gray | |
| GCH1 | green | gray | gray | gray | |
| NUCB2 | green | gray | gray | gray | |
| ASPH | green | gray | gray | gray | |
| G3BP2 | green | green | gray | red | |
| ETNK1 | green | gray | gray | gray | |
| SPTSSA | green | green | gray | gray | |
| ZADH2 | green | green | gray | red | |
| KRAS | green | gray | gray | gray | |
| DYRK2 | green | yellow | gray | gray | |
| CSNK1A1 | green | green | gray | gray | |
| ACBD3 | green | gray | gray | gray | |
| MAP3K5 | green | gray | gray | gray | |
| SGMS2 | green | gray | gray | gray | |
| ANP32E | green | gray | gray | gray | |
| KCTD3 | green | green | gray | gray | |
| TAF1A | green | gray | gray | gray | |
| SGMS1 | green | gray | gray | gray | |
| KATNBL1 | green | gray | gray | gray | |
| CTDSPL2 | green | green | gray | gray | |
| DTWD1 | green | gray | gray | gray | |
| RFX7 | green | green | gray | gray | |
| FEM1B | green | green | gray | gray | |
| HECTD1 | green | gray | gray | gray | |
| SGPP1 | green | green | gray | gray | |
| FAM102B | green | gray | gray | gray | |
| BLZF1 | green | gray | gray | gray | |
| PPP2R5C | green | gray | gray | gray | |
| SPRED1 | green | green | gray | gray | |
| UHMK1 | green | green | gray | gray | |
| RPRD1A | green | green | gray | gray | |
| MDM2 | green | green | gray | gray | |
| RGGT1B | green | green | gray | gray | |
| PRPF39 | green | green | gray | gray | |
| RBM25 | green | green | gray | gray | |
| PCNXL4 | green | gray | gray | gray | |
| EXOC5 | green | green | gray | gray | |
| STYX | green | green | gray | gray | |
| ARHGAP5 | green | green | gray | gray | |
| STRN3 | green | green | gray | gray | |
| IMPACT | green | gray | gray | gray | |
| TMOD3 | green | green | gray | gray | |
| GALNT1 | green | gray | gray | gray | |
| ANKRD12 | green | gray | gray | gray | |
| SOCS6 | green | gray | gray | gray | |
| NAPG | green | green | gray | gray | |
| MIB1 | green | gray | gray | gray | |
| ESCO1 | green | gray | gray | gray | |
| SMCHD1 | green | gray | gray | gray | |
| MAGT1 | green | green | gray | gray | |

TABLE 5-continued

Genes for identification of subtypes and sub-subtypes

| | CCMS | ccs | CRCA1 | CRCA2 | potential 1 |
|---|---|---|---|---|---|
| MORF4L2 | green | yellow | yellow | gray | |
| RP2 | green | green | gray | gray | |
| NXT2 | green | gray | gray | gray | |
| PIGA | green | green | gray | gray | |
| RPS24 | green | green | yellow | red | |
| TPR | green | green | gray | gray | |
| LPGAT1 | green | green | gray | gray | |
| PTAR1 | green | gray | gray | gray | |
| RFX3 | green | green | gray | red | |
| MYO6 | green | green | gray | gray | |
| AP1S2 | green | gray | gray | gray | |
| STK38L | green | yellow | gray | gray | |
| PTPRG | green | green | gray | gray | |
| CAPZA2 | green | green | gray | gray | |
| MYO1B | green | green | gray | gray | |
| STARD4 | green | gray | gray | gray | |
| B4GALT6 | green | gray | gray | gray | |
| GPAM | green | yellow | gray | gray | |
| SEPSECS | green | gray | gray | red | |
| PLA2G12A | green | green | gray | red | |
| CACUL1 | green | green | gray | gray | |
| NBN | green | green | gray | gray | |
| ZCCHC7 | green | yellow | gray | red | |
| GLS | green | yellow | gray | gray | |
| ATP2C1 | green | gray | gray | gray | |
| DDX3X | green | green | gray | gray | |
| SCAMP1 | green | green | gray | gray | |
| NAA15 | green | green | gray | gray | |
| API5 | green | yellow | gray | gray | |
| YME1L1 | green | gray | gray | red | |
| NF1 | green | green | gray | yellow | |
| EML4 | green | green | yellow | red | |
| ADAM1A | green | yellow | yellow | red | |
| SLC38A1 | green | yellow | yellow | red | |
| ATP11B | green | green | gray | red | |
| TBL1XR1 | green | green | gray | gray | |
| FNIP1 | green | green | yellow | red | |
| TTC37 | green | yellow | yellow | red | |
| EEA1 | green | green | yellow | gray | |
| RAD50 | green | yellow | yellow | red | |
| PAWR | green | gray | yellow | yellow | |
| PTBP3 | green | green | gray | gray | |
| SLC30A9 | green | gray | gray | gray | |
| PSIP1 | green | green | gray | gray | |
| SLC4A7 | green | green | gray | gray | |
| NIPBL | green | gray | gray | gray | |
| DNAJC10 | green | gray | gray | gray | |
| CBR4 | green | yellow | gray | red | |
| BOD1L1 | green | gray | gray | gray | |
| YTHDC2 | green | green | gray | gray | |
| MATR3 | green | green | gray | red | |
| PAPD4 | green | gray | gray | gray | |
| TRPM7 | green | green | gray | red | |
| WDR11 | green | yellow | gray | gray | |
| AFF4 | green | gray | gray | gray | |
| C5orf24 | green | green | gray | gray | |
| ATF2 | green | green | gray | gray | |
| ZFYVE16 | green | gray | gray | gray | |
| SP3 | green | yellow | yellow | yellow | |
| TLK1 | green | green | gray | red | |
| SF3B1 | green | gray | gray | gray | |
| UBXN4 | green | green | gray | gray | |
| USP34 | green | yellow | gray | gray | |
| JMJD1C | green | gray | gray | gray | |
| RICTOR | green | green | gray | gray | |
| CLASP2 | green | yellow | gray | gray | |
| TMEM33 | green | green | gray | red | |
| DCAF17 | green | green | gray | yellow | |
| ZNF107 | green | gray | yellow | gray | |
| WDR36 | green | green | gray | gray | |
| GPR180 | green | gray | gray | gray | |
| THAP9-AS1 | green | gray | gray | gray | |
| PPP6R3 | green | green | gray | gray | |
| KIAA1731 | green | gray | gray | gray | |
| ARL5B | green | gray | gray | gray | |
| ZFR | green | green | gray | yellow | |

TABLE 5-continued

Genes for identification of subtypes and sub-subtypes

| | CCMS | ccs | CRCA1 | CRCA2 | potential 1 |
|---|---|---|---|---|---|
| STRN | green | yellow | gray | red | |
| PDZD8 | green | green | gray | gray | |
| CHML | green | gray | gray | gray | |
| ATL2 | green | green | yellow | gray | |
| HOOK1 | green | gray | gray | red | |
| SERBP1 | green | yellow | gray | gray | |
| ANKRD28 | green | gray | gray | red | |
| G2E3 | green | gray | gray | gray | |
| KIF21A | green | gray | gray | gray | |
| UBA6 | green | green | gray | gray | |
| LIN7C | green | green | gray | gray | |
| PDS5A | green | gray | gray | gray | |
| FAR1 | green | green | gray | gray | |
| PRPF38B | green | yellow | gray | gray | |
| MYSM1 | green | green | gray | red | |
| TRMT13 | green | yellow | yellow | red | |
| ZNF644 | green | green | gray | gray | |
| LARP4 | green | green | gray | gray | |
| CEP152 | green | gray | gray | gray | |
| CBX3 | green | green | yellow | yellow | |
| CREBZF | green | green | gray | gray | |
| U2SURP | green | yellow | gray | gray | |
| RIF1 | green | gray | gray | gray | |
| SMC3 | green | gray | gray | gray | |
| TMA16 | green | green | gray | gray | |
| SEC23IP | green | green | gray | gray | |
| BBS7 | green | gray | gray | gray | |
| PAQR3 | green | gray | gray | gray | |
| DAAM1 | green | gray | gray | gray | |
| OIP5-AS1 | green | gray | gray | gray | |
| EIF4A2 | green | yellow | gray | gray | |
| CCSER2 | green | gray | gray | gray | |
| NAB1 | green | green | gray | gray | |
| WSB1 | green | gray | gray | gray | |
| PRKAR1A | green | green | gray | gray | |
| MFAP3 | green | green | gray | gray | |
| POLI | green | gray | gray | gray | |
| CCDC91 | green | yellow | gray | gray | |
| USP32P2 | green | gray | gray | gray | |
| HIPK3 | green | green | gray | gray | |
| TMEM30A | green | green | gray | gray | |
| CPEB4 | green | green | gray | gray | |
| DMXL2 | green | gray | gray | gray | |
| MBNL1 | green | green | gray | gray | |
| REEP3 | green | green | gray | gray | |
| PDE3B | green | green | gray | gray | |
| EXPH5 | green | green | gray | red | |
| ACVR1C | green | gray | gray | red | |
| PPARA | green | yellow | gray | red | |
| NUDT12 | green | gray | gray | red | |
| GCNT1 | green | gray | gray | red | |
| NSUN7 | green | gray | gray | red | |
| MLLT3 | green | green | gray | red | |
| APIP | green | yellow | gray | red | |
| SPAG1 | green | gray | gray | red | |
| TMEM38B | green | green | yellow | red | |
| MPP7 | green | gray | gray | red | |
| IL20RA | green | yellow | yellow | red | |
| SOWAHC | green | yellow | gray | red | |
| TMEM170A | green | green | yellow | yellow | |
| KLF5 | green | gray | yellow | red | |
| DDAH1 | green | green | gray | red | |
| HNF4G | green | green | gray | red | |
| OCLN | green | green | yellow | gray | |
| GIPC2 | green | yellow | gray | red | |
| RNF128 | green | yellow | yellow | red | |
| HSDL2 | green | gray | yellow | red | |
| GOLIM4 | green | green | gray | red | |
| KIF5B | green | green | yellow | yellow | |
| ZBTB18 | green | green | yellow | red | |
| SLC12A2 | green | gray | gray | red | |
| STXBP6 | green | gray | gray | red | |
| IFT74 | green | gray | gray | red | |
| CXADR | green | green | gray | red | |
| ADD3 | green | yellow | gray | red | |
| CERS6 | green | green | gray | red | |

TABLE 5-continued

Genes for identification of subtypes and sub-subtypes

| | CCMS | ccs | CRCA1 | CRCA2 | potential 1 |
|---|---|---|---|---|---|
| SH3YL1 | green | yellow | yellow | red | |
| NEBL | green | yellow | yellow | red | |
| CD46 | green | yellow | yellow | red | |
| TRIM2 | green | green | gray | red | |
| PRRG4 | green | green | gray | red | |
| LGALSL | green | yellow | gray | red | |
| CYP2J2 | green | gray | gray | red | |
| XK | green | gray | gray | red | |
| CMAS | green | gray | gray | red | |
| FAR2 | green | gray | gray | red | |
| NHSL1 | green | yellow | gray | red | |
| PFKFB2 | green | gray | gray | red | |
| FAM110C | green | yellow | gray | red | |
| HSD17B11 | green | gray | gray | red | |
| AKAP7 | green | gray | gray | red | |
| TMEM56 | green | gray | gray | red | |
| KIAA1244 | green | gray | gray | red | |
| RASEF | green | gray | gray | red | |
| DENND1B | green | gray | gray | red | |
| FGD4 | green | green | gray | red | |
| CYP3A5 | green | gray | gray | red | |
| RABGAP1L | green | gray | gray | red | |
| EDEM3 | green | gray | gray | red | |
| RASSF6 | green | gray | gray | red | |
| HIGD1A | green | gray | gray | gray | |
| PTP4A1 | green | green | gray | red | |
| TMEM144 | green | green | gray | red | |
| ITGB6 | green | gray | gray | red | |
| FAM13A | green | gray | gray | red | |
| ANK3 | green | gray | gray | red | |
| SLC40A1 | green | gray | gray | red | |
| CDC42SE2 | green | gray | gray | red | |
| SLC35F5 | green | gray | yellow | red | |
| WASL | green | green | gray | gray | |
| AKAP9 | green | yellow | gray | red | |
| NAPEPLD | green | yellow | gray | red | |
| LAMTOR3 | green | gray | gray | gray | |
| MIER3 | green | green | gray | red | |
| PPP1CB | green | yellow | gray | gray | |
| LNX1 | green | gray | gray | red | |
| MTM1 | green | green | gray | red | |
| MECOM | green | yellow | gray | red | |
| EHF | green | green | gray | red | |
| SLC35B3 | green | gray | gray | red | |
| STL2 | green | gray | gray | red | |
| MOB3B | green | gray | gray | red | |
| ARL14 | green | gray | gray | red | |
| SLC16A9 | green | gray | gray | red | |
| SAMD13 | green | gray | gray | red | |
| NIPAL1 | green | gray | gray | red | |
| SUCLG2 | green | green | gray | red | |
| TDP2 | green | gray | gray | red | |
| LRRC31 | green | gray | gray | red | |
| STX19 | green | gray | gray | red | |
| SLC44A1 | green | yellow | gray | red | |
| KRCC1 | green | gray | gray | red | |
| TRIQK | green | gray | gray | red | |
| TM9SF3 | green | yellow | gray | red | |
| DSGZ | green | gray | gray | red | |
| C4orf33 | green | gray | gray | red | |
| FRYL | green | gray | gray | red | |
| ARFIP1 | green | green | gray | red | |
| USP53 | green | gray | gray | red | |
| TPD52 | green | gray | gray | gray | |
| FAM135A | green | yellow | gray | red | |
| CD164 | green | green | gray | red | |
| KLF3 | green | green | gray | red | |
| ABCD3 | green | gray | gray | red | |
| GALNT3 | green | gray | gray | red | |
| CLCN3 | green | green | gray | red | |
| CDS1 | green | gray | gray | red | |
| GALNT7 | green | green | gray | red | |
| SLC35A3 | green | gray | gray | red | |
| TUBBP5 | brown | green | gray | gray | |
| SIM2 | brown | green | gray | brown | |
| MESP1 | brown | gray | brown | brown | |

TABLE 5-continued

Genes for identification of subtypes and sub-subtypes

| | CCMS | ccs | CRCA1 | CRCA2 | potential 1 |
|---|---|---|---|---|---|
| DHRS2 | brown | gray | brown | brown | |
| RBBP9 | brown | gray | gray | gray | |
| CDS2 | brown | green | gray | gray | |
| TRMT6 | brown | green | gray | brown | |
| ANKEF1 | brown | green | gray | gray | |
| CSNK2A1 | brown | gray | gray | gray | |
| MKKS | brown | green | gray | gray | |
| CRLS1 | brown | gray | gray | gray | |
| SNX5 | brown | green | gray | gray | |
| CRNKL1 | brown | gray | gray | gray | |
| CSRP2BP | brown | gray | gray | gray | |
| KIF16B | brown | gray | gray | gray | |
| MMAA | brown | gray | gray | brown | |
| CXorf57 | brown | brown | gray | gray | |
| LINC00467 | brown | gray | gray | brown | |
| CCND1 | brown | green | gray | brown | |
| GDF15 | brown | green | gray | brown | |
| M6PR | brown | green | gray | gray | |
| EPHB3 | brown | green | gray | brown | |
| CNTNAP2 | brown | gray | brown | brown | |
| LRRC34 | brown | gray | gray | gray | |
| STC2 | brown | gray | gray | gray | |
| HAS3 | brown | gray | brown | brown | |
| AP1S1 | brown | green | gray | brown | |
| DMRT2 | brown | gray | gray | gray | |
| SLC29A1 | brown | green | gray | gray | |
| HMGCS1 | brown | green | brown | brown | |
| INSIG1 | brown | green | brown | brown | |
| ZNF850 | brown | gray | gray | gray | |
| ANKRD22 | brown | green | gray | brown | |
| FAM222A | brown | gray | brown | brown | |
| CHDH | brown | gray | gray | gray | |
| KIF1B | brown | gray | gray | gray | |
| SYBU | brown | gray | gray | gray | |
| COX7B | brown | green | gray | gray | |
| LDLR | brown | brown | gray | gray | |
| GOLT1A | brown | gray | brown | brown | |
| CYB5R2 | brown | gray | gray | gray | |
| KDM3B | brown | green | gray | gray | |
| HS6ST2 | brown | gray | gray | brown | |
| FDFT1 | brown | green | brown | brown | |
| FUOM | brown | gray | gray | brown | |
| ERLIN2 | brown | gray | gray | gray | |
| FAM83B | brown | green | gray | brown | |
| CDH3 | brown | green | brown | brown | |
| CA5BP1 | brown | brown | gray | gray | |
| SLC16A1 | brown | green | brown | brown | |
| MSX1 | brown | gray | brown | brown | |
| PITX2 | brown | gray | gray | brown | |
| KIAA1257 | brown | gray | gray | brown | |
| AP2B1 | brown | gray | brown | brown | |
| DLG3 | brown | green | gray | brown | |
| PROCR | brown | gray | gray | gray | |
| RHPN2 | brown | gray | gray | gray | |
| AIM1 | brown | gray | brown | brown | |
| PREP | brown | green | gray | gray | |
| CRNDE | brown | green | gray | brown | |
| HMGA2 | brown | green | gray | brown | |
| PDK3 | brown | gray | brown | gray | |
| SOX12 | brown | green | brown | brown | |
| ART3 | brown | brown | gray | gray | |
| GRAMD2 | brown | gray | gray | gray | |
| PROM2 | brown | gray | gray | brown | |
| NSF | brown | gray | gray | gray | |
| TNS4 | brown | brown | gray | brown | |
| VSNL1 | brown | gray | brown | brown | |
| SMYD2 | brown | gray | brown | brown | |
| PODXL2 | brown | green | brown | brown | |
| C1orf53 | brown | green | gray | brown | |
| FAHD1 | brown | gray | gray | gray | |
| BAX | brown | green | gray | brown | |
| PHLPP1 | brown | green | gray | brown | |
| HOMER1 | brown | gray | brown | brown | |
| UGGT1 | brown | green | gray | gray | |
| GRHL1 | brown | gray | brown | brown | |
| KISS1R | brown | gray | gray | gray | |

TABLE 5-continued

Genes for identification of subtypes and sub-subtypes

| | CCMS | ccs | CRCA1 | CRCA2 | potential 1 |
|---|---|---|---|---|---|
| 1-Mar | brown | green | gray | brown | |
| SLC27A5 | brown | brown | gray | brown | |
| EPHX4 | brown | gray | gray | gray | |
| NAP1L1 | brown | green | brown | gray | |
| ASB9 | brown | brown | gray | gray | |
| SLC35A2 | brown | green | gray | brown | |
| HSD17B10 | brown | gray | gray | gray | |
| PDHA1 | brown | gray | gray | gray | |
| RNFT2 | brown | brown | brown | gray | |
| DIS3L2 | brown | gray | gray | brown | |
| ACAT1 | brown | brown | brown | gray | |
| OR7E14P | brown | brown | gray | brown | |
| ABHD11 | brown | green | gray | brown | |
| YWHAE | brown | green | gray | brown | |
| CTH | brown | brown | gray | brown | |
| TAF15 | brown | gray | brown | brown | |
| PDCD6 | brown | gray | brown | brown | |
| MANEAL | brown | green | brown | brown | |
| SLCO4A1 | brown | gray | brown | brown | |
| MSL2 | brown | green | gray | brown | |
| NFATC3 | brown | gray | brown | brown | |
| BIK | brown | green | gray | brown | |
| MTMR1 | brown | green | gray | gray | |
| C2CD4A | brown | brown | gray | brown | |
| ENSA | brown | green | brown | gray | |
| DNAJC14 | brown | green | brown | gray | |
| GLS2 | brown | green | gray | brown | |
| CBFB | brown | green | gray | gray | |
| TM7SF3 | brown | green | gray | brown | |
| PRKX | brown | green | gray | gray | |
| GDI2 | brown | green | brown | brown | |
| GSR | brown | green | brown | brown | |
| MFHAS1 | brown | green | brown | brown | |
| PPP2R2A | brown | gray | gray | brown | |
| UBXN8 | brown | gray | brown | brown | |
| AGPAT5 | brown | brown | brown | brown | |
| CNOT7 | brown | green | brown | brown | |
| SF1 | brown | gray | brown | gray | |
| SUMF2 | brown | green | gray | brown | |
| PRCC | brown | green | brown | gray | |
| HYOU1 | brown | green | gray | gray | |
| EIF5A | brown | green | gray | brown | |
| SIN3A | brown | green | gray | brown | |
| GLUD1 | brown | green | gray | gray | |
| RAB8A | brown | green | gray | gray | |
| YWHAH | brown | green | brown | gray | |
| CDK9 | brown | green | gray | brown | |
| DCAKD | brown | green | gray | brown | |
| EXOSC6 | brown | green | gray | brown | |
| PDIA4 | brown | green | brown | brown | |
| PPIB | brown | green | brown | brown | |
| HNRNPL | brown | green | gray | brown | |
| COPG1 | brown | green | gray | brown | |
| STT3A | brown | green | brown | brown | |
| RPN1 | brown | green | gray | brown | |
| SNRNP40 | brown | green | brown | brown | |
| FAM169A | brown | brown | gray | brown | |
| CCDC47 | brown | green | brown | brown | |
| PLEKHG4 | brown | gray | gray | gray | |
| BAG5 | brown | green | gray | brown | |
| F12 | brown | brown | brown | brown | |
| DLGAP1-AS2 | brown | gray | gray | gray | |
| MCCC2 | brown | green | brown | brown | |
| TGIF1 | brown | gray | gray | brown | |
| MLEC | brown | green | brown | gray | |
| THRAP3 | brown | gray | brown | brown | |
| ST7L | brown | gray | gray | gray | |
| HES6 | brown | gray | brown | brown | |
| SMKR1 | brown | green | brown | brown | |
| MEX3D | brown | green | brown | gray | |
| STEAP3 | brown | green | brown | gray | |
| AJUBA | brown | gray | brown | brown | |
| GSTO2 | brown | brown | brown | brown | |
| LIMD1 | brown | green | gray | gray | |
| CDKAL1 | brown | green | gray | brown | |
| ATP5S | brown | gray | gray | brown | |

TABLE 5-continued

Genes for identification of subtypes and sub-subtypes

| | CCMS | ccs | CRCA1 | CRCA2 | potential 1 |
|---|---|---|---|---|---|
| TCTEX1D2 | brown | brown | brown | gray | |
| MPP6 | brown | gray | brown | brown | |
| MOB1A | brown | green | brown | brown | |
| RAB6A | brown | green | brown | brown | |
| PDSS2 | brown | gray | brown | gray | |
| SAFB | brown | green | gray | gray | |
| SLC1A4 | brown | green | brown | gray | |
| TRIB3 | brown | gray | gray | brown | |
| CBX2 | brown | green | brown | brown | |
| ELOVL7 | brown | brown | gray | brown | |
| PSMC2 | brown | green | brown | brown | |
| EIF3B | brown | gray | gray | gray | |
| TRRAP | brown | green | brown | gray | |
| MCM3AP-AS1 | brown | gray | gray | gray | |
| PMAIP1 | brown | gray | gray | brown | |
| C12orf75 | brown | green | gray | brown | |
| PITX1 | brown | green | brown | brown | |
| RPL35A | brown | gray | brown | gray | |
| FBXO41 | brown | green | gray | gray | |
| CRKL | brown | green | brown | brown | |
| AKIRIN1 | brown | green | gray | gray | |
| PPP3R1 | brown | green | brown | brown | |
| CTNNB1 | brown | green | gray | gray | |
| HNRNPH1 | brown | green | gray | brown | |
| CCDC117 | brown | green | brown | brown | |
| TRA2A | brown | gray | gray | brown | |
| KDM1B | brown | gray | brown | brown | |
| IL17RB | brown | brown | brown | brown | |
| SSR1 | brown | green | gray | brown | |
| DHCR24 | brown | brown | brown | brown | |
| PKP4 | brown | green | gray | gray | |
| SLC7A11 | brown | gray | gray | brown | |
| SUMO2 | brown | green | gray | brown | |
| RBBP5 | brown | green | gray | brown | |
| TLCD1 | brown | gray | gray | brown | |
| APOBEC3B | brown | brown | gray | brown | |
| SLC35F2 | brown | brown | brown | brown | |
| BTG3 | brown | gray | brown | brown | |
| SUDS3 | brown | green | gray | gray | |
| NCEH1 | brown | green | gray | brown | |
| RAB15 | brown | green | gray | gray | |
| TMEM52 | brown | green | brown | brown | |
| SLC43A1 | brown | green | brown | brown | |
| AIFM2 | brown | brown | brown | brown | |
| HDAC8 | brown | brown | gray | gray | |
| ZNF239 | brown | gray | brown | gray | |
| RAP1GDS1 | brown | gray | brown | brown | |
| H2AFY | brown | gray | gray | brown | |
| PGK1 | brown | gray | brown | brown | |
| ZNF207 | brown | gray | brown | brown | |
| HPDL | brown | gray | brown | brown | |
| DNAH14 | brown | gray | gray | brown | |
| RAB3IP | brown | brown | gray | gray | |
| PIR | brown | brown | brown | brown | |
| CISD2 | brown | brown | brown | brown | |
| ITCH | brown | green | gray | gray | |
| AP1S3 | brown | brown | brown | brown | |
| ARNTL2 | brown | gray | gray | brown | |
| CCNO | brown | brown | brown | brown | |
| CDC25B | brown | green | brown | brown | |
| TCF3 | brown | green | brown | brown | |
| TRMU | brown | brown | brown | brown | |
| MAT2A | brown | green | gray | brown | |
| THNSL1 | brown | brown | brown | brown | |
| RSL1D1 | brown | brown | gray | brown | |
| TAF11 | brown | green | gray | brown | |
| CD47 | brown | gray | gray | brown | |
| FDXR | brown | green | gray | brown | |
| KBTBD8 | brown | brown | brown | brown | |
| C14orf2 | brown | brown | brown | brown | |
| EMC1 | brown | green | gray | brown | |
| PGD | brown | green | brown | brown | |
| GCHFR | brown | brown | brown | brown | |
| CENPV | brown | green | brown | brown | |
| PCSK9 | brown | brown | brown | brown | |
| FUS | brown | green | brown | brown | |

TABLE 5-continued

Genes for identification of subtypes and sub-subtypes

|  | CCMS | ccs | CRCA1 | CRCA2 | potential 1 |
|---|---|---|---|---|---|
| MAP3K9 | brown | brown | gray | brown | |
| FAM210A | brown | brown | brown | brown | |
| FAM201A | brown | green | brown | brown | |
| CASP2 | brown | green | brown | brown | |
| SHMT1 | brown | green | brown | brown | |
| BAG4 | brown | brown | gray | gray | |
| ZNF511 | brown | brown | brown | brown | |
| SRD5A1 | brown | green | brown | brown | |
| LARP1 | brown | green | brown | gray | |
| NT5DC2 | brown | green | brown | brown | |
| PHKA1 | brown | gray | brown | gray | |
| DESI1 | brown | green | brown | brown | |
| JPH1 | brown | green | brown | brown | |
| CCDC58 | brown | brown | brown | brown | |
| STRIP2 | brown | brown | brown | brown | |
| VDAC1 | brown | green | brown | brown | |
| XPNPEP3 | brown | gray | brown | gray | |
| SEC23B | brown | gray | gray | gray | |
| APOOL | brown | gray | gray | brown | |
| DHCR7 | brown | green | brown | brown | |
| FAM57A | brown | gray | gray | brown | |
| MRPL2 | brown | green | gray | gray | |
| CDV3 | brown | green | brown | brown | |
| KCMF1 | brown | green | brown | brown | |
| PHGDH | brown | brown | gray | brown | |
| MNS1 | brown | brown | brown | brown | |
| PRRT3-AS1 | brown | brown | brown | brown | |
| PIGL | brown | green | brown | brown | |
| EBP | brown | gray | brown | brown | |
| IDH2 | brown | green | brown | brown | |
| RRP7A | brown | brown | brown | brown | |
| TMED2 | brown | green | brown | brown | |
| TFRC | brown | green | brown | brown | |
| SORD | brown | green | brown | brown | |
| AK2 | brown | brown | brown | brown | |
| MORC4 | brown | brown | brown | brown | |
| MYBBP1A | brown | green | gray | brown | |
| HNRNPA1 | brown | green | brown | gray | |
| NANP | brown | gray | gray | gray | |
| FLVCR1 | brown | brown | gray | gray | |
| MCM8 | brown | gray | gray | brown | |
| PRTFDC1 | brown | gray | brown | gray | |
| WEE1 | brown | green | brown | gray | |
| LARS2 | brown | gray | brown | gray | |
| PRMT6 | brown | green | gray | gray | |
| PRPS1 | brown | brown | brown | gray | |
| IDH3A | brown | green | brown | brown | |
| PEX13 | brown | green | gray | brown | |
| DDT | brown | green | brown | brown | |
| NAP1L4 | brown | green | brown | brown | |
| ARG2 | brown | brown | brown | brown | |
| RPP25 | brown | brown | brown | brown | |
| LSM12 | brown | green | brown | brown | |
| GPHN | brown | brown | brown | brown | |
| C5orf22 | brown | green | gray | brown | |
| PSMG4 | brown | gray | gray | brown | |
| APOO | brown | brown | brown | brown | |
| DCAF16 | brown | gray | gray | gray | |
| B9D1 | brown | brown | gray | brown | |
| SNRNP48 | brown | brown | brown | brown | |
| LYPD6 | brown | brown | brown | brown | |
| HN1 | brown | green | brown | brown | |
| UBE2I | brown | gray | brown | brown | |
| BOP1 | brown | green | brown | brown | |
| SLC3A2 | brown | green | gray | brown | |
| FAM216A | brown | brown | brown | brown | |
| ODF2 | brown | green | brown | brown | |
| SCAF4 | brown | gray | brown | gray | |
| NUP62 | brown | green | gray | gray | |
| FH | brown | green | brown | brown | |
| FASN | brown | green | brown | brown | |
| FUT4 | brown | brown | brown | brown | |
| SRPRB | brown | green | brown | brown | |
| NDUFS1 | brown | green | brown | brown | |
| LIPG | brown | green | brown | brown | |
| MRPS25 | brown | gray | brown | brown | |

TABLE 5-continued

Genes for identification of subtypes and sub-subtypes

| | CCMS | ccs | CRCA1 | CRCA2 | potential 1 |
|---|---|---|---|---|---|
| EIF4EBP1 | brown | brown | brown | brown | |
| MRPL52 | brown | green | brown | brown | |
| PRMT5 | brown | gray | brown | brown | |
| PSMB5 | brown | green | brown | brown | |
| THOC6 | brown | green | brown | brown | |
| MIF | brown | green | brown | brown | |
| ENO1 | brown | green | brown | brown | |
| LSM2 | brown | green | brown | brown | |
| GADD45GIP1 | brown | green | brown | brown | |
| MRPS12 | brown | green | brown | brown | |
| TIMM50 | brown | green | brown | brown | |
| ALYREF | brown | green | brown | brown | |
| TOMM22 | brown | green | brown | brown | |
| UBE2M | brown | green | brown | brown | |
| YIF1B | brown | green | brown | brown | |
| ACAT2 | brown | brown | brown | brown | |
| QRSL1 | brown | gray | gray | brown | |
| ANKRD36 | brown | gray | brown | brown | |
| DUT | brown | brown | brown | brown | |
| HBS1L | brown | green | brown | brown | |
| C18orf54 | brown | brown | brown | brown | |
| MTHFD2L | brown | brown | brown | brown | |
| AADAT | brown | brown | brown | brown | |
| CDCA7L | brown | brown | brown | brown | |
| PRKDC | brown | green | gray | brown | |
| PPID | brown | gray | gray | brown | |
| XRCC5 | brown | gray | gray | brown | |
| EIF4E | brown | green | brown | brown | |
| ASNS | brown | brown | brown | brown | |
| SMS | brown | green | brown | brown | |
| NRF1 | brown | gray | brown | brown | |
| BICD1 | brown | gray | gray | brown | |
| SFR1 | brown | green | gray | brown | |
| MRPL44 | brown | green | brown | brown | |
| MTFMT | brown | green | brown | brown | |
| GNPNAT1 | brown | brown | brown | brown | |
| DNAAF2 | brown | green | brown | brown | |
| TMX1 | brown | green | gray | brown | |
| CAND1 | brown | gray | gray | brown | |
| RBBP8 | brown | brown | gray | brown | |
| RNF138 | brown | brown | gray | brown | |
| TIMM21 | brown | brown | gray | brown | |
| CHAC2 | brown | brown | brown | brown | |
| GEMIN2 | brown | brown | brown | brown | |
| CEP76 | brown | brown | brown | brown | |
| SEH1L | brown | brown | brown | brown | |
| GLE1 | brown | green | brown | brown | |
| SFXN1 | brown | brown | brown | brown | |
| SGOL1 | brown | gray | brown | brown | |
| FARSB | brown | gray | brown | brown | |
| SET | brown | gray | brown | brown | |
| TRNT1 | brown | green | brown | brown | |
| PSPH | brown | green | gray | brown | |
| ACLY | brown | green | brown | gray | |
| ORC5 | brown | green | brown | brown | |
| FAM161A | brown | brown | brown | brown | |
| STRAP | brown | gray | brown | brown | |
| AMMECR1 | brown | green | gray | brown | |
| RNASEH2B | brown | gray | gray | gray | |
| CENPJ | brown | brown | gray | brown | |
| DIS3 | brown | gray | gray | brown | |
| NUDT15 | brown | brown | gray | brown | |
| IPO5 | brown | green | gray | brown | |
| BRCA2 | brown | green | gray | brown | |
| MZT1 | brown | brown | gray | brown | |
| EXOSC8 | brown | brown | gray | brown | |
| BORA | brown | brown | gray | brown | |
| CKAP2 | brown | brown | gray | brown | |
| HNRNPC | brown | gray | brown | brown | |
| SLC7A5 | brown | gray | gray | brown | |
| PRPS2 | brown | gray | gray | gray | |
| LRP8 | brown | brown | brown | brown | |
| ZNF165 | brown | brown | gray | brown | |
| C1orf174 | brown | gray | gray | brown | |
| SAP30 | brown | brown | brown | gray | |
| CTNNAL1 | brown | brown | brown | brown | |

TABLE 5-continued

Genes for identification of subtypes and sub-subtypes

| | CCMS | ccs | CRCA1 | CRCA2 | potential 1 |
|---|---|---|---|---|---|
| TKT | brown | green | brown | brown | |
| MRPL50 | brown | green | brown | brown | |
| PSMG1 | brown | green | brown | brown | |
| TMEM237 | brown | gray | brown | gray | |
| NUP50 | brown | green | brown | brown | |
| FGFR1OP | brown | green | brown | brown | |
| SPIN4 | brown | gray | gray | brown | |
| NSMCE4A | brown | green | brown | brown | |
| NUP210 | brown | green | brown | brown | |
| UTP20 | brown | green | brown | brown | |
| WDR4 | brown | brown | brown | brown | |
| NUP62CL | brown | brown | brown | brown | |
| GAS2L3 | brown | brown | brown | brown | |
| SMC1A | brown | brown | gray | brown | |
| SHMT2 | brown | green | brown | brown | |
| HSPA4 | brown | gray | brown | brown | |
| POLR3G | brown | brown | brown | brown | |
| RRP15 | brown | gray | brown | brown | |
| SPATA5L1 | brown | brown | brown | brown | |
| HAUS1 | brown | brown | brown | brown | |
| GPT2 | brown | brown | brown | brown | |
| ADK | brown | green | gray | brown | |
| ELAVL1 | brown | green | brown | brown | |
| HSPA9 | brown | green | brown | brown | |
| TBC1D30 | brown | brown | brown | brown | |
| HNRNPU | brown | gray | gray | brown | |
| PAK6 | brown | green | brown | brown | |
| RMI2 | brown | brown | brown | brown | |
| TUBA4A | brown | green | brown | brown | |
| KIF9 | brown | brown | brown | brown | |
| CHRNA5 | brown | brown | brown | brown | |
| MARS2 | brow | green | brown | brown | |
| WDR34 | brow | brown | brown | brown | |
| PPM1G | brow | green | brown | brown | |
| RBM14 | brow | green | brown | brown | |
| HSPD1 | brow | gray | brown | brown | |
| EED | brow | gray | brown | brown | |
| SUPT16H | brow | green | brown | brown | |
| TMEM97 | brow | green | brown | brown | |
| ILF3 | brow | green | brown | gray | |
| GART | brow | gray | brown | brown | |
| CDC23 | brow | brown | brown | brown | |
| HMGB3 | brow | green | gray | brown | |
| NCBP1 | brow | green | brown | brown | |
| PSMA5 | brow | gray | brown | brown | |
| ESCO2 | brow | brown | brown | brown | |
| WDR76 | brow | brown | brown | brown | |
| CCDC150 | brow | brown | brown | brown | |
| SAC3D1 | brow | brown | brown | brown | |
| METTL21A | brow | gray | brown | brown | |
| C1QBP | brow | green | brown | brown | |
| TSR1 | brow | green | brown | brown | |
| MRS2 | brow | brown | brown | brown | |
| BRI3BP | brow | brown | brown | brown | |
| RNASEH1 | brow | green | brown | brown | |
| SKA2 | brow | brown | brown | brown | |
| PHF19 | brow | brown | brown | brown | |
| NUP98 | brow | green | brown | brown | |
| LSM4 | brow | green | brown | brown | |
| PSAT1 | brow | brown | brown | brown | |
| TYMS | brow | brown | brown | brown | |
| GSPT1 | brow | gray | gray | brown | |
| NUP43 | brow | green | gray | brown | |
| TFDP1 | brow | brown | gray | brown | |
| G3BP1 | brow | green | brown | brown | |
| WDR43 | brow | brown | brown | brown | |
| FANCA | brow | brown | brown | brown | |
| GRPEL2 | brow | green | brown | brown | |
| IQGAP3 | brow | brown | brown | brown | |
| RAD54B | brow | brown | brown | brown | |
| FIGNL1 | brow | green | gray | brown | |
| RAD18 | brow | brown | brown | brown | |
| PRIM2 | brow | green | brown | brown | |
| RCC1 | brow | brown | brown | brown | |
| TFAM | brow | green | gray | brown | |
| BCCIP | brow | brown | brown | brown | |

TABLE 5-continued

Genes for identification of subtypes and sub-subtypes

| | CCMS | ccs | CRCA1 | CRCA2 | potential 1 |
|---|---|---|---|---|---|
| USP1 | brow | brown | brown | brown | |
| GINS1 | brow | brown | gray | brown | |
| PPAT | brow | brown | brown | brow | |
| YEATS4 | brow | green | brown | brow | |
| SRSF1 | brow | green | brown | brow | |
| CACYBP | brow | brown | brown | brow | |
| SNRPD1 | brow | brown | brown | brow | |
| TMPO | brow | green | brown | brow | |
| CDK2 | brow | green | brown | brow | |
| NUDT5 | brow | green | brown | brow | |
| H2AFX | brow | brown | brown | brow | |
| MCM5 | brow | brown | brown | brow | |
| LMNB2 | brow | green | brown | brow | |
| MCM7 | brow | brown | brown | brow | |
| CENPI | brow | brown | gray | brow | |
| DHX9 | brow | gray | brown | brow | |
| TMEM194A | brow | green | brown | brow | |
| CENPH | brow | green | brown | brow | |
| SKA3 | brow | brown | gray | brow | |
| DIAPH3 | brow | brown | gray | brow | |
| RFC3 | brow | brown | gray | brow | |
| RANBP1 | brow | green | brown | brow | |
| GMNN | brow | brown | brown | brow | brow |
| CEP78 | brow | brown | brown | brow | brow |
| C1orf112 | brow | brown | brown | brow | brow |
| DHFR | brow | brown | brown | brow | brow |
| SFPQ | brow | green | brown | brow | brow |
| WHSC1 | brow | green | brown | brow | brow |
| C4orf46 | brow | green | brown | brow | brow |
| ATAD2 | brow | brown | brown | brow | brow |
| CCNE2 | brow | brown | brown | brow | brow |
| CDCA2 | brow | brown | brown | brow | brow |
| CPSF6 | brow | green | brown | brow | brow |
| ZWILCH | brow | brown | brown | brow | brow |
| KIAA1524 | brow | brown | brown | brow | brow |
| MASTL | brow | brown | brown | brow | brow |
| SMC2 | brow | brown | brown | brow | brow |
| KIF14 | brow | brown | brown | brow | brow |
| CENPK | brow | brown | brown | brow | brow |
| CENPE | brow | brown | brown | brow | brow |
| SGOL2 | brow | brown | brown | brow | brow |
| PSRC1 | brow | brown | brown | brow | brow |
| BUB3 | brow | green | brown | brow | brow |
| ARHGAP11 | brow | brown | brown | brow | brow |
| CENPW | brow | brown | brown | brow | brow |
| NASP | brow | brown | brown | brow | brow |
| CDC7 | brow | brown | brown | brow | brow |
| LMNB1 | brow | green | brown | brow | brow |
| SKA1 | brow | brown | brown | brow | brow |
| TIPIN | brow | brow | brow | brow | brow |
| PBK | brow | brow | brow | brow | brow |
| ERCC6L | brow | brow | brow | brow | brow |
| NEIL3 | brow | brow | brow | brow | brow |
| WDHD1 | brow | brow | brow | brow | brow |
| MCM4 | brow | gree | brow | brow | brow |
| MIS18A | brow | brow | brow | brow | brow |
| MCM3 | brow | gree | brow | brow | brow |
| AUNIP | brow | brow | brow | brow | brow |
| UHRF1 | brow | gree | brow | brow | brow |
| CDC25A | brow | gree | brow | brow | brow |
| CENPM | brow | brow | brow | brow | brow |
| CDC6 | brow | gree | brow | brow | brow |
| CDT1 | brow | gree | brow | brow | brow |
| TACC3 | brow | brow | brow | brow | brow |
| GINS2 | brow | brow | brow | brow | brow |
| TK1 | brow | brow | brow | brow | brow |
| E2F7 | brow | brow | brow | brow | brow |
| RAD51 | brow | brow | brow | brow | brow |
| FOXM1 | brow | brow | brow | brow | brow |
| KIF18B | brow | brow | brow | brow | brow |
| PLK1 | brow | brow | brow | brow | brow |
| ORC1 | brow | brow | brow | brow | brow |
| CDCA8 | brow | brow | brow | brow | brow |
| RRM2 | brow | brow | brow | brow | brow |
| KIF20A | brow | brow | brow | brow | brow |
| OIP5 | brow | brow | brow | brow | brow |

TABLE 5-continued

Genes for identification of subtypes and sub-subtypes

| | CCMS | ccs | CRCA1 | CRCA2 | potential 1 |
|---|---|---|---|---|---|
| PRC1 | brow | brow | brow | brow | brow |
| AURKB | brow | brow | brow | brow | brow |
| CCNB1 | brow | brow | brow | brow | brow |
| CDC20 | brow | brow | brow | brow | brow |
| KIF4A | brow | brow | brow | brow | brow |
| CDC45 | brow | brow | brow | brow | brow |
| FEN1 | brow | brow | brow | brow | brow |
| MTFR2 | brow | brow | brow | brow | brow |
| BIRC5 | brow | gree | brow | brow | brow |
| CDCA5 | brow | brow | brow | brow | brow |
| KIF2C | brow | brow | brow | brow | brow |
| MCM10 | brow | brow | brow | brow | brow |
| NCAPH | brow | brow | brow | brow | brow |
| SKP2 | brow | gree | brow | brow | brow |
| CKS2 | brow | brow | brow | brow | brow |
| HELLS | brow | brow | brow | brow | brow |
| BRIP1 | brow | brow | brow | brow | brow |
| POLQ | brow | brow | brow | brow | brow |
| E2F8 | brow | brow | brow | brow | brow |
| PARPBP | brow | brow | brow | brow | brow |
| NDC80 | brow | brown | brow | brow | brow |
| ECT2 | brow | gray | brow | brow | brow |
| KNSTRN | brow | brown | brow | brow | brow |
| MKI67 | brow | brown | brow | brow | brow |
| TOP2A | brow | brown | brow | brow | brow |
| DBF4 | brow | brown | brow | brow | brow |
| EZH2 | brow | brown | brow | brow | brow |
| CASC5 | brow | brown | brow | brow | brow |
| VRK1 | brow | brown | brow | brow | brow |
| DNA2 | brow | brown | brow | brow | brow |
| HMMR | brow | brown | brow | brow | brow |
| HMGB2 | brow | brown | brow | brow | brow |
| FBXO5 | brow | brown | brow | brow | brow |
| KIF18A | brow | brown | brow | brow | brow |
| ASPM | brow | brown | brow | brow | brow |
| CDK1 | brow | brown | brow | brow | brow |
| NUF2 | brow | brown | brow | brow | brow |
| KIF15 | brow | brown | brow | brow | brow |
| CENPN | brow | brown | brow | brow | brow |
| KIAA0101 | brow | brown | brow | brow | brow |
| CHEK1 | brow | brown | brow | brow | brow |
| UBE2T | brow | brown | brow | brow | brow |
| NCAPG2 | brow | brown | brow | brow | brow |
| RAD51AP1 | brow | brown | brow | brow | brow |
| ZNF367 | brow | brown | brow | brow | brow |
| CDKN3 | brow | brown | brow | brow | brow |
| POLE2 | brow | brown | brow | brow | brow |
| DTL | brow | brown | brow | brow | brow |
| STIL | brow | brown | brow | brow | brow |
| ANLN | brow | brown | brow | brow | brow |
| MND1 | brow | brown | brow | brow | brow |
| PLK4 | brow | brown | brow | brow | brow |
| DEPDC1 | brow | brown | brow | brow | brow |
| TTK | brow | brown | brow | brow | brow |
| SPC25 | brow | brown | brow | brow | brow |
| MAD2L1 | brow | brown | brow | brow | brow |
| NCAPG | brow | brown | brow | brow | brow |
| DEPDC1B | brow | brown | brow | brow | brow |
| DLGAP5 | brow | brown | brow | brow | brow |
| KIF11 | brow | brown | brow | brow | brow |
| NEK2 | brow | brown | brow | brow | brow |
| EXO1 | brow | brown | brow | brow | brow |
| CEP55 | brow | brown | brow | brow | brow |
| NUSAP1 | brow | brown | brow | brow | brow |
| CCNA2 | brow | brown | brow | brow | brow |
| KIF23 | brow | brown | brow | brow | brow |
| CCNB2 | brow | brown | brow | brow | brow |
| ZWINT | brown | brown | brown | brown | brown |
| BUB1 | brown | brown | brown | brown | brown |
| BUB1B | brown | brown | brown | brown | brown |
| LMO7 | yellow | yellow | yellow | gray | yellow |
| EFNA3 | yellow | yellow | yellow | red | yellow |
| TMEM187 | yellow | yellow | yellow | gray | yellow |
| LINC00526 | yellow | yellow | green | red | yellow |
| LINC00667 | yellow | yellow | green | red | yellow |
| CAPN3 | yellow | yellow | yellow | red | yellow |

TABLE 5-continued

Genes for identification of subtypes and sub-subtypes

| | CCMS | ccs | CRCA1 | CRCA2 | potential 1 |
|---|---|---|---|---|---|
| MACROD2 | yellow | yellow | yellow | gray | yellow |
| MFAP3L | yellow | gray | gray | gray | yellow |
| UNC93A | yellow | yellow | gray | gray | yellow |
| EYA1 | yellow | yellow | yellow | gray | yellow |
| GRIP1 | yellow | gray | yellow | gray | yellow |
| ARSD | yellow | yellow | green | red | yellow |
| KIAA1211L | yellow | red | yellow | red | yellow |
| THNSL2 | yellow | yellow | yellow | red | yellow |
| UCA1 | yellow | yellow | yellow | yellow | yellow |
| SCML4 | yellow | yellow | gray | red | yellow |
| CCND2 | yellow | gray | green | red | yellow |
| ESRRG | yellow | yellow | yellow | gray | yellow |
| ATF7IP2 | yellow | gray | yellow | gray | yellow |
| ZNF608 | yellow | gray | yellow | yellow | yellow |
| FGFRL1 | yellow | yellow | yellow | yellow | yellow |
| SLC38A4 | yellow | yellow | yellow | red | yellow |
| SLC52A3 | yellow | red | green | red | yellow |
| MAVS | yellow | yellow | green | red | yellow |
| RRBP1 | yellow | gray | yellow | red | yellow |
| PALD1 | yellow | gray | yellow | yellow | yellow |
| SMG7 | yellow | gray | yellow | yellow | yellow |
| CAPN10 | yellow | yellow | yellow | gray | yellow |
| ZNF682 | yellow | yellow | yellow | gray | yellow |
| SMAD6 | yellow | red | yellow | red | yellow |
| NYNRIN | yellow | yellow | green | red | yellow |
| SULT2B1 | yellow | yellow | yellow | red | yellow |
| CAMKK2 | yellow | yellow | yellow | gray | yellow |
| RAB11FIP1 | yellow | gray | gray | red | yellow |
| TMEM139 | yellow | red | green | red | yellow |
| BMP7 | yellow | gray | yellow | gray | yellow |
| GPR115 | yellow | yellow | yellow | gray | yellow |
| PLBD1 | yellow | red | green | red | yellow |
| CYP4F11 | yellow | yellow | green | red | yellow |
| SYK | yellow | yellow | yellow | red | yellow |
| PERP | yellow | gray | yellow | yellow | yellow |
| CAPN13 | yellow | yellow | green | red | yellow |
| L3MBTL4 | yellow | yellow | gray | gray | yellow |
| ELF5 | yellow | yellow | yellow | gray | yellow |
| IGF2R | yellow | gray | yellow | gray | yellow |
| KANSL1 | yellow | yellow | yellow | gray | yellow |
| PRSS33 | yellow | yellow | yellow | yellow | yellow |
| ADRBK2 | yellow | gray | yellow | gray | yellow |
| CLYBL | yellow | yellow | green | red | yellow |
| CRYL1 | yellow | red | yellow | red | yellow |
| GLYR1 | yellow | yellow | yellow | gray | yellow |
| COL9A1 | yellow | yellow | yellow | gray | yellow |
| ZNF503-AS1 | yellow | red | green | red | yellow |
| CHRM3 | yellow | gray | gray | gray | yellow |
| IGF2BP2 | yellow | yellow | yellow | yellow | yellow |
| BEX2 | yellow | yellow | green | gray | yellow |
| SCD | yellow | gray | yellow | gray | yellow |
| PYGB | yellow | yellow | gray | red | yellow |
| SPATC1L | yellow | yellow | gray | gray | yellow |
| MROH1 | yellow | gray | gray | yellow | yellow |
| SLC39A4 | yellow | yellow | yellow | gray | yellow |
| SLC52A2 | yellow | gray | yellow | gray | yellow |
| KRT40 | yellow | yellow | yellow | gray | yellow |
| CYP39A1 | yellow | yellow | green | red | yellow |
| CADPS | yellow | yellow | green | red | yellow |
| PCLO | yellow | yellow | yellow | red | yellow |
| KAZN | yellow | yellow | green | yellow | yellow |
| C6orf223 | yellow | yellow | yellow | gray | yellow |
| PLAG1 | yellow | yellow | gray | gray | yellow |
| ZNF813 | yellow | gray | gray | yellow | yellow |
| TP53TG1 | yellow | yellow | yellow | red | yellow |
| QPCT | yellow | yellow | yellow | red | yellow |
| ZNF827 | yellow | yellow | yellow | red | yellow |
| EIF3C | yellow | yellow | yellow | red | yellow |
| SLC35E4 | yellow | yellow | yellow | red | yellow |
| FAM3B | yellow | yellow | yellow | red | yellow |
| FOXA2 | yellow | gray | yellow | red | yellow |
| CAMK1D | yellow | yellow | green | red | yellow |
| CYFIP2 | yellow | yellow | yellow | red | yellow |
| MYEF2 | yellow | yellow | yellow | gray | yellow |
| ARL11 | yellow | yellow | gray | gray | yellow |
| RNF182 | yellow | yellow | yellow | yellow | yellow |

TABLE 5-continued

Genes for identification of subtypes and sub-subtypes

| | CCMS | ccs | CRCA1 | CRCA2 | potential 1 |
|---|---|---|---|---|---|
| EFNA1 | yellow | gray | green | red | yellow |
| PLEKHB1 | yellow | yellow | yellow | gray | yellow |
| ZFP36L2 | yellow | gray | gray | yellow | yellow |
| SOX9 | yellow | gray | yellow | red | yellow |
| HKDC1 | yellow | red | yellow | gray | yellow |
| RASSF10 | yellow | yellow | yellow | red | yellow |
| RAB11FIP3 | yellow | yellow | yellow | gray | yellow |
| ME3 | yellow | yellow | yellow | red | yellow |
| TNMD | yellow | yellow | yellow | gray | yellow |
| PVR | yellow | gray | yellow | red | yellow |
| ACOX2 | yellow | yellow | green | red | yellow |
| ZNF506 | yellow | yellow | gray | gray | yellow |
| SHISA9 | yellow | yellow | yellow | gray | yellow |
| MCF2L | yellow | yellow | yellow | yellow | yellow |
| RNLS | yellow | yellow | green | red | yellow |
| CCDC170 | yellow | yellow | yellow | red | yellow |
| OXGR1 | yellow | yellow | green | gray | yellow |
| VANGL2 | yellow | yellow | yellow | yellow | yellow |
| FOXQ1 | yellow | gray | yellow | yellow | yellow |
| SLC17A9 | yellow | yellow | yellow | yellow | yellow |
| CGREF1 | yellow | yellow | yellow | yellow | yellow |
| ABCC1 | yellow | gray | yellow | yellow | yellow |
| ABCC4 | yellow | gray | yellow | yellow | yellow |
| ZNF529 | yellow | yellow | yellow | gray | yellow |
| ZNF606 | yellow | yellow | green | red | yellow |
| ZNF502 | yellow | yellow | green | gray | yellow |
| SLC11A2 | yellow | red | yellow | red | yellow |
| SLC13A2 | yellow | yellow | green | red | yellow |
| SH3BP4 | yellow | yellow | yellow | red | yellow |
| MGAT5 | yellow | yellow | yellow | red | yellow |
| MYO10 | yellow | yellow | yellow | red | yellow |
| MPC2 | yellow | gray | green | red | yellow |
| PCTP | yellow | yellow | yellow | red | yellow |
| HDHD1 | yellow | yellow | yellow | red | yellow |
| PNPLA4 | yellow | yellow | gray | red | yellow |
| FCGRT | yellow | yellow | yellow | gray | yellow |
| TMEM176A | yellow | gray | yellow | gray | yellow |
| TMEM176B | yellow | gray | yellow | gray | yellow |
| ABCB1 | yellow | yellow | green | red | yellow |
| JUN | yellow | yellow | yellow | gray | yellow |
| FGFR3 | yellow | yellow | green | red | yellow |
| SDR42E1 | yellow | yellow | green | red | yellow |
| ALDH4A1 | yellow | yellow | yellow | gray | yellow |
| AZGP1 | yellow | yellow | yellow | yellow | yellow |
| RPS15A | yellow | yellow | yellow | gray | yellow |
| DENND1A | yellow | gray | gray | red | yellow |
| SLC22A3 | yellow | yellow | yellow | yellow | yellow |
| CHPT1 | yellow | yellow | yellow | red | yellow |
| C7orf31 | yellow | gray | yellow | red | yellow |
| C11orf1 | yellow | gray | yellow | red | yellow |
| CAMK2N1 | yellow | yellow | yellow | yellow | yellow |
| GPC4 | yellow | gray | yellow | red | yellow |
| CXXC4 | yellow | yellow | yellow | gray | yellow |
| RAB40B | yellow | yellow | gray | red | yellow |
| GSPT2 | yellow | yellow | green | red | yellow |
| ELAVL2 | yellow | yellow | yellow | red | yellow |
| PLAGL1 | yellow | yellow | green | red | yellow |
| SLC35D3 | yellow | yellow | yellow | gray | yellow |
| IP6K2 | yellow | yellow | yellow | red | yellow |
| ZNF814 | yellow | yellow | yellow | red | yellow |
| UNC5CL | yellow | yellow | yellow | yellow | yellow |
| EVPL | yellow | yellow | yellow | red | yellow |
| SLC1A7 | yellow | yellow | yellow | red | yellow |
| ANKH | yellow | gray | yellow | red | yellow |
| KANK1 | yellow | yellow | yellow | red | yellow |
| NEURL1B | yellow | yellow | green | gray | yellow |
| SHH | yellow | yellow | green | red | yellow |
| PAQR5 | yellow | yellow | green | red | yellow |
| AMT | yellow | yellow | green | gray | yellow |
| EFNA2 | yellow | red | green | red | yellow |
| MYO15B | yellow | yellow | green | red | yellow |
| TMC5 | yellow | red | green | red | yellow |
| CGN | yellow | red | green | red | yellow |
| PTK6 | yellow | red | yellow | yellow | yellow |
| CC2D1A | yellow | gray | green | red | yellow |
| MYH14 | yellow | red | green | red | yellow |

TABLE 5-continued

Genes for identification of subtypes and sub-subtypes

| | CCMS | ccs | CRCA1 | CRCA2 | potential 1 |
|---|---|---|---|---|---|
| CYP2S1 | yellow | yellow | green | red | yellow |
| MGAT4B | yellow | gray | green | red | yellow |
| LRP4 | yellow | yellow | green | red | yellow |
| KLC4 | yellow | yellow | yellow | red | yellow |
| ARHGAP44 | yellow | red | gray | red | yellow |
| PCK1 | yellow | red | green | red | yellow |
| SEMA6D | yellow | red | green | red | yellow |
| SEMA6A | yellow | red | green | red | yellow |
| SLC26A2 | yellow | red | green | red | yellow |
| TRPM6 | yellow | yellow | green | red | yellow |
| SORT1 | yellow | gray | green | red | yellow |
| ID1 | yellow | red | green | red | yellow |
| GPR39 | yellow | red | yellow | red | yellow |
| LEFTY1 | yellow | red | green | red | yellow |
| CKB | yellow | red | green | red | yellow |
| PAQR8 | yellow | red | green | red | yellow |
| KIAA1161 | yellow | red | green | red | yellow |
| OLFM4 | yellow | red | green | red | yellow |
| ZSWIM5 | yellow | red | green | red | yellow |
| TOX3 | yellow | gray | green | red | yellow |
| WNK2 | yellow | yellow | green | red | yellow |
| B3GNT3 | yellow | red | green | red | yellow |
| ARHGEF5 | yellow | yellow | yellow | red | yellow |
| CLDN4 | yellow | red | yellow | red | yellow |
| PHYH | yellow | yellow | green | red | yellow |
| PIWIL2 | yellow | red | green | red | yellow |
| ABCC6 | yellow | yellow | yellow | red | yellow |
| CCRL2 | yellow | red | green | red | yellow |
| ACSF2 | yellow | yellow | green | red | yellow |
| TGOLN2 | yellow | yellow | yellow | yellow | yellow |
| HTATIP2 | yellow | gray | yellow | red | yellow |
| H2AFJ | yellow | yellow | yellow | red | yellow |
| CEACAM1 | yellow | red | green | red | yellow |
| SORL1 | yellow | yellow | green | red | yellow |
| RALGAPA2 | yellow | yellow | green | red | yellow |
| KCNQ1 | yellow | yellow | yellow | red | yellow |
| PRR5L | yellow | red | green | red | yellow |
| ARSE | yellow | yellow | green | red | yellow |
| WNK4 | yellow | red | green | red | yellow |
| FAM171A1 | yellow | yellow | green | red | yellow |
| CEACAM6 | yellow | red | green | red | yellow |
| GALNT6 | yellow | yellow | yellow | red | yellow |
| ENPP3 | yellow | yellow | green | red | yellow |
| PTPRD | yellow | yellow | green | red | yellow |
| GRM8 | yellow | yellow | green | red | yellow |
| PTPRK | yellow | yellow | yellow | red | yellow |
| ZNF704 | yellow | yellow | green | red | yellow |
| LY75 | yellow | yellow | yellow | red | yellow |
| SEMA3C | yellow | yellow | green | gray | yellow |
| STK38 | yellow | yellow | yellow | red | yellow |
| IYD | yellow | yellow | green | red | yellow |
| NUDT4 | yellow | yellow | yellow | red | yellow |
| AUTS2 | yellow | yellow | green | red | yellow |
| DIAPH2 | yellow | yellow | green | yellow | yellow |
| PRLR | yellow | yellow | yellow | red | yellow |
| SEMA5A | yellow | yellow | green | red | yellow |
| CTTNBP2 | yellow | yellow | green | red | yellow |
| PLCB4 | yellow | red | yellow | red | yellow |
| REPS2 | yellow | red | green | red | yellow |
| FAM105A | yellow | red | green | red | yellow |
| SATB2-AS1 | yellow | yellow | green | red | yellow |
| PRKAB1 | yellow | red | green | red | yellow |
| HMGCS2 | yellow | red | green | red | yellow |
| CXCL14 | yellow | yellow | green | red | yellow |
| TSPAN12 | yellow | yellow | green | red | yellow |
| HEPH | yellow | red | green | red | yellow |
| POF1B | yellow | red | green | red | yellow |
| LINC00483 | yellow | red | green | red | yellow |
| MOGAT3 | yellow | yellow | green | red | yellow |
| GJB1 | yellow | yellow | green | red | yellow |
| ETS2 | yellow | gray | green | red | yellow |
| CASP6 | yellow | red | green | red | yellow |
| GLCE | yellow | yellow | green | red | yellow |
| PANK1 | yellow | red | green | red | yellow |
| GPX2 | yellow | yellow | yellow | red | yellow |
| ERBB3 | yellow | red | yellow | red | yellow |

TABLE 5-continued

Genes for identification of subtypes and sub-subtypes

| | CCMS | ccs | CRCA1 | CRCA2 | potential 1 |
|---|---|---|---|---|---|
| ST14 | yellow | red | green | red | yellow |
| PPARG | yellow | red | green | red | yellow |
| ILDR1 | yellow | red | green | red | yellow |
| SPINK1 | yellow | red | green | red | yellow |
| SGK2 | yellow | yellow | green | red | yellow |
| ACOX1 | yellow | yellow | green | red | yellow |
| MYO1D | yellow | gray | green | red | yellow |
| KALRN | yellow | red | green | red | yellow |
| MUC12 | yellow | yellow | green | red | yellow |
| KRT20 | yellow | red | green | red | yellow |
| PIGZ | yellow | red | green | red | yellow |
| NAT2 | yellow | red | green | red | yellow |
| FAM134B | yellow | red | green | red | yellow |
| PBLD | yellow | red | green | red | yellow |
| SELENBP1 | yellow | red | green | red | yellow |
| PLEKHG6 | yellow | yellow | green | red | yellow |
| TINAG | yellow | yellow | green | red | yellow |
| SOWAHA | yellow | yellow | green | red | yellow |
| CEBPA | yellow | yellow | green | red | yellow |
| TFCP2L1 | yellow | yellow | green | red | yellow |
| ELF3 | yellow | red | green | red | yellow |
| EPS8L3 | yellow | red | green | red | yellow |
| CDH17 | yellow | red | green | red | yellow |
| CEACAM5 | yellow | red | green | red | yellow |
| PRSS8 | yellow | red | green | red | yellow |
| TMPRSS2 | yellow | red | green | red | yellow |
| A1CF | yellow | yellow | green | red | yellow |
| MUC20 | yellow | yellow | green | red | yellow |
| NOX1 | yellow | red | green | red | yellow |
| TRABD2A | yellow | yellow | green | red | yellow |
| CDH1 | yellow | gray | green | red | yellow |
| CLDN3 | yellow | red | green | red | yellow |
| DAPK2 | yellow | yellow | green | red | yellow |
| SHROOM1 | yellow | yellow | green | red | yellow |
| MEP1A | yellow | red | green | red | yellow |
| OVOL1 | yellow | yellow | green | red | yellow |
| ISX | yellow | yellow | green | red | yellow |
| ACE2 | yellow | yellow | yellow | red | yellow |
| SLC39A5 | yellow | yellow | green | red | yellow |
| SLC3A1 | yellow | yellow | green | red | yellow |
| CDHR1 | yellow | yellow | green | red | yellow |
| PPP1R14C | yellow | yellow | green | red | yellow |
| SATB2 | yellow | yellow | green | red | yellow |
| ACSL5 | yellow | yellow | green | red | yellow |
| VIL1 | yellow | yellow | green | red | yellow |
| DDC | yellow | yellow | green | red | yellow |
| CFTR | yellow | yellow | green | red | yellow |
| AIFM3 | yellow | yellow | green | red | yellow |
| SLC26A3 | yellow | red | green | red | yellow |
| EPB41L4B | yellow | yellow | green | red | yellow |
| LRRC19 | yellow | red | green | red | yellow |
| FABP1 | yellow | red | green | red | yellow |
| C10orf99 | yellow | red | green | red | yellow |
| PPP1R14D | yellow | yellow | green | red | yellow |
| NR1I2 | yellow | yellow | green | red | yellow |
| PRR15 | yellow | yellow | green | red | yellow |
| CDX2 | yellow | yellow | green | red | yellow |
| IHH | yellow | yellow | green | red | yellow |
| FAM84A | yellow | red | green | red | yellow |
| ATP10B | yellow | yellow | green | red | yellow |
| GPR160 | yellow | yellow | green | red | yellow |
| GUCY2C | yellow | yellow | green | red | yellow |
| SCARB1 | yellow | yellow | yellow | red | yellow |
| ZBED3 | yellow | gray | yellow | gray | yellow |
| TMEM63A | yellow | gray | yellow | yellow | yellow |
| ATAT1 | yellow | yellow | yellow | yellow | yellow |
| PTP4A3 | yellow | yellow | yellow | yellow | yellow |
| ABHD12 | yellow | yellow | yellow | yellow | yellow |
| HNF4A | yellow | yellow | yellow | gray | yellow |
| ATP7B | yellow | yellow | yellow | red | yellow |
| GRTP1 | yellow | red | yellow | gray | yellow |
| STK24 | yellow | gray | yellow | yellow | yellow |
| CELSR3 | yellow | yellow | yellow | yellow | yellow |
| TBC1D5 | yellow | yellow | yellow | gray | yellow |
| KLHDC10 | yellow | gray | yellow | yellow | yellow |
| C20orf196 | yellow | yellow | green | red | yellow |

TABLE 5-continued

Genes for identification of subtypes and sub-subtypes

| | CCMS | ccs | CRCA1 | CRCA2 | potential 1 |
|---|---|---|---|---|---|
| LINC00525 | yellow | yellow | yellow | yellow | yellow |
| DNAJC15 | yellow | yellow | yellow | yellow | yellow |
| FAM210B | yellow | yellow | yellow | yellow | yellow |
| RPS6KA6 | yellow | yellow | yellow | red | yellow |
| CCDC113 | yellow | yellow | yellow | red | yellow |
| GYLTL1B | yellow | yellow | yellow | gray | yellow |
| PROSER2 | yellow | yellow | yellow | red | yellow |
| SNTB1 | yellow | gray | yellow | yellow | yellow |
| SLC2A4RG | yellow | yellow | yellow | yellow | yellow |
| NOTCH1 | yellow | yellow | yellow | red | yellow |
| SOX4 | yellow | yellow | yellow | yellow | yellow |
| CSNK1E | yellow | gray | yellow | gray | yellow |
| ZNF503 | yellow | gray | yellow | gray | yellow |
| SLC6A6 | yellow | gray | yellow | gray | yellow |
| FARP1 | yellow | yellow | yellow | gray | yellow |
| PMEPA1 | yellow | yellow | yellow | gray | yellow |
| LGR5 | yellow | gray | yellow | red | yellow |
| STX3 | yellow | gray | green | red | yellow |
| WIF1 | yellow | yellow | yellow | yellow | yellow |
| HIBADH | yellow | gray | yellow | yellow | yellow |
| MED1 | yellow | gray | yellow | yellow | yellow |
| CLDN1 | yellow | yellow | yellow | yellow | yellow |
| ZNF280B | yellow | yellow | yellow | red | yellow |
| AOAH | yellow | yellow | yellow | gray | yellow |
| RNF157 | yellow | yellow | yellow | red | yellow |
| CKMT2 | yellow | yellow | yellow | red | yellow |
| NKD2 | yellow | yellow | yellow | gray | yellow |
| ATP6V1C2 | yellow | yellow | yellow | red | yellow |
| HILPDA | yellow | gray | yellow | gray | yellow |
| SLC2A12 | yellow | yellow | yellow | yellow | yellow |
| ZNF93 | yellow | yellow | gray | gray | yellow |
| FABP6 | yellow | yellow | yellow | red | yellow |
| PNLIPRP2 | yellow | yellow | green | red | yellow |
| ZNF681 | yellow | yellow | gray | red | yellow |
| PPDPF | yellow | yellow | yellow | yellow | yellow |
| CYB5B | yellow | yellow | yellow | yellow | yellow |
| CBX5 | yellow | yellow | yellow | red | yellow |
| REEP1 | yellow | yellow | yellow | gray | yellow |
| ZBTB10 | yellow | yellow | green | yellow | yellow |
| TG | yellow | yellow | yellow | red | yellow |
| ADCY3 | yellow | yellow | gray | yellow | yellow |
| DIO3OS | yellow | yellow | green | yellow | yellow |
| LRRC36 | yellow | yellow | yellow | gray | yellow |
| AGT | yellow | yellow | green | gray | yellow |
| CYP4F2 | yellow | yellow | yellow | yellow | yellow |
| CYP4F3 | yellow | yellow | yellow | yellow | yellow |
| HENMT1 | yellow | yellow | yellow | red | yellow |
| NUDT7 | yellow | yellow | green | red | yellow |
| ZC3H12B | yellow | yellow | yellow | yellow | yellow |
| FREM2 | yellow | yellow | yellow | yellow | yellow |
| DNAJC6 | yellow | yellow | yellow | yellow | yellow |
| ESPN | yellow | yellow | green | yellow | yellow |
| IFNLR1 | yellow | yellow | yellow | red | yellow |
| ANXA9 | yellow | yellow | yellow | yellow | yellow |
| ENTPD6 | yellow | yellow | yellow | red | yellow |
| L3MBTL1 | yellow | yellow | yellow | gray | yellow |
| ZNF785 | yellow | yellow | yellow | yellow | yellow |
| SPIN3 | yellow | yellow | yellow | yellow | yellow |
| MCF2L-AS1 | yellow | yellow | yellow | red | yellow |
| TDRKH | yellow | yellow | yellow | yellow | yellow |
| COBLL1 | yellow | yellow | yellow | yellow | yellow |
| KCNK5 | yellow | yellow | green | red | yellow |
| PHACTR3 | yellow | yellow | yellow | yellow | yellow |
| ST6GAL1 | yellow | gray | yellow | red | yellow |
| MYRIP | yellow | yellow | green | red | yellow |
| BEND7 | yellow | yellow | yellow | red | yellow |
| DBI | yellow | gray | yellow | red | yellow |
| FGFR4 | yellow | yellow | yellow | red | yellow |
| AGMAT | yellow | yellow | yellow | red | yellow |
| RAB11FIP4 | yellow | gray | yellow | red | yellow |
| GNL3L | yellow | yellow | yellow | yellow | yellow |
| FHDC1 | yellow | yellow | green | red | yellow |
| PPM1H | yellow | yellow | yellow | red | yellow |
| EPHB2 | yellow | yellow | green | red | yellow |
| ZNF703 | yellow | yellow | yellow | red | yellow |
| NCR3LG1 | yellow | yellow | yellow | yellow | yellow |

TABLE 5-continued

Genes for identification of subtypes and sub-subtypes

| | CCMS | ccs | CRCA1 | CRCA2 | potential 1 |
|---|---|---|---|---|---|
| MIPEP | yellow | yellow | yellow | gray | yellow |
| SLC7A1 | yellow | gray | yellow | gray | yellow |
| PDP2 | yellow | yellow | yellow | red | yellow |
| TFDP2 | yellow | yellow | yellow | yellow | yellow |
| TUFT1 | yellow | yellow | yellow | red | yellow |
| FERMT1 | yellow | yellow | yellow | red | yellow |
| ATP11A | yellow | gray | yellow | yellow | yellow |
| GTF3A | yellow | yellow | yellow | yellow | yellow |
| NUFIP1 | yellow | yellow | yellow | yellow | yellow |
| RFXAP | yellow | yellow | yellow | yellow | yellow |
| DDX18 | yellow | gray | yellow | gray | yellow |
| FSD1L | yellow | yellow | yellow | red | yellow |
| PIN4 | yellow | yellow | yellow | gray | yellow |
| PUS10 | yellow | yellow | yellow | yellow | yellow |
| PHOSPHO2 | yellow | yellow | yellow | red | yellow |
| TMEM192 | yellow | yellow | yellow | red | yellow |
| MACC1 | yellow | yellow | yellow | yellow | yellow |
| ARMCX5 | yellow | yellow | yellow | yellow | yellow |
| OFD1 | yellow | yellow | yellow | yellow | yellow |
| USP9X | yellow | yellow | yellow | yellow | yellow |
| CLCN5 | yellow | yellow | yellow | yellow | yellow |
| EIF2S3 | yellow | gray | yellow | red | yellow |
| TAB3 | yellow | yellow | yellow | yellow | yellow |
| EIF1AX | yellow | gray | yellow | yellow | yellow |
| MED14 | yellow | yellow | yellow | red | yellow |
| POLA1 | yellow | gray | yellow | yellow | yellow |
| TXLNG | yellow | yellow | yellow | yellow | yellow |
| SCML1 | yellow | yellow | yellow | yellow | yellow |
| FAM122B | yellow | yellow | yellow | yellow | yellow |
| BRCC3 | yellow | yellow | yellow | red | yellow |
| THOC2 | yellow | gray | yellow | yellow | yellow |
| MEST | yellow | yellow | yellow | yellow | yellow |
| DUS4L | yellow | yellow | yellow | yellow | yellow |
| NAA38 | yellow | gray | gray | gray | yellow |
| FAM60A | yellow | gray | yellow | red | yellow |
| EPB41L5 | yellow | yellow | yellow | red | yellow |
| ZDHHC23 | yellow | yellow | green | red | yellow |
| GPSM2 | yellow | yellow | yellow | red | yellow |
| CDCA7 | yellow | yellow | yellow | red | yellow |
| NFE2L3 | yellow | yellow | yellow | red | yellow |
| SRPK1 | yellow | gray | yellow | red | yellow |
| MYB | yellow | red | green | red | yellow |
| STRBP | yellow | yellow | yellow | red | yellow |
| CLDN15 | yellow | yellow | yellow | yellow | yellow |
| ERP27 | yellow | yellow | yellow | red | yellow |
| APCDD1 | yellow | yellow | yellow | yellow | yellow |
| CAB39L | yellow | yellow | yellow | gray | yellow |
| SYNE4 | yellow | yellow | gray | yellow | yellow |
| IRF2BP2 | yellow | gray | yellow | yellow | yellow |
| PTPRO | yellow | yellow | yellow | red | yellow |
| LRRC2 | yellow | yellow | yellow | yellow | yellow |
| BCL11A | yellow | yellow | yellow | red | yellow |
| FOXO3 | yellow | yellow | yellow | gray | yellow |
| SESN1 | yellow | yellow | yellow | yellow | yellow |
| DGAT2 | yellow | yellow | yellow | yellow | yellow |
| COL9A3 | yellow | yellow | yellow | gray | yellow |
| USP7 | yellow | yellow | yellow | yellow | yellow |
| C6orf123 | yellow | yellow | yellow | yellow | yellow |
| LAPTM4B | yellow | yellow | yellow | yellow | yellow |
| ZFAS1 | yellow | yellow | yellow | yellow | yellow |
| FER1L4 | yellow | yellow | yellow | yellow | yellow |
| MAP1LC3A | yellow | yellow | yellow | gray | yellow |
| CTSA | yellow | yellow | yellow | yellow | yellow |
| SDC4 | yellow | yellow | yellow | yellow | yellow |
| GPR56 | yellow | yellow | yellow | yellow | yellow |
| CACNA1D | yellow | yellow | yellow | yellow | yellow |
| EPDR1 | yellow | yellow | yellow | yellow | yellow |
| PROX1 | yellow | yellow | yellow | yellow | yellow |
| DACH1 | yellow | yellow | yellow | red | yellow |
| DUSP18 | yellow | yellow | yellow | red | yellow |
| PTCH1 | yellow | yellow | yellow | red | yellow |
| RLN2 | yellow | yellow | yellow | yellow | yellow |
| BCL2L1 | yellow | yellow | yellow | gray | yellow |
| PRDX5 | yellow | yellow | green | red | yellow |
| SHANK2 | yellow | yellow | yellow | yellow | yellow |
| KHDRBS3 | yellow | yellow | yellow | yellow | yellow |

TABLE 5-continued

Genes for identification of subtypes and sub-subtypes

| | CCMS | ccs | CRCA1 | CRCA2 | potential 1 |
|---|---|---|---|---|---|
| GYG2 | yellow | yellow | yellow | yellow | yellow |
| IL22RA1 | yellow | yellow | yellow | yellow | yellow |
| PAH | yellow | yellow | yellow | yellow | yellow |
| DUSP16 | yellow | yellow | green | red | yellow |
| NANO | yellow | gray | yellow | yellow | yellow |
| NCOA3 | yellow | yellow | yellow | yellow | yellow |
| ETV4 | yellow | yellow | yellow | yellow | yellow |
| SPIRE2 | yellow | yellow | yellow | yellow | yellow |
| ANO9 | yellow | yellow | yellow | yellow | yellow |
| ENGASE | yellow | yellow | yellow | yellow | yellow |
| GAS2 | yellow | yellow | yellow | yellow | yellow |
| PIPOX | yellow | yellow | yellow | yellow | yellow |
| CYP2B6 | yellow | yellow | green | red | yellow |
| ELMO2 | yellow | yellow | yellow | yellow | yellow |
| NKD1 | yellow | yellow | yellow | yellow | yellow |
| DPEP1 | yellow | yellow | yellow | red | yellow |
| ZNRF3 | yellow | yellow | yellow | red | yellow |
| C7orf13 | yellow | yellow | yellow | yellow | yellow |
| SLC7A6 | yellow | yellow | yellow | yellow | yellow |
| TLE2 | yellow | yellow | yellow | yellow | yellow |
| EMILIN3 | yellow | yellow | yellow | yellow | yellow |
| EPB41L1 | yellow | yellow | yellow | yellow | yellow |
| MAP7D2 | yellow | yellow | yellow | yellow | yellow |
| REPIN1 | yellow | yellow | yellow | red | yellow |
| PM20D2 | yellow | yellow | yellow | yellow | yellow |
| CRCP | yellow | gray | yellow | yellow | yellow |
| GGH | yellow | yellow | yellow | red | yellow |
| ABAT | yellow | yellow | yellow | yellow | yellow |
| C11orf95 | yellow | yellow | yellow | yellow | yellow |
| ZNF217 | yellow | yellow | yellow | yellow | yellow |
| CHN2 | yellow | yellow | yellow | yellow | yellow |
| GSE1 | yellow | yellow | yellow | yellow | yellow |
| RBP2 | yellow | yellow | yellow | yellow | yellow |
| SHROOM2 | yellow | yellow | yellow | yellow | yellow |
| AKAP1 | yellow | yellow | yellow | yellow | yellow |
| STOX1 | yellow | yellow | yellow | yellow | yellow |
| SLC19A3 | yellow | yellow | yellow | gray | yellow |
| ACSL6 | yellow | yellow | yellow | yellow | yellow |
| CASK | yellow | gray | yellow | yellow | yellow |
| CTPS2 | yellow | yellow | yellow | yellow | yellow |
| HSPH1 | yellow | yellow | yellow | yellow | yellow |
| GTF2F2 | yellow | gray | yellow | yellow | yellow |
| NDFIP2 | yellow | yellow | yellow | yellow | yellow |
| TMTC4 | yellow | yellow | yellow | yellow | yellow |
| UCHL3 | yellow | yellow | yellow | gray | yellow |
| SPATA13 | yellow | yellow | yellow | yellow | yellow |
| NEK3 | yellow | yellow | yellow | yellow | yellow |
| PROSER1 | yellow | yellow | yellow | yellow | yellow |
| WDR35 | yellow | yellow | yellow | yellow | yellow |
| ZNF514 | yellow | yellow | yellow | yellow | yellow |
| CBFA2T2 | yellow | yellow | yellow | yellow | yellow |
| ZMYND8 | yellow | yellow | yellow | yellow | yellow |
| CHD6 | yello | yellow | yello | yellow | yello |
| PABPC1L | yello | yellow | yello | yellow | yello |
| RAB22A | yello | yellow | yello | yellow | yello |
| LINC00657 | yello | yellow | yello | yellow | yello |
| RBM39 | yello | yellow | yello | yellow | yello |
| ARFGEF2 | yello | yellow | yello | yellow | yello |
| PCMTD2 | yello | yellow | yello | yellow | yello |
| STX16 | yello | gray | yello | yellow | yello |
| EREG | yello | yellow | yello | yellow | yello |
| GGT7 | yello | yellow | yello | yellow | yello |
| PARD6B | yello | yellow | yello | yellow | yello |
| TOP1 | yello | gray | yello | yellow | yello |
| YAE1D1 | yello | yellow | yello | yellow | yello |
| MYC | yello | yellow | yello | yellow | yello |
| TNNC2 | yello | yellow | yello | yellow | yello |
| CEL | yello | yellow | yello | yellow | yello |
| CELP | yello | yellow | yello | yellow | yello |
| ZDHHC9 | yello | yellow | yello | yellow | yello |
| HUNK | yello | yellow | yello | red | yello |
| AXIN2 | yello | yellow | yello | red | yello |
| ASCL2 | yello | yellow | yello | red | yello |
| RNF43 | yello | yellow | yello | red | yello |
| QPRT | yello | yellow | yello | yellow | yello |
| TSPAN6 | yello | yellow | gree | red | yello |

TABLE 5-continued

Genes for identification of subtypes and sub-subtypes

| | CCMS | ccs | CRCA1 | CRCA2 | potential 1 |
|---|---|---|---|---|---|
| VAV3 | yello | yellow | gree | red | yello |
| NEU1 | yello | yellow | yello | yellow | yello |
| C8orf33 | yello | yellow | yello | yellow | yello |
| PLA2G12B | yello | yellow | yello | yellow | yello |
| GTF2IRD1 | yello | yellow | yello | yellow | yello |
| POFUT1 | yello | yellow | yello | yellow | yello |
| KRT23 | yello | yellow | yello | yellow | yello |
| ARID3A | yello | yellow | yello | yellow | yello |
| CABLES2 | yello | yellow | yello | yellow | yello |
| SERINC3 | yello | yellow | yello | yellow | yello |
| GNG4 | yello | yellow | yello | yellow | yello |
| GPR143 | yello | yellow | yello | yellow | yello |
| SPATA2 | yello | yellow | yello | yellow | yello |
| MOCS3 | yello | gray | yello | yellow | yello |
| NDRG3 | yello | gray | yello | yellow | yello |
| TTPAL | yello | yellow | yello | yellow | yello |
| ATP9A | yello | yellow | yello | yellow | yello |
| CHMP4B | yello | yellow | yello | yellow | yello |
| COMMD7 | yello | yellow | yello | yellow | yello |
| EIF2S2 | yello | yellow | yello | yellow | yello |
| TCFL5 | yello | yellow | yello | yellow | yello |
| DSN1 | yello | gray | yello | gray | yello |
| SLMO2 | yello | yellow | yello | yellow | yello |
| CSE1L | yellow | yellow | yellow | yellow | yellow |
| DPM1 | yellow | yellow | yellow | yellow | yellow |
| PFDN4 | yellow | yellow | yellow | yellow | yellow |
| ACOT8 | yellow | yellow | yellow | yellow | yellow |
| DHX35 | yellow | yellow | yellow | yellow | yellow |
| PXMP4 | yellow | yellow | yellow | yellow | yellow |
| AHCY | yellow | yellow | yellow | yellow | yellow |
| MRGBP | yellow | gray | yellow | gray | yellow |
| AURKA | yellow | gray | yellow | gray | yellow |
| TPX2 | yellow | gray | yellow | gray | yellow |
| UBE2C | yellow | gray | yellow | gray | yellow |
| SLC5A6 | yellow | yellow | yellow | yellow | yellow |
| FITM2 | yellow | yellow | yellow | yellow | yellow |
| TM9SF4 | yellow | yellow | yellow | yellow | yellow |
| UCKL1 | yellow | yellow | yellow | yellow | yellow |
| DNTTIP1 | yellow | yellow | yellow | yellow | yellow |
| RNF114 | yellow | yellow | yellow | yellow | yellow |
| GSS | yellow | yellow | yellow | yellow | yellow |
| SCAND1 | yellow | yellow | yellow | yellow | yellow |
| TP53RK | yellow | yellow | yellow | yellow | yellow |
| ADRM1 | yellow | yellow | yellow | yellow | yellow |
| TOMM34 | yellow | yellow | yellow | yellow | yellow |
| RPS21 | yellow | yellow | yellow | yellow | yellow |
| CPNE1 | yellow | yellow | yellow | yellow | yellow |
| ASXL1 | yellow | yellow | yellow | yellow | yellow |
| ROMO1 | yellow | yellow | yellow | yellow | yellow |
| RAE1 | yellow | yellow | yellow | yellow | yellow |
| VAPB | yellow | yellow | yellow | yellow | yellow |
| ERGIC3 | yellow | yellow | yellow | yellow | yellow |
| PLAGL2 | yellow | yellow | yellow | yellow | yellow |
| DYNLRB1 | yellow | yellow | yellow | yellow | yellow |
| TTI1 | yellow | yellow | yellow | yellow | yellow |
| PRPF6 | yellow | yellow | yellow | yellow | yellow |
| YTHDF1 | yellow | yellow | yellow | yellow | yellow |
| DDX27 | yellow | yellow | yellow | yellow | yellow |
| EIF6 | yellow | yellow | yellow | yellow | yellow |
| PIGU | yellow | yellow | yellow | yellow | yellow |
| NELFCD | yellow | yellow | yellow | yellow | yellow |
| CTNNBL1 | yellow | yellow | yellow | yellow | yellow |
| PSMA7 | yellow | yellow | yellow | yellow | yellow |
| KIF3B | yellow | yellow | yellow | yellow | yellow |
| FAM217B | yellow | yellow | yellow | yellow | yellow |
| PPP1R3D | yellow | yellow | yellow | yellow | yellow |
| DIDO1 | yellow | yellow | yellow | yellow | yellow |
| STK4 | yellow | yellow | yellow | yellow | yellow |
| YWHAB | yellow | yellow | yellow | yellow | yellow |
| LPAR3 | red | gray | gray | gray | red |
| PF4 | red | gray | gray | red | red |
| SDC1 | red | gray | green | red | red |
| TMEM2 | red | gray | red | red | red |
| IGFBP2 | red | gray | green | gray | red |
| FOXA1 | red | gray | gray | gray | red |
| RRN3P1 | red | gray | gray | red | red |

TABLE 5-continued

Genes for identification of subtypes and sub-subtypes

| | CCMS | ccs | CRCA1 | CRCA2 | potential 1 |
|---|---|---|---|---|---|
| CEACAM8 | red | gray | green | red | red |
| GIF | red | magenta | green | red | red |
| C1orf116 | red | magenta | green | red | red |
| RELL1 | red | gray | gray | red | red |
| UBXN10 | red | gray | gray | red | red |
| ZFP3 | red | gray | green | red | red |
| SLC35G1 | red | gray | gray | gray | red |
| HES1 | red | gray | green | gray | red |
| FAIM2 | red | gray | gray | gray | red |
| KCNN4 | red | gray | green | red | red |
| GAL3ST1 | red | red | green | red | red |
| METTL7B | red | red | green | red | red |
| SLC9A3R1 | red | gray | gray | red | red |
| COBL | red | gray | gray | gray | red |
| LTK | red | gray | gray | gray | red |
| ENTPD2 | red | gray | green | gray | red |
| MAP3K13 | red | gray | green | gray | red |
| TM4SF20 | red | gray | gray | red | red |
| CCL24 | red | gray | gray | red | red |
| CHST4 | red | gray | gray | gray | red |
| EGF | red | red | gray | gray | red |
| DEFA5 | red | greenyellow | green | red | red |
| DEFA6 | red | greenyellow | green | red | red |
| LYPD6B | red | gray | gray | gray | red |
| DNAJC12 | red | gray | gray | gray | red |
| PCSK1 | red | magenta | gray | gray | red |
| NTN4 | red | greenyellow | gray | gray | red |
| SMAD9 | red | gray | green | gray | red |
| GPR128 | red | gray | gray | gray | red |
| PCCA | red | magenta | green | red | red |
| COL4A5 | red | greenyellow | green | gray | red |
| CASZ1 | red | gray | red | gray | red |
| OTC | red | gray | green | gray | red |
| REG3A | red | magenta | red | gray | red |
| REG1P | red | magenta | red | gray | red |
| REG1A | red | magenta | red | gray | red |
| REG1B | red | magenta | red | gray | red |
| CAPN12 | red | gray | red | red | red |
| C21orf33 | red | gray | gray | red | red |
| LONRF3 | red | magenta | red | gray | red |
| PRKAG2-AS1 | red | gray | gray | gray | red |
| SOSTDC1 | red | gray | gray | red | red |
| RNF183 | red | magenta | red | gray | red |
| ZC3H12D | red | gray | gray | red | red |
| HR | red | gray | gray | red | red |
| TMED6 | red | red | gray | red | red |
| PCDH20 | red | gray | green | gray | red |
| AKR1C3 | red | gray | green | red | red |
| TSPAN7 | red | greenyellow | green | gray | red |
| CYCS | red | gray | green | gray | red |
| C4BPA | red | red | red | red | red |
| TM4SF5 | red | red | green | red | red |
| TLE1 | red | magenta | red | gray | red |
| NDNF | red | red | green | gray | red |
| ACOT13 | red | red | green | red | red |
| ACAA2 | red | red | gray | red | red |
| MKNK2 | red | gray | gray | red | red |
| C1orf226 | red | magenta | gray | red | red |
| NEO1 | red | red | green | red | red |
| MTMR11 | red | red | green | red | red |
| PVRL3 | red | red | green | red | red |
| DEFB1 | red | gray | gray | gray | red |
| SLC16A5 | red | gray | green | red | red |
| ARHGAP27 | red | gray | gray | red | red |
| ERBB2 | red | gray | green | red | red |
| RAPGEFL1 | red | red | green | red | red |
| PROM1 | red | gray | gray | red | red |
| DHRS1 | red | gray | red | gray | red |
| NOXO1 | red | red | green | gray | red |
| C2orf82 | red | red | green | red | red |
| SMAGP | red | red | green | red | red |
| TMEM141 | red | red | green | gray | red |
| ABHD14B | red | gray | green | red | red |
| BAIAP2L2 | red | gray | green | red | red |
| STARD10 | red | gray | green | red | red |
| ASL | red | red | green | red | red |

TABLE 5-continued

Genes for identification of subtypes and sub-subtypes

| | CCMS | ccs | CRCA1 | CRCA2 | potential 1 |
|---|---|---|---|---|---|
| CLN3 | red | gray | green | red | red |
| FAAH | red | gray | green | red | red |
| NOS2 | red | gray | gray | gray | red |
| TRIM15 | red | gray | gray | gray | red |
| KCNE3 | red | gray | green | red | red |
| SCIN | red | magenta | green | red | red |
| GSTA1 | red | gray | green | gray | red |
| COL17A1 | red | gray | green | red | red |
| NPY6R | red | gray | gray | gray | red |
| NQO1 | red | red | green | red | red |
| CAPN8 | red | red | green | gray | red |
| MXD1 | red | gray | green | gray | red |
| TRIM31 | red | red | green | red | red |
| ALDH6A1 | red | gray | red | red | red |
| CYP2C18 | red | gray | red | gray | red |
| CYP2C9 | red | gray | red | gray | red |
| WFDC2 | red | red | green | gray | red |
| ANXA13 | red | magenta | green | red | red |
| C1orf115 | red | red | gray | red | red |
| PRSS16 | red | gray | red | gray | red |
| GDA | red | magenta | red | gray | red |
| ADORA2B | red | gray | red | gray | red |
| APOBEC1 | red | red | green | red | red |
| MAP2K6 | red | gray | green | red | red |
| EMP2 | red | red | green | red | red |
| TRHDE | red | red | green | red | red |
| VWA5A | red | red | green | gray | red |
| PPARGC1A | red | gray | green | red | red |
| UGT2A3 | red | red | green | red | red |
| CNTN3 | red | greenyellow | green | gray | red |
| HAPLN1 | red | gray | gray | gray | red |
| BMP5 | red | greenyellow | gray | gray | red |
| FAM150B | red | greenyellow | green | gray | red |
| ITGA8 | red | greenyellow | gray | gray | red |
| ADAMDEC1 | red | greenyellow | gray | gray | red |
| DNASE1L3 | red | greenyellow | gray | gray | red |
| METTL7A | red | gray | green | gray | red |
| SEPP1 | red | greenyellow | green | gray | red |
| LPHN3 | red | greenyellow | green | red | red |
| BBIP1 | red | greenyellow | green | red | red |
| PRKACB | red | greenyellow | green | gray | red |
| PCSK6 | red | gray | red | red | red |
| SLPI | red | magenta | red | gray | red |
| L1TD1 | red | magenta | red | gray | red |
| GNA14 | red | magenta | red | gray | red |
| NEDD9 | red | magenta | red | gray | red |
| TPK1 | red | gray | gray | gray | red |
| GAREM | red | magenta | gray | gray | red |
| CNGA1 | red | red | green | red | red |
| ADH6 | red | red | green | red | red |
| CMBL | red | magenta | red | red | red |
| ATP1B1 | red | gray | red | gray | red |
| NPDC1 | red | magenta | red | gray | red |
| COL9A2 | red | red | red | gray | red |
| TMEM45B | red | red | gray | red | red |
| BLNK | red | magenta | red | gray | red |
| TMEM92 | red | magenta | red | gray | red |
| BACE2 | red | magenta | red | red | red |
| RASAL1 | red | magenta | red | gray | red |
| LINC00668 | red | red | green | gray | red |
| AXDND1 | red | red | green | red | red |
| COL4A6 | red | greenyellow | green | gray | red |
| SLC6A14 | red | magenta | red | gray | red |
| IRF6 | red | gray | green | red | red |
| ASS1 | red | magenta | gray | gray | red |
| GSDMB | red | gray | gray | gray | red |
| SGPP2 | red | gray | gray | gray | red |
| RORC | red | red | red | red | red |
| 3-Mar | red | magenta | red | gray | red |
| CLDN23 | red | greenyellow | green | red | red |
| CDHR2 | red | gray | green | red | red |
| MALL | red | red | green | gray | red |
| LRG1 | red | magenta | red | gray | red |
| PTPRF | red | gray | green | red | red |
| SERINC2 | red | red | green | red | red |
| WNT4 | red | red | gray | red | red |

TABLE 5-continued

Genes for identification of subtypes and sub-subtypes

| | CCMS | ccs | CRCA1 | CRCA2 | potential 1 |
|---|---|---|---|---|---|
| S100P | red | magenta | red | gray | red |
| OVOL2 | red | gray | green | red | red |
| TMEM37 | red | greenyellow | green | gray | red |
| TUBAL3 | red | red | green | red | red |
| EPHX2 | red | red | red | red | red |
| GBA3 | red | gray | green | gray | red |
| NR1H4 | red | gray | green | gray | red |
| TMEM254 | red | gray | green | gray | red |
| HOXB13 | red | gray | red | red | red |
| C1orf21 | red | magenta | red | gray | red |
| ALDOB | red | red | green | gray | red |
| LGALS2 | red | gray | green | gray | red |
| PDCD6IP | red | gray | gray | red | red |
| ZG16B | red | red | red | gray | red |
| TMPRSS4 | red | red | green | red | red |
| SLC5A1 | red | red | green | red | red |
| SLC44A3 | red | red | green | red | red |
| PLEKHA6 | red | red | green | gray | red |
| STAP2 | red | red | green | red | red |
| MAOA | red | red | green | red | red |
| ANKS4B | red | red | green | red | red |
| NRARP | red | red | green | red | red |
| BDH1 | red | red | green | red | red |
| HADH | red | red | green | red | red |
| PPP1R1B | red | red | green | red | red |
| FUT3 | red | gray | green | red | red |
| FUT6 | red | red | green | red | red |
| TMC4 | red | red | green | red | red |
| BCL2L14 | red | red | green | red | red |
| ATP2C2 | red | red | green | red | red |
| TTC39A | red | red | green | red | red |
| FZD5 | red | red | green | red | red |
| CORO2A | red | red | green | red | red |
| CALML4 | red | red | green | red | red |
| PIP5K1B | red | red | green | red | red |
| CLRN3 | red | red | green | red | red |
| MUC13 | red | red | red | red | red |
| PRR15L | red | red | green | red | red |
| HDHD3 | red | red | green | red | red |
| USH1C | red | red | green | red | red |
| DMBT1 | red | magenta | red | red | red |
| BCL2L15 | red | red | green | red | red |
| LCN2 | red | red | red | gray | red |
| PDZK1IP1 | red | red | red | red | red |
| HGD | red | red | red | red | red |
| HMGN2P46 | red | magenta | green | red | red |
| MMP28 | red | magenta | gray | red | red |
| ALDH1L1 | red | gray | red | gray | red |
| DQX1 | red | red | gray | red | red |
| TMEM171 | red | gray | red | gray | red |
| FUT2 | red | red | red | red | red |
| ACSM3 | red | red | green | red | red |
| NDRG2 | red | red | green | gray | red |
| GOLM1 | red | red | red | red | red |
| SYTL5 | red | red | green | red | red |
| TRPM4 | red | red | green | red | red |
| PI3 | red | magenta | red | gray | red |
| CRYM | red | red | green | red | red |
| CLMN | red | red | green | red | red |
| PRSS12 | red | magenta | gray | red | red |
| C1orf210 | red | gray | gray | red | red |
| ABCC3 | red | red | gray | red | red |
| PIGR | red | red | red | gray | red |
| SLC28A2 | red | red | green | gray | red |
| BMP2 | red | magenta | red | gray | red |
| TRPA1 | red | greenyellow | green | red | red |
| NUDT16 | red | magenta | red | red | red |
| SCNN1A | red | red | red | red | red |
| TMEM246 | red | magenta | red | gray | red |
| SLITRK6 | red | magenta | red | gray | red |
| CATSPERB | red | magenta | red | gray | red |
| AMN | red | magenta | gray | gray | red |
| FRMD3 | red | magenta | gray | gray | red |
| TSPAN3 | red | gray | red | red | red |
| CHP1 | red | gray | red | gray | red |
| HSD17B2 | red | red | gray | gray | red |

TABLE 5-continued

Genes for identification of subtypes and sub-subtypes

| | CCMS | ccs | CRCA1 | CRCA2 | potential 1 |
|---|---|---|---|---|---|
| GCNT3 | red | magenta | red | gray | red |
| LIPH | red | magenta | gray | gray | red |
| PPP1R36 | red | red | red | red | red |
| GALNT12 | red | magenta | red | red | red |
| KIAA1324 | red | magenta | red | red | red |
| C9orf152 | red | red | green | red | red |
| FOXA3 | red | red | red | red | red |
| MUC5B | red | magenta | red | gray | red |
| TCEA3 | red | magenta | green | red | red |
| RETNLB | red | red | green | red | red |
| SLC9A2 | red | red | green | red | red |
| C2orf72 | red | magenta | red | gray | red |
| PTGER4 | red | red | red | gray | red |
| PDXDC1 | red | gray | red | red | red |
| PLD1 | red | red | red | gray | red |
| SHROOM3 | red | magenta | red | red | red |
| TSPAN13 | red | magenta | red | gray | red |
| IQGAP2 | red | magenta | red | gray | red |
| DSC2 | red | gray | red | red | red |
| CAMK2D | red | gray | gray | gray | red |
| ATP8A1 | red | magenta | red | gray | red |
| SLC2A13 | red | magenta | red | red | red |
| PAPSS2 | red | magenta | red | red | red |
| LGR4 | red | magenta | red | red | red |
| TNFRSF11A | red | magenta | red | gray | red |
| STYK1 | red | magenta | red | gray | red |
| CCDC68 | red | magenta | gray | gray | red |
| CASP7 | red | magenta | red | gray | red |
| LIMA1 | red | red | red | gray | red |
| ABHD3 | red | gray | red | gray | red |
| GSKIP | red | magenta | red | gray | red |
| TC2N | red | magenta | gray | gray | red |
| SMIM14 | red | magenta | red | gray | red |
| LAMA1 | red | magenta | gray | red | red |
| ASRGL1 | red | magenta | red | gray | red |
| TFF3 | red | red | red | red | red |
| GNE | red | magenta | red | gray | red |
| RNASE4 | red | magenta | red | gray | red |
| TFF1 | red | magenta | red | gray | red |
| PTGER2 | red | magenta | red | gray | red |
| RHBDL2 | red | magenta | red | red | red |
| MB | red | magenta | red | gray | red |
| RAP1GAP | red | magenta | red | gray | red |
| AGR2 | red | magenta | red | gray | red |
| AGR3 | red | magenta | red | gray | red |
| MRAP2 | red | magenta | red | red | red |
| ANG | red | magenta | red | gray | red |
| ZBTB7C | red | magenta | red | gray | red |
| ST3GAL4 | red | magenta | red | gray | red |
| KLK1 | red | magenta | green | red | red |
| CHST5 | red | magenta | red | red | red |
| FFAR4 | red | magenta | red | gray | red |
| KLF4 | red | gray | red | gray | red |
| ATP2A3 | red | gray | red | red | red |
| TMEM61 | red | magenta | red | gray | red |
| ATOH1 | red | magenta | red | red | red |
| LINC00261 | red | magenta | red | gray | red |
| BCAS1 | red | magenta | red | red | red |
| SPDEF | red | magenta | red | gray | red |
| CAPN9 | red | magenta | red | gray | red |
| ST6GALNAC1 | red | magenta | red | red | red |
| ITLN1 | red | magenta | red | red | red |
| REG4 | red | magenta | red | gray | red |
| HEPACAM2 | red | magenta | red | red | red |
| B3GNT6 | red | magenta | red | gray | red |
| SPINK4 | red | magenta | red | gray | red |
| FCGBP | red | magenta | red | gray | red |
| MUC2 | red | magenta | red | gray | red |
| CREB3L1 | red | magenta | red | gray | red |
| RAB26 | red | magenta | red | gray | red |
| SIDT1 | red | magenta | red | gray | red |
| MLPH | red | magenta | red | gray | red |
| RAB27B | red | magenta | gray | gray | red |
| GDPD3 | red | gray | green | red | red |
| CES2 | red | red | green | red | red |
| NR5A2 | red | red | green | red | red |

TABLE 5-continued

Genes for identification of subtypes and sub-subtypes

| | CCMS | ccs | CRCA1 | CRCA2 | potential 1 |
|---|---|---|---|---|---|
| PARM1 | red | gray | red | red | red |
| DHRS11 | red | gray | green | red | red |
| CWH43 | red | red | green | red | red |
| GNA11 | red | gray | green | gray | red |
| TST | red | red | gray | red | red |
| HRCT1 | red | red | green | red | red |
| PKIB | red | greenyellow | green | gray | red |
| SMPDL3A | red | gray | red | gray | red |
| SMPD3 | red | red | green | red | red |
| FMO5 | red | red | green | red | red |
| INSL5 | red | gray | gray | gray | red |
| DENND2A | red | gray | green | red | red |
| FAM162A | red | red | green | red | red |
| SRI | red | gray | green | red | red |
| SLC17A4 | red | red | green | red | red |
| PDE9A | red | red | green | red | red |
| MGLL | red | greenyellow | green | red | red |
| ACVRL1 | red | greenyellow | green | red | red |
| RNF186 | red | red | green | red | red |
| DUOX2 | red | red | green | re | red |
| DUOXA2 | red | red | green | re | red |
| FXYD3 | red | gray | red | re | red |
| LGALS3 | red | gray | green | re | red |
| GGT6 | red | red | green | re | red |
| MYO1A | red | red | green | re | red |
| CASP5 | red | red | red | re | red |
| UGT2B15 | red | red | green | re | red |
| UGT2B17 | red | greenyellow | green | re | red |
| FAM132A | red | red | green | re | red |
| EDN3 | red | greenyellow | green | re | red |
| TTC22 | red | red | green | re | red |
| PTPRH | red | red | red | re | red |
| TMEM54 | red | red | red | re | red |
| CDC42EP5 | red | red | red | re | red |
| ETHE1 | red | red | red | re | red |
| LRRC66 | red | red | green | re | red |
| CA12 | red | magenta | red | re | red |
| CDHR5 | red | red | green | re | red |
| BTNL8 | red | red | gray | re | red |
| CHP2 | red | red | green | re | red |
| HHLA2 | red | red | green | re | red |
| SLC51B | red | red | green | re | red |
| PLCE1 | red | red | green | re | red |
| HSD11B2 | red | red | green | re | red |
| VIPR1 | red | red | green | re | red |
| FAM3D | red | red | green | re | red |
| CAPN5 | red | red | green | re | red |
| C4orf19 | red | red | red | re | red |
| SLC44A4 | red | red | green | re | red |
| LINC00675 | red | red | green | re | red |
| GPA33 | red | red | green | re | red |
| LGALS4 | red | red | green | re | red |
| PADI2 | red | greenyellow | green | re | red |
| MOGAT2 | red | red | green | re | red |
| CEACAM7 | red | red | green | re | red |
| NXPE1 | red | red | green | re | red |
| NXPE4 | red | red | green | re | red |
| ENTPD5 | red | red | green | re | red |
| SULT1B1 | red | red | green | re | red |
| XDH | red | red | red | re | red |
| CES3 | red | red | red | re | red |
| AHCYL2 | red | gray | red | re | red |
| AKR1B10 | red | red | green | re | red |
| SIAE | red | gray | red | re | red |
| ATP8B1 | red | gray | red | re | red |
| RBM47 | red | gray | red | re | red |
| SCGB2A1 | red | magenta | red | gray | red |
| CHGA | red | greenyellow | green | gray | red |
| SCARA5 | red | greenyellow | green | gray | red |
| MFSD4 | red | red | green | red | red |
| PLAC8 | red | magenta | red | gray | red |
| AQP8 | red | red | green | red | red |
| B3GNT7 | red | gray | green | gray | red |
| GCG | red | greenyellow | green | gray | red |
| ADH1C | red | red | green | red | red |
| ABCC13 | red | red | green | red | red |

TABLE 5-continued

Genes for identification of subtypes and sub-subtypes

| | CCMS | ccs | CRCA1 | CRCA2 | potential 1 |
|---|---|---|---|---|---|
| DHRS9 | red | gray | green | gray | red |
| ADTRP | red | red | green | gray | red |
| ITM2C | red | gray | red | red | red |
| BEST2 | red | red | green | red | red |
| MUC4 | red | magenta | red | gray | red |
| TSPAN1 | red | red | red | red | red |
| NR3C2 | red | magenta | red | red | red |
| CLCA1 | red | red | red | red | red |
| CCL28 | red | red | red | red | red |
| VSIG2 | red | red | red | red | red |
| SPINK5 | red | red | green | gray | red |
| C2orf88 | red | greenyellow | green | red | red |
| SI | red | red | green | gray | red |
| SCNN1B | red | gray | green | red | red |
| CLDN8 | red | gray | green | gray | red |
| CD177 | red | gray | green | gray | red |
| GUCA2B | red | red | green | gray | red |
| CLCA4 | red | red | green | red | red |
| MS4A12 | red | red | green | red | red |
| CA1 | red | red | green | gray | red |
| CA4 | red | red | green | gray | red |
| ZG16 | red | red | green | red | red |
| CA2 | red | gray | red | gray | red |
| SLC4A4 | red | magenta | red | gray | red |
| MGST1 | red | gray | gray | gray | red |
| GATA6 | red | gray | gray | red | red |
| PPARGC1B | red | gray | gray | red | red |
| KBTBD11 | red | red | gray | red | red |
| PLEKHH1 | red | red | gray | red | red |
| SH3RF2 | red | red | red | red | red |
| SLC39A8 | red | magenta | red | red | red |
| UQCRC2 | red | gray | red | red | red |
| DNAJC22 | red | red | green | gray | red |
| NEDD4L | red | gray | red | red | red |
| C3orf52 | red | magenta | red | gray | red |
| ARHGAP32 | red | gray | red | red | red |
| ELL3 | red | magenta | gray | gray | red |
| LRRC16A | red | gray | gray | gray | red |
| EHHADH | red | gray | green | red | red |
| TRIM36 | red | gray | red | red | red |
| MYO5C | red | gray | gray | gray | red |
| TTC19 | red | gray | red | gray | red |
| HK2 | red | gray | red | gray | red |
| BCL10 | red | gray | red | red | red |
| F2RL1 | red | red | red | gray | red |
| ELOVL6 | red | gray | gray | gray | red |
| FRK | red | gray | gray | gray | red |
| MCTP2 | red | gray | red | gray | red |
| SLC27A2 | red | gray | red | gray | red |
| AFG3L2 | red | magenta | gray | gray | red |
| PKP2 | red | gray | red | gray | red |
| UGT8 | red | gray | red | gray | red |
| ADH1A2 | black | black | black | black | |
| SBSPON | turquoise | turquoise | gray | turquoise | |
| MSX2 | turquoise | turquoise | gray | gray | |
| TBX3 | brown | green | gray | gray | |
| KREMEN1 | brown | green | gray | gray | |
| DKK4 | turquoise | gray | gray | turquoise | |
| SP5 | brown | gray | gray | gray | |
| AVPR1A | black | black | gray | black | |
| FGB | turquoise | gray | gray | gray | |
| CD99P1 | turquoise | gray | gray | turquoise | |
| ONECUT2 | turquoise | gray | gray | gray | |
| AIM1L | turquoise | gray | gray | turquoise | |
| IQCE | black | gray | gray | gray | |
| NOL3 | turquoise | gray | gray | turquoise | |
| SPNS2 | black | black | black | gray | |
| DUSP27 | turquoise | gray | gray | turquoise | |
| ZNF718 | black | gray | black | black | |
| FOLR1 | turquoise | turquoise | gray | gray | |
| SOX1 | turquoise | gray | gray | turquoise | |
| LINC00476 | turquoise | gray | turquoise | gray | |
| ADH4 | turquoise | gray | gray | turquoise | |
| PTPRN2 | turquoise | gray | turquoise | gray | |
| SOX6 | turquoise | gray | turquoise | turquoise | |
| EML6 | turquoise | turquoise | gray | gray | |

TABLE 5-continued

Genes for identification of subtypes and sub-subtypes

| | CCMS | ccs | CRCA1 | CRCA2 | potential 1 |
|---|---|---|---|---|---|
| APH1A | black | gray | gray | gray | |
| REEP6 | black | gray | gray | gray | |
| AGFG2 | brown | green | gray | gray | |
| AMFR | black | gray | gray | gray | |
| HMBOX1 | turquoise | gray | gray | turquoise | |
| GRIN2D | brown | gray | gray | gray | |
| KDELR1 | turquoise | gray | gray | turquoise | |
| LPHN1 | turquoise | gray | gray | turquoise | |
| NSMF | brown | gray | gray | brown | |
| SH3GLB2 | black | gray | black | gray | |
| ARHGDIA | turquoise | gray | gray | turquoise | |
| MAZ | brown | green | gray | brown | |
| GNB2 | black | gray | gray | gray | |
| YKT6 | turquoise | gray | gray | gray | |
| OGDH | turquoise | gray | gray | gray | |
| URGCP | turquoise | gray | gray | gray | |
| GABRB1 | turquoise | turquoise | turquoise | turquoise | |
| NFIA | turquoise | gray | gray | gray | |
| ECHDC2 | turquoise | gray | gray | turquoise | |
| RHOU | turquoise | gray | gray | turquoise | |
| CPA6 | turquoise | turquoise | gray | gray | |
| MLXIP | turquoise | gray | gray | turquoise | |
| RERE | turquoise | gray | turquoise | turquoise | |
| EP400 | green | gray | yellow | yellow | |
| SPEN | turquoise | gray | gray | turquoise | |
| SRRM2 | turquoise | gray | gray | turquoise | |
| ARMCX4 | turquoise | turquoise | gray | gray | |
| PON3 | turquoise | gray | turquoise | gray | |
| CLGN | turquoise | turquoise | gray | turquoise | |
| SHC3 | turquoise | turquoise | gray | turquoise | |
| CA9 | black | gray | gray | gray | |
| WISP3 | turquoise | gray | gray | turquoise | |
| NMU | turquoise | gray | turquoise | gray | |
| MALAT1 | turquoise | gray | gray | turquoise | |
| DAPP1 | black | black | black | black | |
| GTSE1 | brown | brown | gray | brown | |
| AKR1C4 | turquoise | gray | gray | gray | |
| MIRLET7DHG | turquoise | turquoise | gray | turquoise | |
| C12orf56 | turquoise | gray | turquoise | gray | |
| PEX6 | turquoise | gray | turquoise | gray | |
| MAGEA11 | turquoise | gray | gray | turquoise | |
| NOS3 | turquoise | gray | turquoise | turquoise | |
| THSD4 | turquoise | gray | gray | turquoise | |
| MCOLN2 | black | black | black | gray | |
| SPAG16 | turquoise | turquoise | gray | turquoise | |
| PPP2R2C | turquoise | gray | gray | gray | |
| WFS1 | turquoise | gray | turquoise | gray | |
| TNFSF15 | black | gray | gray | gray | |
| AGA | black | gray | gray | gray | |
| ABCA12 | black | black | gray | gray | |
| WDR72 | turquoise | gray | turquoise | gray | |
| IL17A | turquoise | gray | gray | gray | |
| DPP10 | turquoise | gray | turquoise | turquoise | |
| MTTP | turquoise | gray | turquoise | gray | |
| MXI1 | turquoise | gray | turquoise | turquoise | |
| SLC38A11 | turquoise | gray | gray | turquoise | |
| DSC3 | turquoise | turquoise | turquoise | turquoise | |
| HOXB-AS3 | turquoise | turquoise | turquoise | turquoise | |
| HOXB9 | yellow | yellow | green | gray | |
| HOXB8 | turquoise | turquoise | gray | gray | |
| HOXB7 | black | gray | black | gray | |
| HOXB3 | turquoise | turquoise | turquoise | gray | |
| HOXB5 | turquoise | turquoise | gray | gray | |
| HOXB6 | black | black | black | gray | |
| TESC | turquoise | gray | turquoise | turquoise | |
| HOXA2 | turquoise | turquoise | gray | turquoise | |
| HOXA3 | turquoise | turquoise | gray | gray | |
| HOXA13 | yellow | gray | yellow | red | |
| HOXA11-AS | turquoise | gray | gray | gray | |
| HOXA10 | turquoise | turquoise | gray | gray | |
| HOXA11 | turquoise | turquoise | gray | turquoise | |
| HOXA5 | turquoise | turquoise | turquoise | turquoise | |
| HOXA7 | turquoise | turquoise | gray | turquoise | |
| KCNJ3 | black | gray | black | gray | |
| MUC17 | black | gray | black | gray | |
| PRKCA | turquoise | gray | gray | turquoise | |

TABLE 5-continued

Genes for identification of subtypes and sub-subtypes

| | CCMS | ccs | CRCA1 | CRCA2 | potential 1 |
|---|---|---|---|---|---|
| SLC38A5 | black | gray | gray | gray | |
| TIMP4 | turquoise | gray | gray | gray | |
| FAM118A | turquoise | gray | gray | turquoise | |
| GSTM4 | black | gray | black | black | |
| ERAP1 | black | black | black | gray | |
| SYNPR | turquoise | turquoise | gray | turquoise | |
| CHST13 | turquoise | gray | gray | gray | |
| CYP4V2 | black | black | black | gray | |
| ZNF334 | turquoise | turquoise | turquoise | turquoise | |
| WIPI1 | turquoise | gray | gray | gray | |
| IL33 | turquoise | turquoise | turquoise | turquoise | |
| NTS | turquoise | turquoise | turquoise | turquoise | |
| TNIK | turquoise | gray | gray | gray | |
| SPAG4 | turquoise | gray | turquoise | turquoise | |
| CTBP1 | turquoise | gray | gray | turquoise | |
| CLDN10 | turquoise | gray | turquoise | turquoise | |
| ORM1 | turquoise | gray | turquoise | gray | |
| GPR37 | turquoise | gray | gray | turquoise | |
| CTTN | black | black | black | gray | |
| ITGB8 | turquoise | turquoise | gray | turquoise | |
| PTGR1 | black | gray | gray | gray | |
| SCD5 | turquoise | turquoise | gray | turquoise | |
| TRIM4 | turquoise | gray | turquoise | turquoise | |
| NUCKS1 | turquoise | gray | gray | gray | |
| ZC3HAV1 | turquoise | gray | gray | gray | |
| EGFR | turquoise | gray | gray | gray | |
| SRGAP1 | turquoise | gray | gray | gray | |
| SALL1 | turquoise | gray | gray | gray | |
| GRB14 | black | gray | gray | gray | |
| LGSN | turquoise | gray | turquoise | turquoise | |
| GLDN | black | gray | black | gray | |
| GPR27 | black | gray | gray | gray | |
| ATHL1 | turquoise | turquoise | gray | turquoise | |
| ALDH1B1 | turquoise | gray | gray | gray | |
| UBE4B | turquoise | gray | turquoise | turquoise | |
| C6orf141 | black | gray | gray | gray | |
| CACNB2 | turquoise | gray | gray | turquoise | |
| PRUNE2 | turquoise | turquoise | gray | turquoise | |
| KCNQ1OT1 | turquoise | turquoise | turquoise | turquoise | |
| PID1 | turquoise | gray | gray | turquoise | |
| RAB32 | turquoise | gray | gray | turquoise | |
| MTSS1 | turquoise | turquoise | turquoise | turquoise | |
| IER3 | turquoise | gray | turquoise | turquoise | |
| LRRN1 | turquoise | gray | turquoise | turquoise | |
| CELSR1 | turquoise | turquoise | gray | turquoise | |
| TMEM178B | turquoise | gray | gray | gray | |
| MAP2K7 | black | gray | black | gray | |
| KCNJ2 | black | black | black | black | |
| RNF39 | turquoise | gray | turquoise | turquoise | |
| LGR6 | turquoise | turquoise | gray | turquoise | |
| OAS1 | black | gray | black | black | |
| JAG2 | turquoise | turquoise | turquoise | gray | |
| SULT1E1 | turquoise | gray | gray | gray | |
| TP53 | black | gray | black | black | |
| KANSL1-AS1 | black | gray | gray | gray | |
| OLFM1 | turquoise | turquoise | turquoise | turquoise | |
| WNT11 | turquoise | gray | turquoise | gray | |
| LRRC41 | turquoise | gray | gray | turquoise | |
| SHISA6 | turquoise | gray | turquoise | turquoise | |
| C15orf57 | black | gray | black | gray | |
| GPR64 | turquoise | turquoise | turquoise | turquoise | |
| NDRG1 | turquoise | gray | gray | turquoise | |
| SLC6A8 | black | gray | gray | gray | |
| PYCARD | black | gray | gray | gray | |
| C2orf68 | turquoise | gray | gray | gray | |
| IFITM1 | black | gray | black | black | |
| NRCAM | turquoise | gray | gray | turquoise | |
| IL13RA2 | turquoise | turquoise | turquoise | turquoise | |
| MMP10 | black | black | black | black | |
| RPS23 | turquoise | gray | gray | turquoise | |
| MFI2 | turquoise | turquoise | gray | turquoise | |
| SLC51A | black | gray | gray | gray | |
| ZBED1 | turquoise | gray | gray | turquoise | |
| H2AFY2 | turquoise | gray | turquoise | turquoise | |
| SLCO1B3 | black | black | gray | gray | |
| FGF20 | turquoise | gray | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| PRR9 | turquoise | gray | gray | turquoise | |
| KLHL13 | turquoise | gray | turquoise | turquoise | |
| SEZ6L2 | turquoise | gray | gray | turquoise | |
| GPM6A | turquoise | turquoise | gray | turquoise | |
| COL4A3 | turquoise | gray | turquoise | turquoise | |
| IRX2 | turquoise | gray | gray | gray | |
| ZDHHC2 | turquoise | gray | gray | gray | |
| FAM149A | black | black | black | gray | |
| TNFRSF21 | black | gray | black | gray | |
| TAPBPL | black | black | black | black | |
| HOXD13 | turquoise | gray | turquoise | turquoise | |
| CHURC1 | black | gray | gray | gray | |
| CCR6 | black | black | gray | black | |
| ARID1B | turquoise | gray | turquoise | turquoise | |
| ZC3H12C | black | black | black | black | |
| TMEM159 | black | gray | black | gray | |
| SH3KBP1 | black | black | black | gray | |
| CLIC5 | black | black | black | gray | |
| GMPR | black | black | black | black | |
| C11orf70 | turquoise | turquoise | gray | turquoise | |
| HIST1H2BC | black | black | black | black | |
| HIST1H1C | black | black | black | black | |
| HIST1H2BH | black | black | gray | gray | |
| HIST1H2BK | black | gray | gray | gray | |
| HIST1H2AC | black | gray | gray | gray | |
| HIST1H2BD | black | gray | gray | gray | |
| EMC3 | black | gray | gray | black | |
| MIDN | turquoise | gray | turquoise | turquoise | |
| TMPRSS3 | black | black | black | black | |
| TRIM29 | turquoise | turquoise | turquoise | turquoise | |
| PXN | turquoise | gray | gray | turquoise | |
| GJB3 | black | gray | gray | gray | |
| EPHA2 | black | gray | black | gray | |
| SFN | black | gray | black | gray | |
| VASP | turquoise | gray | gray | gray | |
| GPRC5A | black | gray | gray | gray | |
| S100A6 | black | gray | black | gray | |
| C19orf33 | black | gray | gray | gray | |
| CLTB | black | gray | gray | gray | |
| MINK1 | black | black | black | black | |
| GABRP | black | black | black | gray | |
| SLC28A3 | black | magenta | black | gray | |
| SYT13 | black | magenta | black | black | |
| RIMS3 | black | magenta | gray | gray | |
| DNAJA4 | black | gray | black | gray | |
| PPP1R9A | green | green | gray | gray | |
| MIPOL1 | black | black | gray | gray | |
| KANSL1L | turquoise | gray | turquoise | turquoise | |
| ZNF204P | black | magenta | black | black | |
| DUSP6 | black | black | gray | gray | |
| CPS1 | black | magenta | black | gray | |
| BTNL9 | black | magenta | black | black | |
| ANKRD37 | black | black | black | black | |
| MIR210HG | black | black | black | gray | |
| RPH3AL | red | magenta | red | gray | |
| VPS53 | black | magenta | black | gray | |
| RAP1GAP2 | black | magenta | black | gray | |
| ECI2 | black | black | gray | black | |
| AK1 | black | black | black | gray | |
| TSPAN15 | black | gray | gray | black | |
| SLC50A1 | black | gray | gray | gray | |
| CHCHD10 | red | gray | gray | gray | |
| GOT1 | brown | brown | gray | brown | |
| TSTA3 | brown | gray | gray | brown | |
| DEGS2 | red | magenta | red | gray | |
| IMPA2 | red | magenta | red | red | |
| GMDS | red | gray | red | gray | |
| ACPP | brown | gray | gray | brown | |
| RSPH1 | brown | gray | gray | brown | |
| FGFBP1 | red | gray | red | gray | |
| GLRX | black | black | gray | black | |
| CLDN18 | black | black | black | black | |
| SLC16A14 | black | black | black | black | |
| NXF3 | black | magenta | gray | gray | |
| SLC25A37 | black | gray | black | gray | |
| ME1 | black | magenta | gray | gray | |

TABLE 5-continued

Genes for identification of subtypes and sub-subtypes

| | CCMS | ccs | CRCA1 | CRCA2 | potential 1 |
|---|---|---|---|---|---|
| SSTR1 | brown | gray | gray | gray | |
| PITPNM3 | red | magenta | red | gray | |
| GALNT5 | black | magenta | gray | gray | |
| BAG1 | black | gray | gray | gray | |
| SLAIN1 | black | magenta | black | black | |
| ARSJ | black | magenta | black | black | |
| SLC36A4 | black | black | black | black | |
| GP2 | black | magenta | black | gray | |
| SERPINA1 | black | magenta | gray | black | |
| CKAP4 | turquoise | gray | gray | gray | |
| RASD1 | turquoise | gray | gray | turquoise | |
| SLC18A1 | red | magenta | red | gray | |
| FAM174B | turquoise | gray | gray | gray | |
| CA8 | red | magenta | red | gray | |
| AQP3 | black | magenta | gray | gray | |
| TOX | black | magenta | gray | black | |
| ISL1 | black | black | black | black | |
| ARX | black | magenta | black | black | |
| SEMG1 | black | magenta | black | gray | |
| ANXA10 | black | black | black | gray | |
| PLA2G2A | black | magenta | black | black | |
| AGPAT9 | black | magenta | gray | black | |
| KIAA1211 | black | black | black | gray | |
| HS3ST1 | black | magenta | black | gray | |
| VNN1 | black | black | black | black | |
| F3 | black | magenta | black | gray | |
| MBOAT1 | black | gray | gray | black | |
| SLC1A1 | black | magenta | black | black | |
| PLA2G4A | black | magenta | black | black | |
| MUC1 | black | magenta | gray | gray | |
| TCN1 | black | magenta | gray | gray | |
| KCNK6 | black | magenta | black | black | |
| KLK11 | black | black | gray | gray | |
| MUC5AC | black | magenta | black | gray | |
| S100A14 | red | magenta | red | gray | |
| SYTL4 | black | magenta | gray | gray | |
| SERPINB5 | black | magenta | black | gray | |
| KCNK1 | black | magenta | gray | gray | |
| C4BPB | red | magenta | red | gray | |
| CD55 | black | magenta | gray | gray | |
| SRD5A3 | black | magenta | gray | gray | |
| RNF125 | black | magenta | black | gray | |
| SLC17A5 | black | magenta | gray | gray | |
| IL1R2 | black | magenta | gray | gray | |
| CTSE | black | magenta | gray | gray | |
| FAM46A | black | magenta | black | gray | |
| PLLP | black | magenta | black | gray | |
| MYRF | black | magenta | black | gray | |
| TFF2 | black | magenta | black | gray | |
| QSOX1 | black | gray | gray | gray | |
| KDELR3 | black | magenta | gray | gray | |
| SEC24D | black | magenta | black | black | |
| CRIP1 | black | magenta | black | gray | |
| TFAP2A | black | magenta | black | gray | |
| SYTL1 | black | magenta | black | gray | |
| SDR16C5 | black | magenta | gray | gray | |
| DUSP4 | black | magenta | black | gray | |
| S100A16 | black | magenta | black | gray | |
| INPP1 | black | magenta | gray | gray | |
| TRIM7 | black | magenta | gray | gray | |
| ASPHD2 | black | magenta | black | gray | |
| HPSE | black | magenta | black | gray | |
| EGLN3 | black | magenta | gray | gray | |
| SERPINB1 | black | magenta | gray | gray | |
| IFNGR1 | black | gray | black | black | |
| IL18 | black | magenta | black | gray | |
| IVNS1ABP | black | magenta | black | black | |
| RPS27L | black | magenta | black | black | |
| SPATA18 | black | black | black | black | |
| KITLG | turquoise | gray | gray | gray | |
| SEC22B | black | gray | black | black | |
| FRMD4B | black | magenta | gray | gray | |
| SNAP23 | black | gray | gray | gray | |
| MTUS1 | black | magenta | black | gray | |
| RNF145 | black | magenta | gray | gray | |
| STS | black | magenta | gray | gray | |

TABLE 5-continued

Genes for identification of subtypes and sub-subtypes

| | CCMS | ccs | CRCA1 | CRCA2 | potential 1 |
|---|---|---|---|---|---|
| ENOSF1 | brown | brown | gray | brown | |
| KIAA0895 | brown | gray | gray | brown | |
| DYX1C1 | black | black | black | black | |
| OXCT1 | black | magenta | black | black | |
| TEX9 | black | magenta | black | gray | |
| FBXO16 | brown | gray | gray | brown | |
| PPAPDC1B | black | magenta | black | black | |
| MOCOS | brown | gray | gray | brown | |
| ME2 | black | gray | black | gray | |
| ZNF232 | black | gray | black | gray | |
| NUDT6 | black | magenta | black | gray | |
| SPTLC2 | black | gray | black | gray | |
| ARF6 | black | gray | gray | gray | |
| FUT8 | black | gray | black | gray | |
| SMEK1 | black | gray | black | gray | |
| CYB5D1 | brown | brown | gray | brown | |
| GLOD4 | brown | green | gray | brown | |
| SMAD2 | black | gray | black | gray | |
| SMAD4 | black | black | black | black | |
| SS18 | black | gray | black | gray | |
| SLC18B1 | black | magenta | black | gray | |
| GPR126 | black | gray | black | gray | |
| MBP | black | black | black | gray | |
| ZCCHC2 | black | black | black | gray | |
| INO80C | black | gray | black | gray | |
| FECH | black | magenta | black | gray | |
| PIAS2 | black | gray | gray | gray | |
| HSPA4L | brown | brown | gray | brown | |
| RPL22L1 | black | gray | black | gray | |
| CAPN6 | turquoise | turquoise | turquoise | turquoise | |
| ZNF844 | turquoise | turquoise | turquoise | turquoise | |
| TMEM99 | turquoise | turquoise | gray | turquoise | |
| MYEOV | black | black | black | gray | |
| TMEM150C | turquoise | turquoise | gray | turquoise | |
| DPP4 | black | black | black | black | |
| CYP27A1 | turquoise | gray | gray | turquoise | |
| PRSS21 | black | black | black | black | |
| KIF1C | turquoise | gray | gray | gray | |
| SERPIND1 | turquoise | gray | gray | turquoise | |
| BEX5 | black | black | black | gray | |
| TKTL1 | turquoise | gray | gray | gray | |
| ALPK3 | turquoise | turquoise | turquoise | turquoise | |
| CFB | black | black | black | black | |
| SYT17 | turquoise | gray | gray | turquoise | |
| TPPP | black | magenta | black | gray | |
| EFNB2 | turquoise | gray | turquoise | gray | |
| EPHB1 | turquoise | turquoise | turquoise | turquoise | |
| MAEL | turquoise | gray | turquoise | turquoise | |
| ZNF862 | turquoise | turquoise | turquoise | gray | |
| PRRC2B | turquoise | gray | gray | gray | |
| CELF2 | turquoise | gray | turquoise | turquoise | |
| SLC39A14 | black | gray | black | gray | |
| MCOLN3 | turquoise | gray | turquoise | turquoise | |
| CLN8 | black | gray | gray | gray | |
| C8orf4 | turquoise | gray | turquoise | turquoise | |
| TBXAS1 | black | black | gray | gray | |
| SULT1C4 | turquoise | gray | gray | gray | |
| MME | turquoise | turquoise | turquoise | turquoise | |
| ZIC2 | black | magenta | black | gray | |
| APOA2 | turquoise | gray | gray | gray | |
| TPPP3 | turquoise | gray | gray | turquoise | |
| SERP2 | turquoise | gray | turquoise | turquoise | |
| ARHGEF9 | turquoise | gray | gray | turquoise | |
| CNKSR3 | turquoise | gray | turquoise | turquoise | |
| PTGDR | black | black | black | black | |
| TSHZ1 | turquoise | turquoise | turquoise | turquoise | |
| TCAM1P | turquoise | gray | gray | gray | |
| IRX3 | black | black | black | gray | |
| C2 | black | black | black | gray | |
| MVB12A | black | black | black | gray | |
| RRAS2 | turquoise | gray | turquoise | turquoise | |
| LGALS9 | black | black | black | black | |
| ASPHD1 | black | gray | black | gray | |
| GAL | turquoise | turquoise | turquoise | turquoise | |
| SLC4A11 | black | black | black | gray | |
| PTPN13 | turquoise | turquoise | gray | turquoise | |

TABLE 5-continued

Genes for identification of subtypes and sub-subtypes

| | CCMS | ccs | CRCA1 | CRCA2 | potential 1 |
|---|---|---|---|---|---|
| MAGEA12 | turquoise | gray | gray | turquoise | |
| TMEFF2 | turquoise | gray | gray | turquoise | |
| KLHL29 | turquoise | gray | gray | turquoise | |
| NOD2 | turquoise | turquoise | turquoise | turquoise | |
| ACOT4 | black | gray | gray | gray | |
| MYBL1 | black | black | black | gray | |
| ZNF43 | turquoise | turquoise | gray | turquoise | |
| DLL1 | turquoise | gray | gray | turquoise | |
| FZD10 | turquoise | turquoise | turquoise | turquoise | |
| WWOX | turquoise | turquoise | gray | gray | |
| PTPN1 | turquoise | gray | gray | turquoise | |
| LARP6 | turquoise | turquoise | gray | turquoise | |
| LDLRAD3 | turquoise | gray | gray | turquoise | |
| XIST | turquoise | gray | turquoise | gray | |
| HLTF | turquoise | turquoise | turquoise | turquoise | |
| DMKN | black | magenta | black | black | |
| TNNC1 | turquoise | turquoise | turquoise | turquoise | |
| IL2RG | black | black | gray | black | |
| TMEM154 | black | gray | gray | black | |
| TPGS1 | black | black | gray | black | |
| GPC3 | black | gray | gray | black | |
| PRKCQ | black | black | black | black | |
| HP1BP3 | turquoise | gray | turquoise | turquoise | |
| SYT1 | turquoise | gray | gray | turquoise | |
| KCNMB4 | turquoise | turquoise | turquoise | turquoise | |
| NFIB | turquoise | gray | turquoise | turquoise | |
| RTN3 | turquoise | gray | gray | turquoise | |
| TSPAN5 | turquoise | turquoise | gray | turquoise | |
| XCL1 | black | black | black | gray | |
| TNFSF11 | turquoise | gray | gray | turquoise | |
| RUFY2 | black | gray | black | black | |
| FOXD1 | black | black | black | gray | |
| FREM1 | turquoise | turquoise | gray | gray | |
| RUNDC3B | turquoise | turquoise | turquoise | turquoise | |
| ZNF185 | turquoise | turquoise | turquoise | gray | |
| KIAA0125 | black | black | black | black | |
| PPL | turquoise | gray | turquoise | turquoise | |
| LMF1 | turquoise | gray | turquoise | turquoise | |
| FLRT3 | black | black | black | black | |
| LUZP1 | turquoise | turquoise | gray | turquoise | |
| SLC2A1 | turquoise | turquoise | gray | turquoise | |
| ARPC4 | black | gray | black | gray | |
| ABHD2 | turquoise | gray | turquoise | turquoise | |
| HHLA3 | black | gray | black | black | |
| EDN1 | turquoise | gray | gray | turquoise | |
| SATB1 | turquoise | turquoise | gray | turquoise | |
| RAPGEF4 | turquoise | turquoise | turquoise | turquoise | |
| DDX43 | turquoise | gray | gray | gray | |
| PSTPIP2 | turquoise | gray | gray | turquoise | |
| LEMD1 | turquoise | turquoise | gray | turquoise | |
| PVRL2 | turquoise | gray | gray | gray | |
| FRMD5 | black | black | gray | gray | |
| GAD1 | black | magenta | black | gray | |
| GSTZ1 | black | gray | black | gray | |
| MPI | black | gray | black | black | |
| KPNA6 | black | gray | gray | gray | |
| MOV10 | black | gray | black | gray | |
| UAP1L1 | black | gray | black | black | |
| CDK2AP2 | black | gray | black | gray | |
| LPCAT1 | black | magenta | black | gray | |
| BSG | black | gray | black | gray | |
| MIB2 | black | gray | black | gray | |
| TNFSF9 | black | gray | black | gray | |
| CBR3 | black | magenta | black | black | |
| ACIN1 | black | gray | black | gray | |
| AKT1 | black | gray | black | gray | |
| CALR | black | gray | black | black | |
| PFKP | black | gray | black | gray | |
| P4HB | black | gray | black | gray | |
| PKM | black | black | black | gray | |
| CDC42EP1 | black | gray | black | gray | |
| PFN1 | black | gray | black | gray | |
| RNF19B | black | gray | black | gray | |
| GPATCH2 | turquoise | gray | gray | turquoise | |
| HORMAD1 | turquoise | gray | gray | turquoise | |
| DSG3 | turquoise | turquoise | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| NPY1R | black | gray | gray | gray | |
| SIPA1L2 | turquoise | gray | gray | turquoise | |
| BRD2 | turquoise | gray | gray | gray | |
| IL27RA | black | gray | black | black | |
| IRF8 | black | black | black | black | |
| GALC | turquoise | turquoise | turquoise | turquoise | |
| TGFA | black | gray | gray | gray | |
| COCH | turquoise | gray | gray | turquoise | |
| IQGAP1 | turquoise | gray | gray | gray | |
| BAMBI | turquoise | turquoise | turquoise | turquoise | |
| NFYC | black | gray | black | gray | |
| CYP27B1 | black | black | black | black | |
| ZNF117 | turquoise | turquoise | turquoise | turquoise | |
| FAM76A | turquoise | gray | turquoise | turquoise | |
| NME5 | turquoise | turquoise | turquoise | turquoise | |
| CPLX1 | turquoise | turquoise | gray | turquoise | |
| INSM1 | black | magenta | black | black | |
| MGMT | turquoise | gray | turquoise | turquoise | |
| INSR | turquoise | gray | gray | turquoise | |
| ERAP2 | black | black | black | black | |
| CACHD1 | turquoise | turquoise | turquoise | turquoise | |
| CD44 | black | magenta | gray | black | |
| ZNF662 | turquoise | gray | gray | turquoise | |
| GNAS | turquoise | gray | gray | turquoise | |
| PTPRR | black | black | black | black | |
| HFE | black | gray | black | black | |
| PIWIL1 | black | magenta | black | gray | |
| CSRNP3 | turquoise | turquoise | turquoise | turquoise | |
| PKDCC | turquoise | turquoise | turquoise | turquoise | |
| GPR155 | turquoise | turquoise | gray | turquoise | |
| SKAP1 | black | gray | black | gray | |
| IGF1R | turquoise | gray | gray | turquoise | |
| FBXL16 | black | magenta | black | black | |
| SOX2 | turquoise | gray | gray | gray | |
| LAMP1 | turquoise | gray | gray | turquoise | |
| C10orf11 | turquoise | gray | gray | turquoise | |
| TNFRSF11B | turquoise | turquoise | turquoise | turquoise | |
| ROBO2 | turquoise | gray | gray | turquoise | |
| GSTT1 | black | black | gray | black | |
| SQSTM1 | turquoise | gray | gray | turquoise | |
| HPGD | black | black | gray | gray | |
| AFAP1L1 | black | gray | gray | gray | |
| MAGEA1 | black | black | black | black | |
| RBP4 | turquoise | turquoise | turquoise | turquoise | |
| S100A10 | turquoise | gray | gray | gray | |
| BMP4 | turquoise | gray | gray | turquoise | |
| CLN5 | black | gray | gray | gray | |
| PLEKHA2 | turquoise | gray | gray | turquoise | |
| TGFBI | turquoise | turquoise | gray | turquoise | |
| SPAG9 | turquoise | gray | turquoise | turquoise | |
| MSLN | turquoise | turquoise | turquoise | gray | |
| HBEGF | turquoise | gray | gray | turquoise | |
| IGF2BP3 | black | black | black | black | |
| PCP4 | turquoise | gray | gray | turquoise | |
| NHS | turquoise | turquoise | turquoise | turquoise | |
| TACSTD2 | turquoise | turquoise | turquoise | turquoise | |
| 2-Mar | black | magenta | gray | black | |
| STXBP1 | turquoise | gray | gray | turquoise | |
| ZNF655 | turquoise | gray | turquoise | turquoise | |
| TAGAP | black | black | gray | gray | |
| ID3 | turquoise | gray | gray | turquoise | |
| FGF18 | turquoise | turquoise | gray | turquoise | |
| GJB6 | turquoise | gray | gray | gray | |
| STEAP2 | turquoise | gray | gray | gray | |
| JUND | turquoise | gray | gray | turquoise | |
| SLC14A1 | turquoise | turquoise | turquoise | turquoise | |
| NPTX2 | turquoise | turquoise | turquoise | turquoise | |
| IGFBP1 | turquoise | turquoise | turquoise | turquoise | |
| F2RL2 | turquoise | gray | gray | turquoise | |
| BTBD11 | turquoise | turquoise | turquoise | turquoise | |
| GOLGA8A | turquoise | gray | turquoise | turquoise | |
| DNM3 | turquoise | turquoise | gray | turquoise | |
| KIF26A | turquoise | gray | turquoise | turquoise | |
| BTG2 | turquoise | gray | gray | turquoise | |
| CRD16 | black | black | black | black | |
| CASP1 | black | black | black | black | |

TABLE 5-continued

Genes for identification of subtypes and sub-subtypes

| | CCMS | ccs | CRCA1 | CRCA2 | potential 1 |
|---|---|---|---|---|---|
| NFATC2 | turquoise | turquoise | gray | turquoise | |
| KIAA1324L | turquoise | gray | turquoise | turquoise | |
| SORBS2 | turquoise | turquoise | turquoise | turquoise | |
| KLHL3 | turquoise | gray | gray | turquoise | |
| GSTM3 | turquoise | turquoise | turquoise | turquoise | |
| ZNF518B | turquoise | gray | gray | turquoise | |
| RASSF3 | turquoise | gray | turquoise | turquoise | |
| APLP2 | turquoise | gray | turquoise | turquoise | |
| NLRP2 | turquoise | turquoise | gray | turquoise | |
| SLFN13 | black | black | black | black | |
| NUB1 | black | black | black | black | |
| GABRB3 | turquoise | gray | gray | turquoise | |
| TTC9 | turquoise | turquoise | gray | turquoise | |
| FAM132B | turquoise | gray | gray | turquoise | |
| EPHA4 | turquoise | gray | gray | gray | |
| ZNF697 | turquoise | turquoise | gray | turquoise | |
| LAMP2 | black | gray | gray | gray | |
| FGF19 | turquoise | gray | turquoise | turquoise | |
| TMEM65 | turquoise | turquoise | turquoise | turquoise | |
| ABCA17P | black | gray | black | gray | |
| ALDH1A1 | turquoise | gray | gray | turquoise | |
| TMCO3 | black | gray | black | gray | |
| TMEM64 | black | black | black | gray | |
| PCED1A | turquoise | turquoise | gray | turquoise | |
| TMEM71 | turquoise | gray | turquoise | turquoise | |
| TFAP2C | black | black | black | gray | |
| PSD3 | turquoise | turquoise | turquoise | turquoise | |
| ZNF83 | turquoise | turquoise | turquoise | turquoise | |
| GATM | turquoise | turquoise | turquoise | turquoise | |
| FGF9 | turquoise | turquoise | gray | turquoise | |
| GSTA4 | turquoise | gray | turquoise | turquoise | |
| HOTAIR | black | black | black | gray | |
| PDE4A | turquoise | gray | turquoise | turquoise | |
| WNT5B | turquoise | gray | turquoise | turquoise | |
| HOXA1 | turquoise | turquoise | gray | gray | |
| CST3 | turquoise | gray | gray | turquoise | |
| CHGB | turquoise | turquoise | turquoise | turquoise | |
| TM4SF4 | turquoise | gray | gray | turquoise | |
| CD163L1 | black | black | black | black | |
| IL17RD | turquoise | turquoise | turquoise | turquoise | |
| SKAP2 | turquoise | turquoise | turquoise | gray | |
| STEAP1 | black | black | black | black | |
| ECHDC3 | turquoise | gray | turquoise | turquoise | |
| PGM2L1 | turquoise | turquoise | turquoise | turquoise | |
| FKBP11 | black | black | black | black | |
| ALCAM | turquoise | gray | gray | turquoise | |
| ZNF347 | turquoise | turquoise | turquoise | turquoise | |
| DNALI1 | turquoise | gray | turquoise | turquoise | |
| DDX58 | black | black | black | black | |
| HCP5 | black | black | black | gray | |
| RPL39L | turquoise | gray | turquoise | turquoise | |
| FABP3 | turquoise | gray | turquoise | turquoise | |
| APOLD1 | turquoise | gray | gray | turquoise | |
| CDC42 | black | gray | gray | gray | |
| GBP3 | black | black | black | black | |
| FBP1 | black | black | gray | black | |
| EHD4 | black | gray | gray | gray | |
| KRT80 | turquoise | turquoise | turquoise | turquoise | |
| OBSCN | turquoise | turquoise | gray | turquoise | |
| ADRB1 | black | magenta | black | gray | |
| EMB | black | black | gray | gray | |
| GZMB | black | black | black | black | |
| FGFR2 | turquoise | gray | gray | turquoise | |
| GLCCI1 | black | black | gray | black | |
| OSR2 | black | magenta | black | black | |
| ENPP1 | turquoise | turquoise | gray | turquoise | |
| ADPGK | black | gray | black | black | |
| CLIC3 | turquoise | turquoise | turquoise | turquoise | |
| PYROXD2 | turquoise | gray | gray | turquoise | |
| ZSWIM7 | black | black | black | black | |
| ABCG2 | black | gray | black | gray | |
| FRAS1 | turquoise | gray | turquoise | turquoise | |
| LEPROTL1 | black | gray | black | black | |
| GALNT10 | turquoise | turquoise | gray | turquoise | |
| DTNA | turquoise | turquoise | turquoise | turquoise | |
| TRIP6 | turquoise | gray | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| SMPX | turquoise | turquoise | gray | turquoise | |
| RHOF | black | black | black | gray | |
| ADRA2A | turquoise | turquoise | gray | turquoise | |
| SFTA2 | turquoise | turquoise | gray | turquoise | |
| SOX8 | turquoise | gray | turquoise | turquoise | |
| RGS13 | black | black | gray | gray | |
| ADAM22 | turquoise | turquoise | gray | turquoise | |
| DOCK11 | turquoise | turquoise | turquoise | turquoise | |
| KLK6 | turquoise | turquoise | turquoise | turquoise | |
| AKIRIN2 | black | gray | black | gray | |
| CDKN1A | black | black | gray | gray | |
| B4GALT1 | black | gray | black | gray | |
| ITGA9 | turquoise | gray | gray | turquoise | |
| CTSS | black | gray | black | black | |
| KLF13 | black | black | black | black | |
| TMCC3 | black | gray | black | gray | |
| RASGEF1A | black | black | black | gray | |
| LGALS8 | black | black | black | black | |
| ADAMTS15 | turquoise | gray | gray | turquoise | |
| HOXD10 | turquoise | turquoise | gray | turquoise | |
| HOXD11 | turquoise | turquoise | gray | turquoise | |
| OSBPL8 | turquoise | turquoise | gray | turquoise | |
| S100A2 | turquoise | turquoise | turquoise | turquoise | |
| ZNF559 | turquoise | turquoise | turquoise | turquoise | |
| FRZB | turquoise | gray | gray | turquoise | |
| CALB1 | black | black | black | black | |
| GUCY1A2 | turquoise | turquoise | turquoise | gray | |
| METRN | black | magenta | black | gray | |
| SLC46A3 | turquoise | turquoise | gray | turquoise | |
| ARAP3 | turquoise | turquoise | turquoise | turquoise | |
| MPP1 | turquoise | gray | gray | turquoise | |
| IGHD | black | black | gray | gray | |
| GIMAP2 | black | black | black | black | |
| C3orf70 | turquoise | turquoise | turquoise | turquoise | |
| PGBD5 | turquoise | gray | gray | turquoise | |
| ARHGEF6 | turquoise | gray | turquoise | turquoise | |
| SNCAIP | turquoise | turquoise | turquoise | turquoise | |
| HBB | turquoise | gray | turquoise | gray | |
| NT5E | black | magenta | black | black | |
| INTU | turquoise | turquoise | gray | turquoise | |
| ENAH | turquoise | turquoise | turquoise | turquoise | |
| POPDC3 | turquoise | gray | turquoise | turquoise | |
| ST6GALNAC2 | black | magenta | black | gray | |
| SSR3 | black | gray | black | black | |
| SEMA3A | turquoise | turquoise | gray | turquoise | |
| NRN1 | turquoise | gray | gray | turquoise | |
| ADAM17 | turquoise | gray | gray | turquoise | |
| LAMA3 | black | gray | black | black | |
| HHIP | turquoise | gray | turquoise | turquoise | |
| IRAK2 | black | black | gray | gray | |
| HIST2H2BE | turquoise | turquoise | turquoise | turquoise | |
| MLF1 | turquoise | turquoise | turquoise | turquoise | |
| NR4A2 | black | black | black | gray | |
| CRAT | turquoise | turquoise | gray | turquoise | |
| DDIT4 | turquoise | gray | gray | turquoise | |
| PLIN2 | turquoise | turquoise | turquoise | turquoise | |
| PDE10A | black | gray | black | black | |
| FAM228B | turquoise | turquoise | gray | turquoise | |
| IBSP | turquoise | gray | gray | gray | |
| LEPREL1 | turquoise | turquoise | turquoise | turquoise | |
| THRB | turquoise | turquoise | gray | turquoise | |
| OPN3 | turquoise | turquoise | gray | turquoise | |
| EPB41L4A | turquoise | turquoise | turquoise | turquoise | |
| SNCA | turquoise | turquoise | turquoise | turquoise | |
| MAN1A1 | turquoise | gray | turquoise | turquoise | |
| CDA | turquoise | turquoise | turquoise | turquoise | |
| SERPINE2 | turquoise | turquoise | gray | turquoise | |
| GLUD2 | black | gray | gray | gray | |
| MMP1 | turquoise | gray | turquoise | gray | |
| MMP3 | turquoise | gray | turquoise | gray | |
| ETV6 | black | gray | black | gray | |
| KRT6B | turquoise | turquoise | turquoise | turquoise | |
| COPA | turquoise | turquoise | gray | turquoise | |
| ZC2HC1A | turquoise | turquoise | gray | turquoise | |
| SMARCA2 | turquoise | gray | turquoise | turquoise | |
| PHLDA1 | turquoise | gray | gray | turquoise | |

TABLE 5-continued

Genes for identification of subtypes and sub-subtypes

| | CCMS | ccs | CRCA1 | CRCA2 | potential 1 |
|---|---|---|---|---|---|
| NQO2 | black | gray | black | black | |
| N4BP2L1 | black | black | gray | gray | |
| ANKRD29 | turquoise | turquoise | turquoise | turquoise | |
| DDX60L | black | black | black | black | |
| TLR3 | black | black | black | black | |
| TNFSF10 | black | black | black | black | |
| IK2F2 | black | black | black | black | |
| PLCL2 | black | magenta | black | black | |
| RAB27A | black | magenta | black | black | |
| PCDHB14 | turquoise | turquoise | turquoise | turquoise | |
| CNTLN | black | gray | black | gray | |
| FAM13A-AS1 | turquoise | gray | gray | gray | |
| DEDD | turquoise | gray | turquoise | turquoise | |
| TNFRSF19 | turquoise | turquoise | turquoise | turquoise | |
| PRKAA2 | turquoise | turquoise | turquoise | turquoise | |
| ADSSL1 | turquoise | gray | gray | turquoise | |
| SRPX2 | turquoise | turquoise | gray | turquoise | |
| SNX19 | turquoise | gray | turquoise | turquoise | |
| CCL26 | turquoise | gray | gray | gray | |
| PELI2 | turquoise | turquoise | turquoise | turquoise | |
| ITGB1BP1 | turquoise | gray | gray | turquoise | |
| EFNA5 | turquoise | gray | gray | turquoise | |
| PRSS23 | turquoise | gray | gray | turquoise | |
| ELP5 | black | gray | black | black | |
| MMP7 | turquoise | turquoise | turquoise | turquoise | |
| VLDLR | turquoise | turquoise | turquoise | turquoise | |
| TMEM220 | black | black | black | black | |
| ARRDC4 | turquoise | turquoise | turquoise | turquoise | |
| INPP5A | turquoise | gray | gray | turquoise | |
| CTSH | turquoise | gray | gray | turquoise | |
| P4HA1 | black | black | black | black | |
| FHOD3 | turquoise | gray | gray | turquoise | |
| JAG1 | turquoise | gray | gray | turquoise | |
| TAC1 | turquoise | gray | gray | turquoise | |
| TJP1 | turquoise | gray | turquoise | turquoise | |
| TRNP1 | black | magenta | black | gray | |
| ULBP2 | black | magenta | black | gray | |
| NELL2 | turquoise | gray | gray | turquoise | |
| ARHGAP4 | black | black | black | black | |
| RASAL2 | turquoise | gray | gray | turquoise | |
| PBX1 | turquoise | turquoise | gray | turquoise | |
| PARVB | turquoise | gray | gray | turquoise | |
| SPRR1A | black | gray | black | black | |
| SPRR1B | turquoise | gray | gray | gray | |
| SPRR3 | turquoise | turquoise | turquoise | gray | |
| MBD1 | black | gray | black | gray | |
| IER5 | black | magenta | black | black | |
| RBP1 | turquoise | turquoise | turquoise | turquoise | |
| PTGES | turquoise | gray | turquoise | turquoise | |
| GALNT18 | turquoise | gray | turquoise | turquoise | |
| WT1 | turquoise | turquoise | turquoise | turquoise | |
| ATF3 | turquoise | gray | gray | turquoise | |
| NR4A1 | turquoise | gray | gray | turquoise | |
| FOS | turquoise | gray | turquoise | turquoise | |
| JUNB | turquoise | gray | turquoise | turquoise | |
| ZFP36 | turquoise | gray | turquoise | turquoise | |
| STAT3 | turquoise | gray | turquoise | turquoise | |
| ZNF415 | turquoise | turquoise | turquoise | turquoise | |
| KRT7 | black | magenta | black | gray | |
| TAPBP | black | gray | black | black | |
| KLK10 | black | black | gray | gray | |
| PPBP | turquoise | gray | turquoise | turquoise | |
| DYNC1H1 | turquoise | gray | gray | turquoise | |
| NAGA | black | gray | black | gray | |
| ZMAT1 | turquoise | turquoise | turquoise | turquoise | |
| TACC1 | turquoise | turquoise | gray | turquoise | |
| TBL1X | turquoise | gray | gray | turquoise | |
| SOD3 | turquoise | turquoise | turquoise | turquoise | |
| HEXIM1 | black | black | black | gray | |
| TET1 | turquoise | turquoise | turquoise | turquoise | |
| PEG10 | turquoise | gray | turquoise | turquoise | |
| DENND5B | black | black | gray | gray | |
| DKK1 | turquoise | turquoise | turquoise | turquoise | |
| ZNF329 | turquoise | turquoise | turquoise | turquoise | |
| C4orf32 | black | black | black | black | |
| LYN | black | black | gray | gray | |

TABLE 5-continued

Genes for identification of subtypes and sub-subtypes

| | CCMS | ccs | CRCA1 | CRCA2 | potential 1 |
|---|---|---|---|---|---|
| NRXN3 | turquoise | turquoise | turquoise | turquoise | |
| EXOC6B | turquoise | gray | turquoise | turquoise | |
| LOXL1-AS1 | turquoise | gray | gray | turquoise | |
| WASF3 | turquoise | turquoise | gray | turquoise | |
| DMD | turquoise | turquoise | gray | turquoise | |
| SAR1A | turquoise | gray | gray | turquoise | |
| TGFBR3 | turquoise | turquoise | gray | turquoise | |
| MUM1 | turquoise | gray | gray | turquoise | |
| SESTD1 | turquoise | gray | gray | turquoise | |
| ODAM | turquoise | turquoise | turquoise | turquoise | |
| OR51E1 | turquoise | turquoise | turquoise | turquoise | |
| TSHZ2 | turquoise | turquoise | gray | turquoise | |
| P2RX5 | black | black | black | black | |
| TMC8 | black | black | black | black | |
| DPP7 | turquoise | gray | gray | gray | |
| SPIRE1 | turquoise | gray | turquoise | turquoise | |
| ERO1LB | black | black | black | black | |
| PAX5 | black | black | black | black | |
| LAMC2 | turquoise | turquoise | turquoise | turquoise | |
| LYZ | black | black | black | black | |
| FOSL2 | black | gray | gray | gray | |
| NEFL | turquoise | turquoise | turquoise | turquoise | |
| ALKBH5 | black | gray | black | gray | |
| MKX | turquoise | turquoise | turquoise | turquoise | |
| SLC16A3 | black | gray | black | black | |
| AFAP1L2 | black | magenta | black | black | |
| PPP1R3B | turquoise | gray | turquoise | turquoise | |
| CYP2U1 | turquoise | turquoise | turquoise | turquoise | |
| LPAR6 | turquoise | turquoise | turquoise | turquoise | |
| FAM107B | black | black | black | black | |
| KRT6A | turquoise | turquoise | turquoise | turquoise | |
| FGF13 | turquoise | turquoise | gray | turquoise | |
| SCEL | turquoise | turquoise | turquoise | turquoise | |
| DST | turquoise | gray | turquoise | turquoise | |
| SALL4 | turquoise | turquoise | gray | turquoise | |
| TGFBR2 | turquoise | gray | gray | turquoise | |
| SST | turquoise | gray | turquoise | turquoise | |
| FNDC3B | turquoise | gray | turquoise | turquoise | |
| TUBB2B | turquoise | turquoise | turquoise | turquoise | |
| ZMAT3 | turquoise | turquoise | gray | turquoise | |
| SERPINA3 | turquoise | gray | turquoise | turquoise | |
| FLCN | black | gray | black | black | |
| PFN2 | turquoise | turquoise | turquoise | turquoise | |
| SLCO3A1 | turquoise | turquoise | turquoise | turquoise | |
| AHR | black | magenta | gray | gray | |
| COL27A1 | turquoise | gray | turquoise | turquoise | |
| SERTAD4 | turquoise | turquoise | turquoise | turquoise | |
| ANPEP | black | black | black | black | |
| SOCS1 | black | black | black | black | |
| F5 | black | black | gray | gray | |
| SLC16A10 | turquoise | gray | gray | turquoise | |
| AIF1L | black | black | black | gray | |
| GABBR1 | turquoise | gray | gray | turquoise | |
| FGD6 | black | black | black | gray | |
| ADM | black | black | black | black | |
| ARRDC3 | turquoise | turquoise | turquoise | turquoise | |
| RHOD | turquoise | turquoise | turquoise | turquoise | |
| IL1B | black | black | black | black | |
| PROK2 | black | black | black | black | |
| CXCL5 | turquoise | gray | gray | turquoise | |
| IL24 | turquoise | gray | turquoise | turquoise | |
| FFAR2 | black | black | black | black | |
| CDKN2A | turquoise | turquoise | turquoise | turquoise | |
| LAIR2 | black | black | black | black | |
| IRF5 | turquoise | gray | turquoise | turquoise | |
| HSPA12A | turquoise | turquoise | turquoise | turquoise | |
| LDLRAD4 | turquoise | gray | gray | turquoise | |
| CXCL6 | turquoise | gray | turquoise | gray | |
| SLC22A4 | turquoise | gray | turquoise | turquoise | |
| PROS1 | turquoise | turquoise | turquoise | turquoise | |
| ARHGAP6 | turquoise | turquoise | turquoise | turquoise | |
| TYRP1 | turquoise | gray | turquoise | turquoise | |
| PYGL | black | black | black | black | |
| PDE3A | turquoise | turquoise | gray | turquoise | |
| BNIP3 | turquoise | turquoise | turquoise | turquoise | |
| CDC42BPA | turquoise | turquoise | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| RAB30 | turquoise | turquoise | turquoise | turquoise | |
| NOTCH2NL | turquoise | turquoise | turquoise | turquoise | |
| LTF | black | gray | gray | black | |
| 11-Sep | turquoise | gray | gray | turquoise | |
| EVA1A | turquoise | turquoise | gray | turquoise | |
| TM4SF1 | turquoise | gray | turquoise | turquoise | |
| MRPS21 | black | black | black | black | |
| WWC3 | turquoise | turquoise | gray | turquoise | |
| LPL | turquoise | turquoise | turquoise | turquoise | |
| SLC16A4 | turquoise | turquoise | turquoise | turquoise | |
| KLF7 | turquoise | turquoise | gray | turquoise | |
| MICB | black | magenta | black | black | |
| PDK4 | turquoise | turquoise | turquoise | turquoise | |
| IGF2 | turquoise | turquoise | turquoise | turquoise | |
| ADA | black | black | black | black | |
| PARP8 | black | black | black | black | |
| FAM127B | turquoise | gray | gray | turquoise | |
| UCP2 | black | black | black | black | |
| FAM120C | turquoise | turquoise | gray | turquoise | |
| C3orf14 | turquoise | turquoise | turquoise | turquoise | |
| RHOBTB1 | turquoise | turquoise | turquoise | turquoise | |
| SACS | turquoise | gray | gray | turquoise | |
| GNA15 | black | black | black | black | |
| SCG5 | turquoise | gray | turquoise | turquoise | |
| MAGED1 | turquoise | turquoise | gray | turquoise | |
| SOCS2 | turquoise | gray | gray | turquoise | |
| TLR4 | turquoise | gray | turquoise | turquoise | |
| FKBP5 | black | gray | black | gray | |
| SAMD3 | black | black | black | black | |
| IGHG1 | black | black | black | black | |
| FAM46C | black | black | black | black | |
| ANKRD36BP2 | black | black | black | black | |
| KLRB1 | black | black | black | black | |
| IGJ | black | black | black | black | |
| FCRL5 | black | black | black | black | |
| CD79A | black | black | black | black | |
| PNOC | black | black | gray | black | |
| IGHM | black | black | black | black | |
| IGKC | black | black | black | black | |
| DERL3 | black | black | black | black | |
| TNFRSF17 | black | black | black | black | |
| POU2AF1 | black | black | black | black | |
| GUSBP11 | black | black | black | black | |
| IGLL3P | black | black | black | black | |
| MZB1 | black | black | black | black | |
| PTK7 | turquoise | gray | turquoise | turquoise | |
| MAP3K6 | black | magenta | black | gray | |
| PPFIBP1 | black | gray | gray | gray | |
| COL4A4 | turquoise | turquoise | turquoise | turquoise | |
| DUSP3 | turquoise | gray | gray | turquoise | |
| CP | black | black | black | gray | |
| CERK | turquoise | turquoise | gray | turquoise | |
| SMOC2 | turquoise | turquoise | turquoise | turquoise | |
| RARRES1 | black | black | black | black | |
| SAV1 | black | black | black | gray | |
| MT1M | black | black | black | black | |
| MT1E | black | black | black | black | |
| MT2A | black | black | black | black | |
| MT1F | black | black | black | black | |
| MT1H | black | black | black | black | |
| MT1G | black | black | black | black | |
| MT1X | black | black | black | black | |
| SLC2A10 | turquoise | turquoise | turquoise | turquoise | |
| STMN3 | turquoise | gray | turquoise | turquoise | |
| SGCB | turquoise | gray | gray | turquoise | |
| SERPINI1 | turquoise | turquoise | turquoise | turquoise | |
| RARA | turquoise | gray | gray | turquoise | |
| CIRBP | turquoise | gray | gray | turquoise | |
| EVC | turquoise | turquoise | turquoise | turquoise | |
| GNAI1 | turquoise | turquoise | turquoise | turquoise | |
| PLA2G16 | turquoise | turquoise | gray | turquoise | |
| PTGS2 | turquoise | gray | turquoise | turquoise | |
| CXCL16 | black | black | black | black | |
| LEPREL4 | turquoise | gray | turquoise | turquoise | |
| KIT | turquoise | gray | gray | turquoise | |
| SMIM3 | turquoise | turquoise | gray | turquoise | |

TABLE 5-continued

Genes for identification of subtypes and sub-subtypes

| | CCMS | ccs | CRCA1 | CRCA2 | potential 1 |
|---|---|---|---|---|---|
| TMEM173 | black | black | gray | gray | |
| SLC9B2 | turquoise | gray | gray | turquoise | |
| ST20 | black | gray | gray | black | |
| BMPR1B | turquoise | turquoise | turquoise | turquoise | |
| KCTD1 | black | black | black | gray | |
| ZFP37 | turquoise | turquoise | gray | turquoise | |
| B2M | black | black | black | gray | |
| PNMA2 | black | black | black | gray | |
| MMP12 | black | black | black | black | |
| NOV | turquoise | turquoise | turquoise | turquoise | |
| CHFR | turquoise | gray | turquoise | turquoise | |
| SLFN5 | turquoise | gray | gray | gray | |
| CCDC109B | black | magenta | black | black | |
| BCL2 | black | black | black | black | |
| BTN3A2 | black | black | black | black | |
| IL32 | black | black | black | gray | |
| STK17B | black | black | black | black | |
| FAS | black | magenta | black | black | |
| IL15 | black | black | black | black | |
| BIRC3 | black | black | black | black | |
| STK17A | black | black | black | black | |
| JAK2 | black | black | black | black | |
| TNFAIP8 | black | black | black | black | |
| FBXO6 | black | black | black | black | |
| EPSTI1 | black | black | black | black | |
| RNF213 | black | gray | black | black | |
| BATF2 | black | black | black | gray | |
| PSMB10 | black | gray | black | black | |
| ISG20 | black | black | black | black | |
| IFI27 | black | black | black | black | |
| OASL | black | black | black | black | |
| SECTM1 | black | black | black | black | |
| HLA-F | black | black | black | black | |
| IFIT5 | black | black | black | black | |
| IFI6 | black | black | black | black | |
| ETV7 | black | black | black | gray | |
| APOL6 | black | black | black | black | |
| RTP4 | black | black | black | black | |
| DDX60 | black | black | black | black | |
| SAMD9 | black | black | black | black | |
| AIM2 | black | black | black | black | |
| TAP2 | black | black | black | black | |
| LAMP3 | black | black | black | black | |
| CXCL11 | black | black | black | black | |
| NLRC5 | black | black | black | black | |
| ODF3B | black | black | black | black | |
| TRIM69 | black | black | black | black | |
| IRF7 | black | black | black | black | |
| IFIH1 | black | black | black | black | |
| MX2 | black | black | black | black | |
| OAS3 | black | black | black | black | |
| IFI35 | black | black | black | black | |
| USP18 | black | black | black | black | |
| HERC6 | black | black | black | black | |
| ISG15 | black | black | black | black | |
| PARP14 | black | black | black | black | |
| PARP9 | black | black | black | black | |
| SAMD9L | black | black | black | black | |
| XAF1 | black | black | black | black | |
| IFIT1 | black | black | gray | gray | |
| IFI72 | black | black | black | black | |
| RSAD2 | black | black | black | black | |
| IFI44 | black | black | black | black | |
| CMPK2 | black | black | black | black | |
| OAS2 | black | black | black | black | |
| IFI44L | black | black | black | black | |
| IFIT3 | black | black | black | black | |
| MX1 | black | black | black | black | |
| IRF9 | black | black | black | black | |
| LAP3 | black | black | black | black | |
| WARS | black | black | black | black | |
| IRF1 | black | black | black | black | |
| PSM89 | black | black | black | black | |
| TAP1 | black | black | black | black | |
| STAT1 | black | black | black | black | |
| UBE2L6 | black | black | black | black | |

TABLE 5-continued

Genes for identification of subtypes and sub-subtypes

| | CCMS | ccs | CRCA1 | CRCA2 | potential 1 |
|---|---|---|---|---|---|
| PKIA | turquoise | turquoise | turquoise | turquoise | |
| SLCO2A1 | turquoise | gray | turquoise | turquoise | |
| MAST4 | turquoise | turquoise | turquoise | turquoise | |
| CGNL1 | turquoise | turquoise | turquoise | turquoise | |
| SLC7A2 | turquoise | turquoise | turquoise | turquoise | |
| SERPINB2 | black | black | gray | gray | |
| CTLA4 | black | black | black | black | |
| MAFF | turquoise | gray | gray | turquoise | |
| PDGFD | turquoise | turquoise | turquoise | turquoise | |
| TUBB2A | black | black | black | gray | |
| EPHA7 | turquoise | turquoise | turquoise | turquoise | |
| GHR | turquoise | turquoise | turquoise | turquoise | |
| PCDH18 | turquoise | gray | turquoise | turquoise | |
| FOXF2 | turquoise | gray | turquoise | turquoise | |
| NKX2-3 | turquoise | gray | turquoise | turquoise | |
| SYNGR3 | black | black | black | gray | |
| TRERF1 | black | black | black | gray | |
| S100A13 | turquoise | gray | turquoise | turquoise | |
| LIMCH1 | turquoise | turquoise | turquoise | turquoise | |
| BNIP3L | black | black | black | gray | |
| EVA1C | turquoise | turquoise | gray | turquoise | |
| LAMA5 | turquoise | turquoise | turquoise | turquoise | |
| EDNRB | turquoise | gray | turquoise | turquoise | |
| BANK1 | black | black | black | black | |
| ZNF300 | turquoise | turquoise | turquoise | turquoise | |
| HOXD4 | turquoise | turquoise | gray | turquoise | |
| CST1 | turquoise | turquoise | turquoise | turquoise | |
| CST4 | turquoise | turquoise | turquoise | turquoise | |
| FOXP2 | turquoise | turquoise | gray | turquoise | |
| ZNF134 | turquoise | turquoise | turquoise | turquoise | |
| ARNT2 | turquoise | gray | gray | turquoise | |
| MUM1L1 | turquoise | turquoise | turquoise | turquoise | |
| SCRN1 | turquoise | turquoise | turquoise | turquoise | |
| ZNF880 | turquoise | turquoise | turquoise | turquoise | |
| NINL | turquoise | gray | gray | turquoise | |
| PCNX | turquoise | gray | gray | turquoise | |
| ARHGAP28 | turquoise | turquoise | turquoise | turquoise | |
| TP53INP2 | turquoise | gray | turquoise | turquoise | |
| CFD | black | black | black | black | |
| SNX20 | black | black | black | black | |
| ERRFI1 | turquoise | gray | gray | turquoise | |
| MEGF6 | turquoise | turquoise | gray | turquoise | |
| RAI2 | turquoise | turquoise | turquoise | turquoise | |
| FAXC | turquoise | turquoise | turquoise | turquoise | |
| CASP4 | black | black | black | black | |
| LCK | black | black | black | black | |
| NCALD | turquoise | gray | turquoise | turquoise | |
| CR2 | black | black | gray | black | |
| MS4A1 | black | black | black | black | |
| BAG3 | turquoise | gray | gray | turquoise | |
| FMO3 | turquoise | gray | turquoise | turquoise | |
| SLC16A7 | turquoise | turquoise | gray | turquoise | |
| TXNIP | turquoise | turquoise | gray | turquoise | |
| LXN | black | gray | black | black | |
| ACSL1 | turquoise | gray | turquoise | turquoise | |
| GLUL | black | black | black | black | |
| HSPA2 | turquoise | turquoise | turquoise | turquoise | |
| EGFL6 | turquoise | gray | turquoise | gray | |
| TEAD2 | turquoise | gray | turquoise | turquoise | |
| TLE4 | turquoise | turquoise | turquoise | turquoise | |
| CC2D2A | turquoise | turquoise | turquoise | turquoise | |
| ELL2 | black | black | black | black | |
| PIK3R5 | black | black | black | gray | |
| DUSP10 | turquoise | gray | gray | turquoise | |
| ANO1 | turquoise | gray | gray | turquoise | |
| KCNS3 | turquoise | turquoise | gray | turquoise | |
| PCDHB2 | turquoise | turquoise | turquoise | turquoise | |
| HOXC6 | black | black | black | black | |
| LRMP | black | black | black | black | |
| FTH1 | black | gray | gray | gray | |
| SPATS2L | black | gray | black | gray | |
| ZFP82 | turquoise | turquoise | turquoise | turquoise | |
| FBN2 | turquoise | turquoise | turquoise | turquoise | |
| PDZD2 | turquoise | gray | turquoise | turquoise | |
| TMEM200A | turquoise | turquoise | turquoise | turquoise | |
| L1CAM | turquoise | turquoise | gray | turquoise | |

TABLE 5-continued

Genes for identification of subtypes and sub-subtypes

| | CCMS | ccs | CRCA1 | CRCA2 | potential 1 |
|---|---|---|---|---|---|
| BHLHE40 | turquoise | gray | turquoise | turquoise | |
| CAPG | black | black | black | black | |
| ULK2 | turquoise | turquoise | turquoise | turquoise | |
| PDLIM5 | turquoise | turquoise | gray | turquoise | |
| RBM24 | turquoise | turquoise | turquoise | turquoise | |
| RAB3B | turquoise | gray | turquoise | turquoise | |
| UBASH3B | black | black | black | black | |
| SNX24 | turquoise | gray | gray | gray | |
| GAS2L1 | black | black | black | gray | |
| HOTAIRM1 | turquoise | turquoise | turquoise | turquoise | |
| CPE | turquoise | turquoise | gray | turquoise | |
| LY6E | black | black | black | black | |
| FKBP1A | turquoise | gray | turquoise | turquoise | |
| CD1D | black | black | black | gray | |
| ST6GAL2 | turquoise | turquoise | gray | turquoise | |
| PTPN21 | turquoise | turquoise | turquoise | turquoise | |
| NGFRAP1 | turquoise | turquoise | turquoise | turquoise | |
| RIN2 | turquoise | gray | turquoise | turquoise | |
| FPR2 | black | black | black | black | |
| INHBB | turquoise | turquoise | turquoise | turquoise | |
| LYST | turquoise | turquoise | gray | turquoise | |
| APOL1 | black | black | black | black | |
| FOXC1 | turquoise | turquoise | turquoise | turquoise | |
| EGR1 | turquoise | turquoise | turquoise | turquoise | |
| TFPI2 | turquoise | turquoise | turquoise | turquoise | |
| IGFL2 | turquoise | turquoise | turquoise | turquoise | |
| CDH19 | turquoise | turquoise | turquoise | turquoise | |
| ZKSCAN7 | turquoise | turquoise | turquoise | turquoise | |
| RAB38 | black | black | black | gray | |
| GAP43 | turquoise | turquoise | turquoise | turquoise | |
| CFI | turquoise | turquoise | turquoise | turquoise | |
| AOX1 | turquoise | turquoise | turquoise | turquoise | |
| HAS2 | turquoise | gray | turquoise | turquoise | |
| GAS6 | turquoise | turquoise | turquoise | turquoise | |
| PPM1K | black | black | black | black | |
| IL1RAP | turquoise | gray | turquoise | turquoise | |
| PLOD2 | turquoise | turquoise | turquoise | turquoise | |
| OGFRL1 | black | black | black | black | |
| TRIL | turquoise | turquoise | turquoise | turquoise | |
| GRB10 | turquoise | turquoise | turquoise | turquoise | |
| ASPA | turquoise | turquoise | turquoise | turquoise | |
| WNT5A | turquoise | turquoise | turquoise | turquoise | |
| PCDHB16 | turquoise | turquoise | turquoise | turquoise | |
| C9orf3 | turquoise | gray | turquoise | turquoise | |
| CARD6 | black | gray | gray | gray | |
| FCER1A | turquoise | turquoise | turquoise | turquoise | |
| CTSC | black | black | black | black | |
| GREM2 | turquoise | gray | turquoise | turquoise | |
| KCTD15 | turquoise | turquoise | gray | turquoise | |
| OSBPL1A | turquoise | turquoise | gray | turquoise | |
| CX3CL1 | black | black | black | black | |
| MARCKS | turquoise | gray | gray | turquoise | |
| HES4 | turquoise | gray | gray | turquoise | |
| IKZF1 | black | black | black | black | |
| GAA | turquoise | gray | gray | turquoise | |
| FBXL2 | turquoise | turquoise | turquoise | turquoise | |
| MCL1 | turquoise | gray | gray | turquoise | |
| MR1 | black | gray | black | black | |
| TMEM163 | turquoise | turquoise | turquoise | gray | |
| CXCR2 | black | black | black | black | |
| TLR7 | black | gray | gray | black | |
| GLIS3 | turquoise | turquoise | turquoise | turquoise | |
| FOSB | turquoise | gray | turquoise | turquoise | |
| MAP3K8 | black | black | black | black | |
| FAM43A | turquoise | gray | gray | turquoise | |
| RHOB | turquoise | gray | gray | turquoise | |
| CST2 | turquoise | turquoise | turquoise | turquoise | |
| CPM | black | gray | black | gray | |
| WASF1 | turquoise | gray | gray | turquoise | |
| CPNE8 | turquoise | turquoise | turquoise | turquoise | |
| FAIM3 | black | black | black | black | |
| CLC | black | black | gray | black | |
| GRK5 | turquoise | turquoise | turquoise | turquoise | |
| FDCSP | black | black | gray | black | |
| SQAT1 | turquoise | gray | turquoise | turquoise | |
| ENO2 | turquoise | gray | gray | turquoise | |

TABLE 5-continued

Genes for identification of subtypes and sub-subtypes

| | CCMS | ccs | CRCA1 | CRCA2 | potential 1 |
|---|---|---|---|---|---|
| MAGI2 | turquoise | turquoise | turquoise | turquoise | |
| SDC3 | turquoise | gray | gray | turquoise | |
| MIAT | black | black | black | black | |
| ADAM28 | black | black | black | black | |
| SLC11A1 | black | black | gray | gray | |
| FZD7 | turquoise | turquoise | turquoise | turquoise | |
| RGS5 | turquoise | gray | turquoise | turquoise | |
| CNN3 | turquoise | gray | gray | turquoise | |
| MAX | black | gray | black | black | |
| S100A12 | black | black | black | black | |
| PTPLA | turquoise | gray | turquoise | turquoise | |
| SLC2A5 | black | black | black | black | |
| RNASE1 | black | black | black | gray | |
| ANGPT2 | turquoise | gray | turquoise | turquoise | |
| KLF12 | turquoise | turquoise | turquoise | turquoise | |
| NLGN4X | turquoise | turquoise | turquoise | turquoise | |
| ZNF618 | turquoise | gray | gray | turquoise | |
| HERC5 | black | gray | gray | gray | |
| DAB2 | turquoise | turquoise | gray | turquoise | |
| PLK2 | turquoise | gray | gray | turquoise | |
| NUPR1 | turquoise | turquoise | gray | turquoise | |
| F8 | turquoise | turquoise | turquoise | turquoise | |
| LEPR | turquoise | turquoise | turquoise | turquoise | |
| SERPINB9 | black | black | gray | black | |
| DYNC2H1 | turquoise | turquoise | turquoise | turquoise | |
| RNF217 | turquoise | turquoise | turquoise | turquoise | |
| GNAL | turquoise | turquoise | turquoise | turquoise | |
| PELO | turquoise | turquoise | gray | gray | |
| C16orf54 | black | black | black | black | |
| STMN2 | turquoise | turquoise | turquoise | turquoise | |
| CEBPD | black | black | black | black | |
| MERTK | black | gray | gray | gray | |
| HLA-DQA1 | black | black | black | black | |
| ETV5 | turquoise | gray | gray | turquoise | |
| B3GALNT1 | turquoise | turquoise | turquoise | turquoise | |
| CH25H | turquoise | gray | turquoise | turquoise | |
| ETV1 | turquoise | turquoise | gray | turquoise | |
| PCOLCE2 | turquoise | turquoise | turquoise | turquoise | |
| FAM114A1 | turquoise | gray | gray | turquoise | |
| RILPL2 | black | black | black | black | |
| TMEM35 | turquoise | turquoise | turquoise | turquoise | |
| PHACTR1 | black | black | black | black | |
| SLC20A1 | turquoise | gray | gray | turquoise | |
| RAB12 | black | black | black | gray | |
| TMOD2 | turquoise | turquoise | turquoise | turquoise | |
| UGCG | turquoise | gray | gray | turquoise | |
| ATL1 | turquoise | turquoise | gray | turquoise | |
| OPTN | black | gray | black | black | |
| C16orf62 | turquoise | gray | turquoise | turquoise | |
| KCND3 | turquoise | gray | turquoise | turquoise | |
| SNX10 | black | black | black | black | |
| HOXD8 | turquoise | turquoise | gray | turquoise | |
| HHEX | black | black | black | gray | |
| LDB3 | turquoise | turquoise | turquoise | turquoise | |
| APBB2 | turquoise | gray | gray | turquoise | |
| ADAMTS9 | turquoise | turquoise | turquoise | turquoise | |
| LMO4 | black | black | black | black | |
| GJB2 | turquoise | turquoise | gray | turquoise | |
| MYOF | turquoise | turquoise | gray | turquoise | |
| CR1 | black | black | gray | black | |
| SORBS1 | turquoise | turquoise | gray | turquoise | |
| CTSZ | black | black | gray | gray | |
| RPS6KA2 | turquoise | turquoise | gray | turquoise | |
| PRKAR2B | black | black | gray | black | |
| PLEKHH2 | turquoise | turquoise | turquoise | turquoise | |
| FKBP14 | turquoise | turquoise | turquoise | turquoise | |
| NFKBIA | black | black | black | black | |
| ACSS3 | turquoise | turquoise | turquoise | turquoise | |
| TOX2 | black | black | black | black | |
| S100A9 | black | black | black | black | |
| ATL3 | turquoise | gray | gray | turquoise | |
| TPBG | turquoise | gray | gray | turquoise | |
| LAMB1 | turquoise | turquoise | turquoise | turquoise | |
| SCUBE3 | turquoise | turquoise | gray | turquoise | |
| IRS1 | turquoise | turquoise | turquoise | turquoise | |
| ST3GAL1 | turquoise | gray | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| TGM2 | black | black | black | gray | |
| NBEA | turquoise | turquoise | turquoise | turquoise | |
| LRP12 | turquoise | turquoise | turquoise | turquoise | |
| COL21A1 | turquoise | turquoise | turquoise | turquoise | |
| HDAC9 | turquoise | turquoise | turquoise | turquoise | |
| PER3 | turquoise | turquoise | gray | turquoise | |
| ADIPOQ | turquoise | turquoise | turquoise | turquoise | |
| EGR3 | turquoise | gray | turquoise | turquoise | |
| UST | turquoise | turquoise | gray | turquoise | |
| RNF144B | black | black | black | black | |
| ENPEP | turquoise | turquoise | turquoise | turquoise | |
| SLC16A6 | black | black | black | black | |
| S100B | black | black | black | gray | |
| BHLHE41 | turquoise | turquoise | turquoise | turquoise | |
| COTL1 | black | black | black | black | |
| PDE4B | black | black | black | black | |
| IL1RN | black | black | black | black | |
| OSM | black | black | black | black | |
| PDGFA | turquoise | turquoise | turquoise | turquoise | |
| CEP85L | black | gray | black | gray | |
| ID4 | turquoise | turquoise | turquoise | turquoise | |
| BAG2 | turquoise | turquoise | gray | turquoise | |
| TWSG1 | turquoise | gray | turquoise | turquoise | |
| CHL1 | turquoise | turquoise | turquoise | turquoise | |
| CD200 | turquoise | turquoise | gray | turquoise | |
| RIMKLB | turquoise | turquoise | turquoise | turquoise | |
| ALOX5 | black | black | black | black | |
| ZNF304 | turquoise | turquoise | turquoise | turquoise | |
| PODXL | turquoise | turquoise | gray | turquoise | |
| PFKFB3 | turquoise | gray | gray | gray | |
| P2RY14 | black | black | gray | gray | |
| DCBLD2 | turquoise | turquoise | turquoise | turquoise | |
| CSTA | black | black | gray | black | |
| ANTXR2 | turquoise | turquoise | gray | turquoise | |
| PLTP | turquoise | gray | turquoise | turquoise | |
| ZFP36L1 | turquoise | turquoise | turquoise | turquoise | |
| GNS | turquoise | gray | gray | turquoise | |
| TGFBR1 | turquoise | turquoise | turquoise | turquoise | |
| DUSP5 | black | gray | gray | gray | |
| DPYSL2 | turquoise | turquoise | turquoise | turquoise | |
| CORIN | turquoise | turquoise | gray | turquoise | |
| LSAMP | turquoise | turquoise | turquoise | turquoise | |
| MMRN1 | turquoise | turquoise | turquoise | turquoise | |
| RCAN1 | turquoise | turquoise | turquoise | turquoise | |
| ADH1B | turquoise | turquoise | turquoise | turquoise | |
| ABCA8 | turquoise | turquoise | turquoise | turquoise | |
| TMEM100 | turquoise | turquoise | turquoise | turquoise | |
| HSPB6 | turquoise | turquoise | turquoise | turquoise | |
| MYOCD | turquoise | gray | turquoise | turquoise | |
| DAPK1 | black | gray | black | gray | |
| RIT1 | black | gray | black | black | |
| AMIGO2 | turquoise | turquoise | gray | turquoise | |
| CPED1 | turquoise | gray | turquoise | turquoise | |
| ACTB | turquoise | gray | gray | turquoise | |
| CLIC6 | turquoise | turquoise | turquoise | turquoise | |
| MAOB | turquoise | turquoise | turquoise | turquoise | |
| FAT4 | turquoise | gray | turquoise | turquoise | |
| TDO2 | black | gray | gray | black | |
| FOXO1 | turquoise | turquoise | turquoise | turquoise | |
| TM4SF18 | turquoise | turquoise | turquoise | turquoise | |
| FMOD | turquoise | turquoise | turquoise | turquoise | |
| PDE5A | turquoise | turquoise | turquoise | turquoise | |
| ITIH5 | turquoise | gray | turquoise | turquoise | |
| LPP | turquoise | turquoise | gray | turquoise | |
| VIP | turquoise | turquoise | turquoise | turquoise | |
| TMEM158 | turquoise | turquoise | turquoise | turquoise | |
| RAB23 | turquoise | turquoise | turquoise | turquoise | |
| ARHGAP29 | turquoise | turquoise | turquoise | turquoise | |
| BLVRA | black | black | black | black | |
| ZBTB20 | turquoise | gray | gray | turquoise | |
| CCL11 | turquoise | gray | turquoise | turquoise | |
| PLAUR | black | black | black | black | |
| RAMP1 | turquoise | turquoise | gray | turquoise | |
| PCED1B | turquoise | gray | gray | turquoise | |
| CDKN2B | turquoise | turquoise | turquoise | turquoise | |
| NR2F2 | turquoise | gray | turquoise | turquoise | |

TABLE 5-continued

Genes for identification of subtypes and sub-subtypes

| | CCMS | ccs | CRCA1 | CRCA2 | potential 1 |
|---|---|---|---|---|---|
| NFIC | turquoise | gray | gray | turquoise | |
| FGF2 | turquoise | turquoise | turquoise | turquoise | |
| SSBP2 | turquoise | turquoise | turquoise | turquoise | |
| LPAR1 | turquoise | turquoise | turquoise | turquoise | |
| FSCN1 | turquoise | turquoise | gray | turquoise | |
| TNFAIP3 | black | black | black | black | |
| KCNJ15 | turquoise | gray | gray | gray | |
| CSGALNACT1 | turquoise | turquoise | turquoise | turquoise | |
| ADCY7 | black | black | black | gray | |
| PTX3 | turquoise | gray | turquoise | turquoise | |
| CX3CR1 | turquoise | turquoise | turquoise | turquoise | |
| SOBP | turquoise | turquoise | turquoise | turquoise | |
| PDZRN3 | turquoise | turquoise | turquoise | turquoise | |
| PKIG | turquoise | gray | turquoise | turquoise | |
| EMP1 | turquoise | turquoise | turquoise | turquoise | |
| LIFR | turquoise | turquoise | turquoise | turquoise | |
| LEF1 | turquoise | turquoise | turquoise | turquoise | |
| TLN1 | turquoise | gray | gray | turquoise | |
| SPON1 | turquoise | turquoise | turquoise | turquoise | |
| HPGDS | turquoise | turquoise | gray | turquoise | |
| GSN | turquoise | gray | turquoise | turquoise | |
| IL6 | turquoise | gray | turquoise | turquoise | |
| CITED2 | black | gray | black | gray | |
| PRDM1 | black | black | black | black | |
| TANC2 | turquoise | turquoise | gray | turquoise | |
| IL6ST | turquoise | turquoise | turquoise | turquoise | |
| ANXA1 | black | gray | black | gray | |
| G0S2 | black | black | gray | black | |
| GPRC5B | turquoise | turquoise | turquoise | turquoise | |
| ROR1 | turquoise | turquoise | gray | turquoise | |
| TRIM6 | turquoise | turquoise | turquoise | turquoise | |
| GLIPR1 | turquoise | turquoise | turquoise | turquoise | |
| CTSO | turquoise | turquoise | gray | turquoise | |
| RGCC | turquoise | turquoise | turquoise | turquoise | |
| STC1 | turquoise | turquoise | turquoise | turquoise | |
| HECTD2 | turquoise | turquoise | turquoise | turquoise | |
| RASA3 | turquoise | turquoise | turquoise | turquoise | |
| MCTP1 | turquoise | turquoise | gray | turquoise | |
| NRP2 | turquoise | turquoise | gray | turquoise | |
| CMAHP | turquoise | turquoise | turquoise | turquoise | |
| CPA3 | turquoise | turquoise | turquoise | turquoise | |
| MAP4K4 | turquoise | turquoise | turquoise | turquoise | |
| IRAK3 | black | gray | black | gray | |
| PLA1A | turquoise | gray | turquoise | turquoise | |
| FAM63B | turquoise | turquoise | gray | turquoise | |
| TRIB2 | black | black | black | black | |
| KLF9 | turquoise | turquoise | gray | turquoise | |
| PRNP | turquoise | turquoise | turquoise | turquoise | |
| ALDH1L2 | turquoise | turquoise | turquoise | turquoise | |
| CALB2 | turquoise | turquoise | turquoise | turquoise | |
| CCDC102B | turquoise | turquoise | turquoise | turquoise | |
| ELMO1 | turquoise | gray | gray | gray | |
| TPP1 | turquoise | gray | turquoise | turquoise | |
| TPSAB1 | turquoise | gray | turquoise | turquoise | |
| CD36 | black | gray | gray | gray | |
| RRAGD | turquoise | turquoise | gray | turquoise | |
| ADAM8 | black | black | black | black | |
| FZD2 | turquoise | turquoise | gray | turquoise | |
| PTGDS | turquoise | turquoise | turquoise | turquoise | |
| ABI3BP | turquoise | turquoise | turquoise | turquoise | |
| SLC43A3 | turquoise | gray | gray | gray | |
| GNB4 | black | gray | black | black | |
| IKBIP | black | black | black | gray | |
| CHI3L1 | turquoise | turquoise | turquoise | gray | |
| SOD2 | black | black | black | black | black |
| TYMP | black | black | black | black | black |
| BST2 | black | black | black | black | black |
| CCL19 | black | black | black | black | black |
| FCRL3 | black | black | black | black | black |
| CD80 | black | black | black | black | black |
| VNN2 | black | black | black | black | black |
| FMO1 | black | gray | gray | gray | black |
| LGMN | black | black | black | black | black |
| ZBED2 | black | black | black | black | black |
| PIK3AP1 | black | black | black | black | black |
| SLFN12 | black | gray | black | gray | black |

TABLE 5-continued

Genes for identification of subtypes and sub-subtypes

| | CCMS | ccs | CRCA1 | CRCA2 | potential 1 |
|---|---|---|---|---|---|
| LAX1 | black | black | black | black | black |
| GNLY | black | black | black | black | black |
| TNFAIP2 | black | black | black | black | black |
| SH2D1A | black | black | black | black | black |
| IL18RAP | black | black | black | black | black |
| IFI16 | black | black | black | black | black |
| EPB41L3 | black | black | black | gray | black |
| RAB8B | black | gray | black | black | black |
| RUNX3 | black | black | black | black | black |
| HS3ST3B1 | black | black | black | black | black |
| SP110 | black | black | black | black | black |
| IL7R | black | black | black | black | black |
| NCF4 | black | black | black | black | black |
| RGS1 | black | black | black | black | black |
| ITM2A | black | black | black | black | black |
| AQP9 | black | black | black | black | black |
| CLEC5A | black | black | gray | gray | black |
| TREM1 | black | black | black | gray | black |
| SCPEP1 | black | black | black | black | black |
| NPC2 | black | gray | black | black | black |
| LRRK2 | black | black | gray | black | black |
| ITGA4 | black | black | gray | black | black |
| KYNU | black | black | black | black | black |
| HLA-DOB | black | black | black | black | black |
| SDS | black | black | black | black | black |
| CSF3R | black | black | black | black | black |
| TIAM1 | black | black | black | gray | black |
| S100A8 | black | black | black | black | black |
| FCN1 | black | black | gray | black | black |
| RARRES3 | black | black | black | black | black |
| CCR7 | black | black | black | black | black |
| STAT2 | black | gray | black | black | black |
| NFATC1 | black | gray | black | gray | black |
| HMOX1 | black | black | black | black | black |
| IDO1 | black | black | black | black | black |
| THEMIS | black | black | black | black | black |
| PRF1 | black | black | black | black | black |
| NPL | black | black | black | black | black |
| TRAT1 | black | black | black | black | black |
| CPVL | black | black | gray | black | black |
| CCL13 | black | black | black | black | black |
| SAMHD1 | black | black | black | black | black |
| MMP9 | black | black | black | black | black |
| TRIM22 | black | black | black | black | black |
| BTN3A3 | black | black | black | black | black |
| PLCG2 | black | black | black | black | black |
| CST7 | black | black | black | black | black |
| SLC7A7 | black | black | black | black | black |
| STX11 | black | black | black | black | black |
| NAPSB | black | black | black | gray | black |
| ANKRD44 | black | black | black | black | black |
| FGL2 | black | black | black | black | black |
| RGS18 | black | black | black | black | black |
| CD40 | black | black | black | black | black |
| GPR84 | black | black | black | black | black |
| FAM65B | black | black | black | black | black |
| CXCL10 | black | black | black | black | black |
| GBP2 | black | black | black | black | black |
| ITGB2-AS1 | black | black | black | black | black |
| HSD11B1 | black | black | black | gray | black |
| ADORA3 | black | black | black | black | black |
| CYTIP | black | black | black | black | black |
| ENPP2 | black | black | black | black | black |
| ATP8B4 | black | black | black | black | black |
| GZMA | black | black | black | black | black |
| EOMES | black | black | black | black | black |
| GBP4 | black | black | black | black | black |
| CD69 | black | black | black | black | black |
| CXCR4 | black | black | black | black | black |
| GPR34 | black | gray | black | black | black |
| ARHGDIB | black | black | black | black | black |
| GBP1 | black | black | black | black | black |
| CD38 | black | black | black | black | black |
| BCL2A1 | black | black | black | black | black |
| JAK3 | black | black | black | black | black |
| CORO1A | black | black | black | black | black |

TABLE 5-continued

Genes for identification of subtypes and sub-subtypes

| | CCMS | ccs | CRCA1 | CRCA2 | potential 1 |
|---|---|---|---|---|---|
| CD274 | black | black | black | black | black |
| RASGRP1 | black | black | black | black | black |
| GATA3 | black | black | black | black | black |
| APOL3 | black | black | black | black | black |
| PLEK | black | black | black | black | black |
| EMR2 | black | black | black | black | black |
| CD27 | black | black | black | black | black |
| RASSF4 | black | black | black | black | black |
| PPP1R16B | black | black | black | black | black |
| SIGLEC1 | black | black | black | black | black |
| GNG2 | black | black | black | gray | black |
| GPR183 | black | black | black | black | black |
| CYSLTR1 | black | black | black | black | black |
| GLIPR2 | black | black | black | gray | black |
| DOCK8 | black | black | black | black | black |
| RNASE6 | black | black | black | black | black |
| APOE | black | black | black | black | black |
| ITGAX | black | black | black | black | black |
| RAC2 | black | black | black | black | black |
| GM2A | black | gray | black | black | black |
| TREM2 | black | black | black | gray | black |
| CXCL13 | black | black | black | black | black |
| CCL8 | black | black | black | black | black |
| CXCL9 | black | black | black | black | black |
| GGTA1P | black | black | black | black | black |
| NLRC3 | black | black | black | black | black |
| FPR1 | black | black | black | black | black |
| APOC1 | black | black | black | black | black |
| GPR171 | black | black | black | black | black |
| GIMAP7 | black | black | black | black | black |
| RHOH | black | black | black | black | black |
| ICAM1 | black | black | black | black | black |
| VAMP5 | black | black | black | black | black |
| KLRD1 | black | black | black | black | black |
| TMEM140 | black | black | black | black | black |
| TLR2 | black | black | black | black | black |
| CLEC4E | black | black | black | black | black |
| SLC1A3 | black | black | black | black | black |
| CLIC2 | black | black | black | black | black |
| CCR2 | black | black | black | black | black |
| ITGAL | black | black | black | black | black |
| GZMH | black | black | black | black | black |
| IL4I1 | black | black | black | black | black |
| SUCNR1 | black | black | black | black | black |
| SELL | black | black | black | black | black |
| IL2RA | black | black | black | black | black |
| CCL18 | black | black | black | black | black |
| ITK | black | black | black | black | black |
| NKG7 | black | black | black | black | black |
| CECR1 | black | black | black | black | black |
| CD8A | black | black | black | black | black |
| ST8SIA4 | black | black | black | black | black |
| CCL4 | black | black | black | black | black |
| APOBEC3G | black | black | black | black | black |
| EVL | black | black | black | black | black |
| IL18BP | black | black | black | black | black |
| PIK3CG | black | black | black | black | black |
| FCGR3B | black | black | black | black | black |
| C5AR1 | black | black | black | black | black |
| FCGR2C | black | black | black | black | black |
| ALOX5AP | black | black | black | black | black |
| ARL4C | black | gray | gray | gray | black |
| VCAM1 | black | black | gray | gray | black |
| MSR1 | black | black | black | black | black |
| TM6SF1 | black | black | black | black | black |
| DSE | black | gray | gray | black | black |
| NR3C1 | black | black | gray | gray | black |
| MRC1 | black | black | black | black | black |
| NRP1 | black | gray | black | gray | black |
| ZEB2 | black | gray | gray | gray | black |
| FGR | black | black | black | black | black |
| KMO | black | black | black | black | black |
| DOK3 | black | black | black | black | black |
| DPYD | black | black | black | black | black |
| CLEC4A | black | black | black | black | black |
| CLEC2B | black | black | black | black | black |

TABLE 5-continued

Genes for identification of subtypes and sub-subtypes

| | CCMS | ccs | CRCA1 | CRCA2 | potential 1 |
|---|---|---|---|---|---|
| SLAMF7 | black | black | black | black | black |
| HLA-DMA | black | black | black | black | black |
| SLC15A3 | black | black | black | black | black |
| PIK3CD | black | black | black | black | black |
| KLHL6 | black | black | black | black | black |
| SAMSN1 | black | black | black | black | black |
| TRAF3IP3 | black | black | black | black | black |
| CCL5 | black | black | black | black | black |
| ARHGAP15 | black | black | black | black | black |
| CD72 | black | black | black | black | black |
| IL2RB | black | black | black | black | black |
| MS4A7 | black | black | black | black | black |
| 1-Mar | black | black | black | black | black |
| GBP5 | black | black | black | black | black |
| CD74 | black | black | black | black | black |
| FAM49A | black | black | black | black | black |
| PRKCB | black | black | black | black | black |
| FYB | black | black | black | black | black |
| GZMK | black | black | black | black | black |
| FAM26F | black | black | black | black | black |
| SLC31A2 | black | black | black | black | black |
| P2RY13 | black | black | black | black | black |
| GIMAP8 | black | black | black | black | black |
| HLA-DOA | black | black | black | black | black |
| TLR1 | black | black | black | black | black |
| PTPRC | black | black | black | black | black |
| LY86 | black | black | black | black | black |
| LILRB2 | black | black | black | black | black |
| DOCK10 | black | black | black | black | black |
| SRGN | black | black | black | black | black |
| CD2 | black | black | black | black | black |
| RASSF5 | black | black | black | black | black |
| HLA-DQB1 | black | black | black | black | black |
| GIMAP1 | black | black | black | black | black |
| THEMIS2 | black | black | black | black | black |
| ACP5 | black | black | black | black | black |
| TFEC | black | black | black | black | black |
| FCGR2B | black | black | black | black | black |
| MPEG1 | black | black | black | black | black |
| GPR65 | black | black | black | black | black |
| HLA-DPA1 | black | black | black | black | black |
| TNFSF13B | black | black | black | black | black |
| LILRB4 | black | black | black | black | black |
| VSIG4 | black | black | black | black | black |
| FCGR2A | black | black | black | black | black |
| NCF2 | black | black | black | black | black |
| ITGAM | black | black | black | black | black |
| CHST11 | black | black | black | black | black |
| PILRA | black | black | black | black | black |
| PLXNC1 | black | black | black | black | black |
| GIMAP6 | black | black | black | black | black |
| RASSF2 | black | black | black | black | black |
| CD52 | black | black | black | black | black |
| TRAC | black | black | black | black | black |
| EVI2A | black | black | black | black | black |
| MYO1F | black | black | black | black | black |
| FLI1 | black | black | black | black | black |
| RCSD1 | black | black | black | black | black |
| C10orf128 | black | black | black | black | black |
| CCR5 | black | black | black | black | black |
| CYBB | black | black | black | black | black |
| SIGLEC10 | black | black | black | black | black |
| CSF2RB | black | black | black | black | black |
| ARHGEF6 | black | black | black | black | black |
| WIPF1 | black | black | black | black | black |
| CD37 | black | black | black | black | black |
| PLA2G7 | black | black | black | black | black |
| EVI2B | black | black | black | black | black |
| ARHGAP9 | black | black | black | black | black |
| HAVCR2 | black | black | black | black | black |
| IGSF6 | black | black | black | black | black |
| HLA-DRA | black | black | black | black | black |
| GMFG | black | black | black | black | black |
| IL10RA | black | black | black | black | black |
| SASH3 | black | black | black | black | black |
| LCP1 | black | black | black | black | black |

TABLE 5-continued

Genes for identification of subtypes and sub-subtypes

|  | CCMS | ccs | CRCA1 | CRCA2 | potential 1 |
|---|---|---|---|---|---|
| GIMAP4 | black | black | black | black | black |
| LY96 | black | black | black | black | black |
| MS4A6A | black | black | black | black | black |
| CD14 | black | black | black | black | black |
| CCR1 | black | black | black | black | black |
| LST1 | black | black | black | black | black |
| CD330LF | black | black | black | black | black |
| CD163 | black | black | black | black | black |
| GPNMB | black | black | black | black | black |
| TLR8 | black | black | black | black | black |
| HLA-DMB | black | black | black | black | black |
| MS4A4A | black | black | black | black | black |
| CD84 | black | black | black | black | black |
| NCKAP1L | black | black | black | black | black |
| APBB1IP | black | black | black | black | black |
| DOCK2 | black | black | black | black | black |
| ARHGAP30 | black | black | black | black | black |
| SLA | black | black | black | black | black |
| CD48 | black | black | black | black | black |
| HCLS1 | black | black | black | black | black |
| C1orf162 | black | black | black | black | black |
| C1QC | black | black | black | black | black |
| CSF1R | black | black | black | black | black |
| CD300A | black | black | black | black | black |
| MAFB | black | black | black | black | black |
| FPR3 | black | black | black | black | black |
| CLEC7A | black | black | black | black | black |
| CD86 | black | black | black | black | black |
| HCK | black | black | black | black | black |
| C3AR1 | black | black | black | black | black |
| SLAMF8 | black | black | black | black | black |
| LAIR1 | black | black | black | black | black |
| FCER1G | black | black | black | black | black |
| TYROBP | black | black | black | black | black |
| CD53 | black | black | black | black | black |
| C1QB | black | black | black | black | black |
| LAPTM5 | black | black | black | black | black |
| C1QA | black | black | black | black | black |
| ITGB2 | black | black | black | black | black |
| LCP2 | black | black | black | black | black |
| MNDA | black | black | black | black | black |
| LRP1 | turquoise | turquoise | gray | turquoise | turquoise |
| FOXF1 | turquoise | gray | turquoise | turquoise | turquoise |
| ECM1 | turquoise | turquoise | turquoise | turquoise | turquoise |
| DNAJB4 | turquoise | turquoise | turquoise | turquoise | turquoise |
| HSPB1 | turquoise | turquoise | turquoise | turquoise | turquoise |
| SELE | turquoise | turquoise | turquoise | turquoise | turquoise |
| ANGPT1 | turquoise | turquoise | turquoise | turquoise | turquoise |
| SULF2 | turquoise | turquoise | turquoise | turquoise | turquoise |
| COL7A1 | turquoise | gray | turquoise | turquoise | turquoise |
| OBSL1 | turquoise | turquoise | turquoise | turquoise | turquoise |
| SOCS3 | turquoise | gray | gray | turquoise | turquoise |
| CDKN1C | turquoise | turquoise | turquoise | turquoise | turquoise |
| FRY | turquoise | turquoise | turquoise | turquoise | turquoise |
| MAP9 | turquoise | turquoise | turquoise | turquoise | turquoise |
| CD99 | turquoise | turquoise | turquoise | turquoise | turquoise |
| FAM126A | turquoise | turquoise | turquoise | turquoise | turquoise |
| PPAP2B | turquoise | turquoise | turquoise | turquoise | turquoise |
| PAM | turquoise | turquoise | turquoise | turquoise | turquoise |
| NR4A3 | turquoise | turquoise | turquoise | turquoise | turquoise |
| NEGR1 | turquoise | turquoise | turquoise | turquoise | turquoise |
| TCF21 | turquoise | gray | turquoise | turquoise | turquoise |
| PI15 | turquoise | turquoise | turquoise | turquoise | turquoise |
| FAM20A | turquoise | gray | turquoise | turquoise | turquoise |
| PENK | turquoise | turquoise | turquoise | turquoise | turquoise |
| ITGB1 | turquoise | gray | turquoise | turquoise | turquoise |
| SSH1 | turquoise | gray | gray | turquoise | turquoise |
| CCDC69 | turquoise | gray | turquoise | turquoise | turquoise |
| ZSCAN18 | turquoise | turquoise | turquoise | turquoise | turquoise |
| KCTD12 | turquoise | turquoise | gray | turquoise | turquoise |
| PTGS1 | turquoise | turquoise | turquoise | turquoise | turquoise |
| MCC | turquoise | turquoise | turquoise | turquoise | turquoise |
| SEC14L1 | turquoise | gray | gray | gray | turquoise |
| SDPR | turquoise | turquoise | turquoise | turquoise | turquoise |
| SVIL | turquoise | gray | turquoise | turquoise | turquoise |
| SLC8A1 | turquoise | gray | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| ARHGAP24 | turquoise | turquoise | turquoise | turquoise | turquoise |
| PGM5 | turquoise | turquoise | turquoise | turquoise | turquoise |
| RORA | turquoise | turquoise | turquoise | turquoise | turquoise |
| WFDC1 | turquoise | gray | turquoise | turquoise | turquoise |
| ZNF423 | turquoise | turquoise | gray | turquoise | turquoise |
| HIP1 | turquoise | turquoise | turquoise | turquoise | turquoise |
| TBC1D9 | turquoise | turquoise | turquoise | turquoise | turquoise |
| ATXN1 | turquoise | turquoise | turquoise | turquoise | turquoise |
| GULP1 | turquoise | turquoise | turquoise | turquoise | turquoise |
| IGF1 | turquoise | turquoise | turquoise | turquoise | turquoise |
| CADM1 | turquoise | turquoise | turquoise | turquoise | turquoise |
| TFPI | turquoise | turquoise | turquoise | turquoise | turquoise |
| FAM198B | turquoise | turquoise | turquoise | turquoise | turquoise |
| PPAP2A | turquoise | turquoise | turquoise | turquoise | turquoise |
| FZD8 | turquoise | turquoise | turquoise | turquoise | turquoise |
| PLA2G5 | turquoise | turquoise | turquoise | turquoise | turquoise |
| PTN | turquoise | turquoise | turquoise | turquoise | turquoise |
| PRKG1 | turquoise | turquoise | gray | turquoise | turquoise |
| RTN1 | turquoise | turquoise | gray | turquoise | turquoise |
| ABCA1 | turquoise | turquoise | turquoise | turquoise | turquoise |
| SFRP1 | turquoise | turquoise | turquoise | turquoise | turquoise |
| FILIP1 | turquoise | turquoise | turquoise | turquoise | turquoise |
| S100A4 | turquoise | gray | turquoise | turquoise | turquoise |
| STEAP4 | turquoise | turquoise | turquoise | turquoise | turquoise |
| RBP7 | turquoise | turquoise | turquoise | turquoise | turquoise |
| UNC5B | turquoise | turquoise | turquoise | turquoise | turquoise |
| RBPMS | turquoise | turquoise | gray | turquoise | turquoise |
| KCNMA1 | turquoise | turquoise | turquoise | turquoise | turquoise |
| DUSP1 | turquoise | gray | turquoise | turquoise | turquoise |
| BCHE | turquoise | turquoise | turquoise | turquoise | turquoise |
| PCSK5 | turquoise | turquoise | turquoise | turquoise | turquoise |
| LINC00341 | turquoise | turquoise | gray | turquoise | turquoise |
| ADAMTS6 | turquoise | turquoise | turquoise | turquoise | turquoise |
| PDGFRA | turquoise | turquoise | turquoise | turquoise | turquoise |
| CLU | turquoise | turquoise | turquoise | turquoise | turquoise |
| FLT1 | turquoise | gray | turquoise | turquoise | turquoise |
| DKK2 | turquoise | turquoise | turquoise | turquoise | turquoise |
| ATP8B2 | turquoise | turquoise | turquoise | gray | turquoise |
| DOCK4 | turquoise | turquoise | gray | turquoise | turquoise |
| HOXB2 | turquoise | turquoise | gray | turquoise | turquoise |
| GPRASP1 | turquoise | turquoise | gray | turquoise | turquoise |
| GPM6B | turquoise | turquoise | turquoise | turquoise | turquoise |
| DEGS1 | turquoise | turquoise | turquoise | turquoise | turquoise |
| C7 | turquoise | turquoise | gray | turquoise | turquoise |
| FBXO32 | turquoise | turquoise | turquoise | turquoise | turquoise |
| MEIS2 | turquoise | turquoise | gray | turquoise | turquoise |
| DBN1 | turquoise | turquoise | turquoise | turquoise | turquoise |
| PAPLN | turquoise | turquoise | turquoise | turquoise | turquoise |
| IGDCC4 | turquoise | turquoise | turquoise | turquoise | turquoise |
| NOTCH2 | turquoise | gray | turquoise | turquoise | turquoise |
| SMARCA1 | turquoise | turquoise | turquoise | turquoise | turquoise |
| SELP | turquoise | turquoise | turquoise | turquoise | turquoise |
| ADAM19 | turquoise | turquoise | turquoise | turquoise | turquoise |
| CDO1 | turquoise | turquoise | turquoise | turquoise | turquoise |
| RCAN2 | turquoise | gray | turquoise | turquoise | turquoise |
| RHOJ | turquoise | turquoise | turquoise | turquoise | turquoise |
| MARCO | turquoise | gray | gray | gray | turquoise |
| RNF144A | turquoise | turquoise | gray | turquoise | turquoise |
| RUNX2 | turquoise | turquoise | turquoise | turquoise | turquoise |
| BCL6 | turquoise | gray | gray | turquoise | turquoise |
| PAPPA | turquoise | turquoise | turquoise | turquoise | turquoise |
| GPR161 | turquoise | turquoise | turquoise | turquoise | turquoise |
| KLF2 | turquoise | turquoise | turquoise | turquoise | turquoise |
| CAV2 | turquoise | turquoise | turquoise | turquoise | turquoise |
| HEY1 | turquoise | turquoise | turquoise | turquoise | turquoise |
| FYN | turquoise | turquoise | gray | turquoise | turquoise |
| FAM13C | turquoise | turquoise | turquoise | turquoise | turquoise |
| TMTC1 | turquoise | turquoise | turquoise | turquoise | turquoise |
| PPP1R12B | turquoise | turquoise | turquoise | turquoise | turquoise |
| PGM5-AS1 | turquoise | gray | turquoise | turquoise | turquoise |
| OGN | turquoise | turquoise | turquoise | turquoise | turquoise |
| C2orf40 | turquoise | turquoise | turquoise | turquoise | turquoise |
| ANGPTL1 | turquoise | turquoise | turquoise | turquoise | turquoise |
| MAMDC2 | turquoise | turquoise | turquoise | turquoise | turquoise |
| TCEAL2 | turquoise | turquoise | turquoise | turquoise | turquoise |
| ATP1A2 | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| CHRDL1 | turquoise | turquoise | turquoise | turquoise | turquoise |
| PDZRN4 | turquoise | turquoise | turquoise | turquoise | turquoise |
| SCN7A | turquoise | turquoise | turquoise | turquoise | turquoise |
| FHL1 | turquoise | turquoise | turquoise | turquoise | turquoise |
| ANK2 | turquoise | turquoise | turquoise | turquoise | turquoise |
| LMO3 | turquoise | turquoise | turquoise | turquoise | turquoise |
| C5orf46 | turquoise | turquoise | turquoise | turquoise | turquoise |
| FAM171B | turquoise | turquoise | turquoise | turquoise | turquoise |
| SCUBE2 | turquoise | turquoise | turquoise | turquoise | turquoise |
| GPR133 | turquoise | turquoise | turquoise | turquoise | turquoise |
| RDX | turquoise | turquoise | turquoise | turquoise | turquoise |
| CD109 | turquoise | turquoise | turquoise | turquoise | turquoise |
| ROBO1 | turquoise | turquoise | turquoise | turquoise | turquoise |
| ADARB1 | turquoise | turquoise | gray | turquoise | turquoise |
| AGTR1 | turquoise | turquoise | turquoise | turquoise | turquoise |
| SETBP1 | turquoise | turquoise | turquoise | turquoise | turquoise |
| LYVE1 | turquoise | turquoise | turquoise | turquoise | turquoise |
| GPX8 | turquoise | turquoise | turquoise | turquoise | turquoise |
| CBX6 | turquoise | turquoise | gray | turquoise | turquoise |
| COL16A1 | turquoise | turquoise | turquoise | turquoise | turquoise |
| MAN1C1 | turquoise | turquoise | turquoise | turquoise | turquoise |
| GXYLT2 | turquoise | turquoise | turquoise | turquoise | turquoise |
| SHISA2 | turquoise | turquoise | turquoise | turquoise | turquoise |
| GPX3 | turquoise | turquoise | turquoise | turquoise | turquoise |
| LAMA2 | turquoise | turquoise | turquoise | turquoise | turquoise |
| ZNF331 | turquoise | turquoise | turquoise | turquoise | turquoise |
| OLR1 | turquoise | gray | turquoise | turquoise | turquoise |
| LTBP3 | turquoise | turquoise | turquoise | turquoise | turquoise |
| GPC1 | turquoise | turquoise | turquoise | turquoise | turquoise |
| AHNAK2 | turquoise | turquoise | turquoise | turquoise | turquoise |
| SPP1 | turquoise | turquoise | turquoise | turquoise | turquoise |
| CNTN4 | turquoise | turquoise | turquoise | turquoise | turquoise |
| BEX4 | turquoise | turquoise | turquoise | turquoise | turquoise |
| 6-Sep | turquoise | gray | gray | turquoise | turquoise |
| RGL1 | turquoise | turquoise | turquoise | turquoise | turquoise |
| MEG3 | turquoise | turquoise | turquoise | turquoise | turquoise |
| FABP4 | turquoise | turquoise | turquoise | turquoise | turquoise |
| EDIL3 | turquoise | turquoise | turquoise | turquoise | turquoise |
| APOD | turquoise | turquoise | turquoise | turquoise | turquoise |
| SLC2A3 | turquoise | gray | turquoise | turquoise | turquoise |
| EMCN | turquoise | turquoise | turquoise | turquoise | turquoise |
| PRR16 | turquoise | turquoise | turquoise | turquoise | turquoise |
| SHANK3 | turquoise | turquoise | gray | turquoise | turquoise |
| PLA2G4C | turquoise | turquoise | turquoise | turquoise | turquoise |
| CSGALNACT2 | turquoise | turquoise | turquoise | turquoise | turquoise |
| FGF7 | turquoise | turquoise | turquoise | turquoise | turquoise |
| TSC22D3 | turquoise | gray | turquoise | turquoise | turquoise |
| SIRPA | turquoise | gray | turquoise | turquoise | turquoise |
| CHRDL2 | turquoise | turquoise | turquoise | turquoise | turquoise |
| TSPAN2 | turquoise | turquoise | turquoise | turquoise | turquoise |
| OMD | turquoise | turquoise | turquoise | turquoise | turquoise |
| LINC00312 | turquoise | turquoise | turquoise | turquoise | turquoise |
| LRRC17 | turquoise | turquoise | turquoise | turquoise | turquoise |
| NAV3 | turquoise | turquoise | turquoise | turquoise | turquoise |
| PTGER3 | turquoise | turquoise | turquoise | turquoise | turquoise |
| ROR2 | turquoise | turquoise | turquoise | turquoise | turquoise |
| SPHK1 | turquoise | gray | turquoise | turquoise | turquoise |
| ANKRD6 | turquoise | turquoise | turquoise | turquoise | turquoise |
| SLFN11 | turquoise | gray | gray | turquoise | turquoise |
| STAB1 | turquoise | turquoise | gray | turquoise | turquoise |
| ALPK2 | turquoise | turquoise | turquoise | turquoise | turquoise |
| PLAT | turquoise | gray | turquoise | turquoise | turquoise |
| SOX7 | turquoise | turquoise | turquoise | turquoise | turquoise |
| PPP1R14A | turquoise | turquoise | turquoise | turquoise | turquoise |
| PLAU | turquoise | turquoise | turquoise | turquoise | turquoise |
| CSRP2 | turquoise | turquoise | turquoise | turquoise | turquoise |
| GRP | turquoise | turquoise | turquoise | turquoise | turquoise |
| BHLHE22 | turquoise | turquoise | turquoise | turquoise | turquoise |
| EPHA3 | turquoise | turquoise | turquoise | turquoise | turquoise |
| DIO2 | turquoise | turquoise | turquoise | turquoise | turquoise |
| SCG2 | turquoise | turquoise | turquoise | turquoise | turquoise |
| RGS16 | turquoise | turquoise | gray | turquoise | turquoise |
| ELN | turquoise | turquoise | turquoise | turquoise | turquoise |
| ELK3 | turquoise | turquoise | turquoise | turquoise | turquoise |
| CAP2 | turquoise | turquoise | gray | turquoise | turquoise |
| GPX7 | turquoise | turquoise | turquoise | turquoise | turquoise |

TABLE 5-continued

| | Genes for identification of subtypes and sub-subtypes | | | | |
|---|---|---|---|---|---|
| | CCMS | ccs | CRCA1 | CRCA2 | potential 1 |
| PDGFRL | turquoise | turquoise | turquoise | turquoise | turquoise |
| UCHL1 | turquoise | turquoise | turquoise | turquoise | turquoise |
| EPYC | turquoise | turquoise | turquoise | turquoise | turquoise |
| ITGB5 | turquoise | turquoise | turquoise | turquoise | turquoise |
| GADD45B | turquoise | gray | turquoise | turquoise | turquoise |
| GLRB | turquoise | turquoise | turquoise | turquoise | turquoise |
| RGS2 | turquoise | turquoise | turquoise | turquoise | turquoise |
| DIP2C | turquoise | turquoise | turquoise | turquoise | turquoise |
| TTC7B | turquoise | turquoise | turquoise | turquoise | turquoise |
| CCDC88A | turquoise | gray | turquoise | turquoise | turquoise |
| SAMD4A | turquoise | turquoise | turquoise | turquoise | turquoise |
| F13A1 | turquoise | turquoise | turquoise | turquoise | turquoise |
| MEOX2 | turquoise | turquoise | turquoise | turquoise | turquoise |
| PRELP | turquoise | turquoise | turquoise | turquoise | turquoise |
| CCL21 | turquoise | turquoise | turquoise | turquoise | turquoise |
| FST | turquoise | turquoise | turquoise | turquoise | turquoise |
| CALCRL | turquoise | turquoise | turquoise | turquoise | turquoise |
| LRRN4CL | turquoise | turquoise | turquoise | turquoise | turquoise |
| ETS1 | turquoise | gray | turquoise | turquoise | turquoise |
| ITPRIP | turquoise | gray | turquoise | turquoise | turquoise |
| SRPX | turquoise | turquoise | turquoise | turquoise | turquoise |
| CHRNA3 | turquoise | turquoise | turquoise | turquoise | turquoise |
| PXDC1 | turquoise | turquoise | turquoise | turquoise | turquoise |
| WNT2 | turquoise | turquoise | turquoise | turquoise | turquoise |
| SERPINE1 | turquoise | turquoise | turquoise | turquoise | turquoise |
| PCDH17 | turquoise | turquoise | turquoise | turquoise | turquoise |
| FAM127A | turquoise | turquoise | turquoise | turquoise | turquoise |
| DACT1 | turquoise | turquoise | turquoise | turquoise | turquoise |
| TMEM45A | turquoise | turquoise | turquoise | turquoise | turquoise |
| NPR3 | turquoise | turquoise | turquoise | turquoise | turquoise |
| SDK1 | turquoise | turquoise | turquoise | turquoise | turquoise |
| CYGB | turquoise | turquoise | turquoise | turquoise | turquoise |
| OLFML2A | turquoise | gray | turquoise | turquoise | turquoise |
| ARL10 | turquoise | turquoise | turquoise | turquoise | turquoise |
| HTR2B | turquoise | turquoise | turquoise | turquoise | turquoise |
| TCEAL3 | turquoise | turquoise | turquoise | turquoise | turquoise |
| MDFIC | turquoise | turquoise | turquoise | turquoise | turquoise |
| PALMD | turquoise | turquoise | turquoise | turquoise | turquoise |
| CILP | turquoise | turquoise | turquoise | turquoise | turquoise |
| AQP1 | turquoise | turquoise | turquoise | turquoise | turquoise |
| CXCL12 | turquoise | turquoise | turquoise | turquoise | turquoise |
| RERG | turquoise | turquoise | turquoise | turquoise | turquoise |
| TCEA2 | turquoise | turquoise | turquoise | turquoise | turquoise |
| PBX3 | turquoise | turquoise | turquoise | turquoise | turquoise |
| GLI3 | turquoise | turquoise | turquoise | turquoise | turquoise |
| DSEL | turquoise | turquoise | turquoise | turquoise | turquoise |
| ADAMTS1 | turquoise | turquoise | turquoise | turquoise | turquoise |
| PTPLAD2 | turquoise | turquoise | turquoise | turquoise | turquoise |
| ALDH1A3 | turquoise | turquoise | turquoise | turquoise | turquoise |
| VWF | turquoise | turquoise | turquoise | turquoise | turquoise |
| ATP2B4 | turquoise | turquoise | turquoise | turquoise | turquoise |
| CFL2 | turquoise | turquoise | turquoise | turquoise | turquoise |
| ZNF677 | turquoise | turquoise | turquoise | turquoise | turquoise |
| RGS4 | turquoise | turquoise | turquoise | turquoise | turquoise |
| GALNT15 | turquoise | turquoise | turquoise | turquoise | turquoise |
| SYNE1 | turquoise | turquoise | gray | turquoise | turquoise |
| CYP1B1 | turquoise | turquoise | turquoise | turquoise | turquoise |
| TUSC3 | turquoise | turquoise | turquoise | turquoise | turquoise |
| ZNF532 | turquoise | turquoise | turquoise | turquoise | turquoise |
| RSPO3 | turquoise | turquoise | turquoise | turquoise | turquoise |
| NAV1 | turquoise | turquoise | turquoise | turquoise | turquoise |
| QKI | turquoise | gray | turquoise | turquoise | turquoise |
| THBS4 | turquoise | turquoise | turquoise | turquoise | turquoise |
| CALU | turquoise | gray | turquoise | turquoise | turquoise |
| STOM | turquoise | turquoise | turquoise | turquoise | turquoise |
| TIMP1 | turquoise | turquoise | turquoise | turquoise | turquoise |
| RASSF8 | turquoise | turquoise | turquoise | turquoise | turquoise |
| RGMA | turquoise | turquoise | turquoise | turquoise | turquoise |
| CPXM2 | turquoise | turquoise | turquoise | turquoise | turquoise |
| BTBD19 | turquoise | turquoise | turquoise | turquoise | turquoise |
| ZCCHC24 | turquoise | turquoise | gray | turquoise | turquoise |
| DENND5A | turquoise | turquoise | turquoise | turquoise | turquoise |
| ELTD1 | turquoise | turquoise | turquoise | turquoise | turquoise |
| LPHN2 | turquoise | turquoise | turquoise | turquoise | turquoise |
| TRPC1 | turquoise | turquoise | turquoise | turquoise | turquoise |
| TPST1 | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| TGFB1 | turquoise | gray | gray | turquoise | turquoise |
| ISM1 | turquoise | turquoise | turquoise | turquoise | turquoise |
| INMT | turquoise | turquoise | turquoise | turquoise | turquoise |
| MMP11 | turquoise | turquoise | turquoise | turquoise | turquoise |
| LTBP1 | turquoise | turquoise | turquoise | turquoise | turquoise |
| THBS1 | turquoise | turquoise | turquoise | turquoise | turquoise |
| HSD17B6 | turquoise | turquoise | turquoise | turquoise | turquoise |
| NREP | turquoise | turquoise | turquoise | turquoise | turquoise |
| SSPN | turquoise | turquoise | turquoise | turquoise | turquoise |
| C10orf10 | turquoise | turquoise | turquoise | turquoise | turquoise |
| TRPS1 | turquoise | turquoise | turquoise | turquoise | turquoise |
| KLHL5 | turquoise | turquoise | turquoise | turquoise | turquoise |
| ADAMTS5 | turquoise | turquoise | turquoise | turquoise | turquoise |
| SLC24A3 | turquoise | turquoise | turquoise | turquoise | turquoise |
| LMCD1 | turquoise | turquoise | turquoise | turquoise | turquoise |
| ANXA6 | turquoise | turquoise | turquoise | turquoise | turquoise |
| UBE2E2 | turquoise | turquoise | turquoise | turquoise | turquoise |
| C3 | turquoise | turquoise | turquoise | turquoise | turquoise |
| MYO5A | turquoise | gray | turquoise | turquoise | turquoise |
| HSPG2 | turquoise | turquoise | turquoise | turquoise | turquoise |
| CAV1 | turquoise | turquoise | turquoise | turquoise | turquoise |
| PNMAL1 | turquoise | turquoise | turquoise | turquoise | turquoise |
| CLIC4 | turquoise | turquoise | turquoise | turquoise | turquoise |
| DCHS1 | turquoise | turquoise | turquoise | turquoise | turquoise |
| KCNJ8 | turquoise | turquoise | turquoise | turquoise | turquoise |
| EML1 | turquoise | turquoise | turquoise | turquoise | turquoise |
| TP73-AS1 | turquoise | turquoise | gray | turquoise | turquoise |
| SMARCD3 | turquoise | turquoise | turquoise | turquoise | turquoise |
| MEDAG | turquoise | turquoise | turquoise | turquoise | turquoise |
| CCL2 | turquoise | gray | turquoise | turquoise | turquoise |
| CLIP4 | turquoise | turquoise | turquoise | turquoise | turquoise |
| DCLK1 | turquoise | turquoise | turquoise | turquoise | turquoise |
| ARMCX2 | turquoise | turquoise | turquoise | turquoise | turquoise |
| CHST15 | turquoise | gray | turquoise | turquoise | turquoise |
| CALHM2 | turquoise | turquoise | turquoise | turquoise | turquoise |
| C1QTNF3 | turquoise | turquoise | turquoise | turquoise | turquoise |
| JAZF1 | turquoise | turquoise | turquoise | turquoise | turquoise |
| KIF26B | turquoise | turquoise | turquoise | turquoise | turquoise |
| GNG11 | turquoise | turquoise | turquoise | turquoise | turquoise |
| ERG | turquoise | turquoise | turquoise | turquoise | turquoise |
| GJA1 | turquoise | turquoise | turquoise | turquoise | turquoise |
| RBMS1 | turquoise | turquoise | turquoise | turquoise | turquoise |
| CPXM1 | turquoise | turquoise | turquoise | turquoise | turquoise |
| MFAP4 | turquoise | turquoise | turquoise | turquoise | turquoise |
| ITGBL1 | turquoise | turquoise | turquoise | turquoise | turquoise |
| MMRN2 | turquoise | turquoise | turquoise | turquoise | turquoise |
| FZD1 | turquoise | turquoise | turquoise | turquoise | turquoise |
| LATS2 | turquoise | turquoise | turquoise | turquoise | turquoise |
| CDH5 | turquoise | turquoise | turquoise | turquoise | turquoise |
| SGCE | turquoise | turquoise | turquoise | turquoise | turquoise |
| NID1 | turquoise | turquoise | turquoise | turquoise | turquoise |
| RBMS3 | turquoise | turquoise | turquoise | turquoise | turquoise |
| PLXDC2 | turquoise | turquoise | turquoise | turquoise | turquoise |
| CYBRD1 | turquoise | turquoise | turquoise | turquoise | turquoise |
| IGFBP3 | turquoise | turquoise | turquoise | turquoise | turquoise |
| EDNRA | turquoise | turquoise | turquoise | turquoise | turquoise |
| MN1 | turquoise | turquoise | turquoise | turquoise | turquoise |
| HS3ST3A1 | turquoise | turquoise | turquoise | turquoise | turquoise |
| EBF1 | turquoise | turquoise | turquoise | turquoise | turquoise |
| SERPINH1 | turquoise | gray | turquoise | turquoise | turquoise |
| GEM | turquoise | turquoise | turquoise | turquoise | turquoise |
| TNFAIP6 | turquoise | gray | turquoise | turquoise | turquoise |
| KAL1 | turquoise | turquoise | turquoise | turquoise | turquoise |
| RAI14 | turquoise | turquoise | turquoise | turquoise | turquoise |
| HEYL | turquoise | turquoise | turquoise | turquoise | turquoise |
| CFH | turquoise | turquoise | turquoise | turquoise | turquoise |
| PALLD | turquoise | turquoise | turquoise | turquoise | turquoise |
| TNFSF4 | turquoise | turquoise | turquoise | turquoise | turquoise |
| MXRA7 | turquoise | turquoise | turquoise | turquoise | turquoise |
| PDLIM4 | turquoise | turquoise | turquoise | turquoise | turquoise |
| TMEM119 | turquoise | turquoise | turquoise | turquoise | turquoise |
| NID2 | turquoise | turquoise | turquoise | turquoise | turquoise |
| MYH10 | turquoise | turquoise | turquoise | turquoise | turquoise |
| C11orf96 | turquoise | turquoise | turquoise | turquoise | turquoise |
| MOXD1 | turquoise | turquoise | turquoise | turquoise | turquoise |
| SGCD | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| SYT11 | turquoise | turquoise | turquoise | turquoise | turquoise |
| DPT | turquoise | turquoise | turquoise | turquoise | turquoise |
| COL14A1 | turquoise | turquoise | turquoise | turquoise | turquoise |
| UBE2QL1 | turquoise | turquoise | turquoise | turquoise | turquoise |
| PCDH7 | turquoise | turquoise | turquoise | turquoise | turquoise |
| PLXDC1 | turquoise | turquoise | turquoise | turquoise | turquoise |
| MLLT11 | turquoise | turquoise | turquoise | turquoise | turquoise |
| CLEC11A | turquoise | turquoise | turquoise | turquoise | turquoise |
| PPP1R18 | turquoise | gray | gray | turquoise | turquoise |
| PLEKHO1 | turquoise | gray | gray | turquoise | turquoise |
| EMP3 | turquoise | gray | gray | gray | turquoise |
| TSPAN4 | turquoise | gray | turquoise | turquoise | turquoise |
| FAM19A5 | turquoise | turquoise | turquoise | turquoise | turquoise |
| LBH | turquoise | turquoise | turquoise | turquoise | turquoise |
| PRKCDBP | turquoise | turquoise | turquoise | turquoise | turquoise |
| A2M | turquoise | turquoise | turquoise | turquoise | turquoise |
| COL8A2 | turquoise | turquoise | turquoise | turquoise | turquoise |
| IGFBP6 | turquoise | turquoise | turquoise | turquoise | turquoise |
| SLIT2 | turquoise | turquoise | turquoise | turquoise | turquoise |
| JAM2 | turquoise | turquoise | turquoise | turquoise | turquoise |
| PDLIM7 | turquoise | turquoise | turquoise | turquoise | turquoise |
| GJC1 | turquoise | turquoise | turquoise | turquoise | turquoise |
| MFAP5 | turquoise | turquoise | turquoise | turquoise | turquoise |
| CDK14 | turquoise | turquoise | turquoise | turquoise | turquoise |
| C3orf80 | turquoise | turquoise | turquoise | turquoise | turquoise |
| PHLDB2 | turquoise | turquoise | turquoise | turquoise | turquoise |
| SPG20 | turquoise | turquoise | turquoise | turquoise | turquoise |
| CYS1 | turquoise | turquoise | turquoise | turquoise | turquoise |
| TIE1 | turquoise | turquoise | turquoise | turquoise | turquoise |
| CHSY3 | turquoise | turquoise | turquoise | turquoise | turquoise |
| TNC | turquoise | turquoise | turquoise | turquoise | turquoise |
| PKD2 | turquoise | turquoise | turquoise | turquoise | turquoise |
| FAM129A | turquoise | gray | gray | turquoise | turquoise |
| NEXN | turquoise | turquoise | turquoise | turquoise | turquoise |
| GAS7 | turquoise | turquoise | turquoise | turquoise | turquoise |
| ECM2 | turquoise | turquoise | turquoise | turquoise | turquoise |
| CYR61 | turquoise | turquoise | turquoise | turquoise | turquoise |
| TCF4 | turquoise | turquoise | turquoise | turquoise | turquoise |
| HMCN1 | turquoise | turquoise | turquoise | turquoise | turquoise |
| PTGIS | turquoise | turquoise | turquoise | turquoise | turquoise |
| AKAP12 | turquoise | turquoise | turquoise | turquoise | turquoise |
| TMEM47 | turquoise | turquoise | turquoise | turquoise | turquoise |
| LDB2 | turquoise | turquoise | turquoise | turquoise | turquoise |
| CLMP | turquoise | turquoise | turquoise | turquoise | turquoise |
| MPDZ | turquoise | turquoise | turquoise | turquoise | turquoise |
| CRISPLD1 | turquoise | turquoise | turquoise | turquoise | turquoise |
| DZIP1 | turquoise | turquoise | turquoise | turquoise | turquoise |
| PRICKLE1 | turquoise | turquoise | turquoise | turquoise | turquoise |
| PRICKLE2 | turquoise | turquoise | turquoise | turquoise | turquoise |
| RECK | turquoise | turquoise | turquoise | turquoise | turquoise |
| MAP1B | turquoise | turquoise | turquoise | turquoise | turquoise |
| PPP1R3C | turquoise | turquoise | turquoise | turquoise | turquoise |
| TCEAL7 | turquoise | turquoise | turquoise | turquoise | turquoise |
| SYNM | turquoise | turquoise | turquoise | turquoise | turquoise |
| PDE1A | turquoise | turquoise | turquoise | turquoise | turquoise |
| PEG3 | turquoise | turquoise | turquoise | turquoise | turquoise |
| SYNPO2 | turquoise | turquoise | turquoise | turquoise | turquoise |
| FBLN5 | turquoise | turquoise | turquoise | turquoise | turquoise |
| NAP1L3 | turquoise | turquoise | turquoise | turquoise | turquoise |
| SYNC | turquoise | turquoise | turquoise | turquoise | turquoise |
| ARMCX1 | turquoise | turquoise | turquoise | turquoise | turquoise |
| SPARCL1 | turquoise | turquoise | turquoise | turquoise | turquoise |
| KCNMB1 | turquoise | turquoise | turquoise | turquoise | turquoise |
| CACNA2D1 | turquoise | turquoise | turquoise | turquoise | turquoise |
| C14orf132 | turquoise | turquoise | turquoise | turquoise | turquoise |
| MYH11 | turquoise | turquoise | turquoise | turquoise | turquoise |
| HSPB8 | turquoise | turquoise | turquoise | turquoise | turquoise |
| DES | turquoise | turquoise | turquoise | turquoise | turquoise |
| LMOD1 | turquoise | turquoise | turquoise | turquoise | turquoise |
| ACTG2 | turquoise | turquoise | turquoise | turquoise | turquoise |
| PLN | turquoise | turquoise | turquoise | turquoise | turquoise |
| MAB21L2 | turquoise | turquoise | turquoise | turquoise | turquoise |
| RUNX1T1 | turquoise | turquoise | turquoise | turquoise | turquoise |
| STON1 | turquoise | turquoise | turquoise | turquoise | turquoise |
| BOC | turquoise | turquoise | turquoise | turquoise | turquoise |
| KANK2 | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| FXYD6 | turquoise | turquoise | turquoise | turquoise | turquoise |
| C20orf194 | turquoise | turquoise | turquoise | turquoise | turquoise |
| PDLIM3 | turquoise | turquoise | turquoise | turquoise | turquoise |
| MGP | turquoise | turquoise | turquoise | turquoise | turquoise |
| AOC3 | turquoise | turquoise | turquoise | turquoise | turquoise |
| AMOTL1 | turquoise | turquoise | turquoise | turquoise | turquoise |
| TPM2 | turquoise | turquoise | turquoise | turquoise | turquoise |
| MRVI1 | turquoise | turquoise | turquoise | turquoise | turquoise |
| TSPYL5 | turquoise | turquoise | turquoise | turquoise | turquoise |
| FEZ1 | turquoise | turquoise | turquoise | turquoise | turquoise |
| CNRIP1 | turquoise | turquoise | turquoise | turquoise | turquoise |
| COX7A1 | turquoise | turquoise | turquoise | turquoise | turquoise |
| MRGPRF | turquoise | turquoise | turquoise | turquoise | turquoise |
| MYLK | turquoise | turquoise | turquoise | turquoise | turquoise |
| CNN1 | turquoise | turquoise | turquoise | turquoise | turquoise |
| CRYAB | turquoise | turquoise | turquoise | turquoise | turquoise |
| FILIP1L | turquoise | turquoise | turquoise | turquoise | turquoise |
| SYNDIG1 | turquoise | turquoise | turquoise | turquoise | turquoise |
| THBD | turquoise | turquoise | turquoise | turquoise | turquoise |
| MMP19 | turquoise | gray | turquoise | turquoise | turquoise |
| DLC1 | turquoise | turquoise | turquoise | turquoise | turquoise |
| WWTR1 | turquoise | turquoise | turquoise | turquoise | turquoise |
| FLNA | turquoise | turquoise | turquoise | turquoise | turquoise |
| CD93 | turquoise | turquoise | turquoise | turquoise | turquoise |
| MMP14 | turquoise | turquoise | turquoise | turquoise | turquoise |
| PRKD1 | turquoise | turquoise | turquoise | turquoise | turquoise |
| NDN | turquoise | turquoise | turquoise | turquoise | turquoise |
| MAGI2-AS3 | turquoise | turquoise | turquoise | turquoise | turquoise |
| COMP | turquoise | turquoise | turquoise | turquoise | turquoise |
| BASP1 | turquoise | gray | turquoise | gray | turquoise |
| SNAI2 | turquoise | turquoise | turquoise | turquoise | turquoise |
| RARRES2 | turquoise | turquoise | turquoise | turquoise | turquoise |
| CTGF | turquoise | turquoise | turquoise | turquoise | turquoise |
| AKT3 | turquoise | turquoise | turquoise | turquoise | turquoise |
| IL1R1 | turquoise | turquoise | turquoise | turquoise | turquoise |
| ST6GALNAC5 | turquoise | turquoise | turquoise | turquoise | turquoise |
| BICC1 | turquoise | turquoise | turquoise | turquoise | turquoise |
| KIRREL | turquoise | turquoise | turquoise | turquoise | turquoise |
| DOK5 | turquoise | turquoise | turquoise | turquoise | turquoise |
| MSN | turquoise | gray | gray | turquoise | turquoise |
| FAM101B | turquoise | turquoise | turquoise | turquoise | turquoise |
| LTBP2 | turquoise | turquoise | turquoise | turquoise | turquoise |
| FBLN2 | turquoise | turquoise | turquoise | turquoise | turquoise |
| LRRC15 | turquoise | turquoise | turquoise | turquoise | turquoise |
| LOX | turquoise | turquoise | turquoise | turquoise | turquoise |
| MFGE8 | turquoise | turquoise | turquoise | turquoise | turquoise |
| FAP | turquoise | turquoise | turquoise | turquoise | turquoise |
| COLEC12 | turquoise | turquoise | turquoise | turquoise | turquoise |
| FAM20C | turquoise | turquoise | turquoise | turquoise | turquoise |
| PTPRM | turquoise | turquoise | turquoise | turquoise | turquoise |
| BCAT1 | turquoise | turquoise | turquoise | turquoise | turquoise |
| MAF | turquoise | turquoise | turquoise | turquoise | turquoise |
| COL4A1 | turquoise | turquoise | turquoise | turquoise | turquoise |
| TUBA1A | turquoise | turquoise | turquoise | turquoise | turquoise |
| ENTPD1 | turquoise | turquoise | gray | turquoise | turquoise |
| DFNA5 | turquoise | turquoise | turquoise | turquoise | turquoise |
| FGFR1 | turquoise | turquoise | turquoise | turquoise | turquoise |
| S1PR3 | turquoise | turquoise | turquoise | turquoise | turquoise |
| VGLL3 | turquoise | turquoise | turquoise | turquoise | turquoise |
| ITGA5 | turquoise | turquoise | turquoise | turquoise | turquoise |
| PDPN | turquoise | turquoise | turquoise | turquoise | turquoise |
| GREM1 | turquoise | turquoise | turquoise | turquoise | turquoise |
| PMP22 | turquoise | turquoise | turquoise | turquoise | turquoise |
| COL18A1 | turquoise | turquoise | turquoise | turquoise | turquoise |
| PDGFC | turquoise | turquoise | turquoise | turquoise | turquoise |
| FN1 | turquoise | turquoise | turquoise | turquoise | turquoise |
| KCNE4 | turquoise | turquoise | turquoise | turquoise | turquoise |
| GLIS2 | turquoise | turquoise | turquoise | turquoise | turquoise |
| EFEMP1 | turquoise | turquoise | turquoise | turquoise | turquoise |
| ZNF521 | turquoise | turquoise | turquoise | turquoise | turquoise |
| CERCAM | turquoise | turquoise | turquoise | turquoise | turquoise |
| NOX4 | turquoise | turquoise | turquoise | turquoise | turquoise |
| NUAK1 | turquoise | turquoise | turquoise | turquoise | turquoise |
| COL15A1 | turquoise | turquoise | turquoise | turquoise | turquoise |
| CRISPLD2 | turquoise | turquoise | turquoise | turquoise | turquoise |
| LOXL1 | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| GFPT2 | turquoise | turquoise | turquoise | turquoise | turquoise |
| INHBA | turquoise | turquoise | turquoise | turquoise | turquoise |
| WISP1 | turquoise | turquoise | turquoise | turquoise | turquoise |
| DPYSL3 | turquoise | turquoise | turquoise | turquoise | turquoise |
| ZFPM2 | turquoise | turquoise | turquoise | turquoise | turquoise |
| PPAPDC1A | turquoise | turquoise | turquoise | turquoise | turquoise |
| MITF | turquoise | turquoise | turquoise | turquoise | turquoise |
| KIAA1462 | turquoise | turquoise | turquoise | turquoise | turquoise |
| OLFML1 | turquoise | turquoise | turquoise | turquoise | turquoise |
| FBLN1 | turquoise | turquoise | turquoise | turquoise | turquoise |
| PRRX1 | turquoise | turquoise | turquoise | turquoise | turquoise |
| MFAP2 | turquoise | turquoise | turquoise | turquoise | turquoise |
| TSHZ3 | turquoise | turquoise | turquoise | turquoise | turquoise |
| TWIST1 | turquoise | turquoise | turquoise | turquoise | turquoise |
| POSTN | turquoise | turquoise | turquoise | turquoise | turquoise |
| MRAS | turquoise | turquoise | turquoise | turquoise | turquoise |
| IGFBP7 | turquoise | turquoise | turquoise | turquoise | turquoise |
| TGFB1I1 | turquoise | turquoise | turquoise | turquoise | turquoise |
| NOTCH3 | turquoise | turquoise | turquoise | turquoise | turquoise |
| EFS | turquoise | turquoise | turquoise | turquoise | turquoise |
| BNC2 | turquoise | turquoise | turquoise | turquoise | turquoise |
| GUCY1A3 | turquoise | turquoise | turquoise | turquoise | turquoise |
| SFRP2 | turquoise | turquoise | turquoise | turquoise | turquoise |
| PXDN | turquoise | turquoise | turquoise | turquoise | turquoise |
| LUM | turquoise | turquoise | turquoise | turquoise | turquoise |
| COL4A2 | turquoise | turquoise | turquoise | turquoise | turquoise |
| RCN3 | turquoise | turquoise | turquoise | turquoise | turquoise |
| LOXL2 | turquoise | turquoise | turquoise | turquoise | turquoise |
| RFTN1 | turquoise | turquoise | turquoise | turquoise | turquoise |
| SERPING1 | turquoise | gray | gray | turquoise | turquoise |
| ASPN | turquoise | turquoise | turquoise | turquoise | turquoise |
| HOPX | turquoise | turquoise | turquoise | turquoise | turquoise |
| IGFBP5 | turquoise | turquoise | turquoise | turquoise | turquoise |
| CDH11 | turquoise | turquoise | turquoise | turquoise | turquoise |
| VEGFC | turquoise | turquoise | turquoise | turquoise | turquoise |
| GLT8D2 | turquoise | turquoise | turquoise | turquoise | turquoise |
| SFRP4 | turquoise | turquoise | turquoise | turquoise | turquoise |
| LAMA4 | turquoise | turquoise | turquoise | turquoise | turquoise |
| SDC2 | turquoise | turquoise | turquoise | turquoise | turquoise |
| CTSK | turquoise | turquoise | turquoise | turquoise | turquoise |
| NNMT | turquoise | turquoise | turquoise | turquoise | turquoise |
| COL10A1 | turquoise | turquoise | turquoise | turquoise | turquoise |
| GAS1 | turquoise | turquoise | turquoise | turquoise | turquoise |
| DKK3 | turquoise | turquoise | turquoise | turquoise | turquoise |
| CTHRC1 | turquoise | turquoise | turquoise | turquoise | turquoise |
| ADAM12 | turquoise | turquoise | turquoise | turquoise | turquoise |
| SERPINF1 | turquoise | turquoise | turquoise | turquoise | turquoise |
| TIMP3 | turquoise | turquoise | turquoise | turquoise | turquoise |
| AXL | turquoise | turquoise | turquoise | turquoise | turquoise |
| COL6A2 | turquoise | turquoise | turquoise | turquoise | turquoise |
| C1R | turquoise | turquoise | turquoise | turquoise | turquoise |
| EMILIN1 | turquoise | turquoise | turquoise | turquoise | turquoise |
| PTRF | turquoise | turquoise | turquoise | turquoise | turquoise |
| HTRA1 | turquoise | turquoise | turquoise | turquoise | turquoise |
| GUCY1B3 | turquoise | turquoise | turquoise | turquoise | turquoise |
| FIBIN | turquoise | turquoise | turquoise | turquoise | turquoise |
| LHFP | turquoise | turquoise | turquoise | turquoise | turquoise |
| MEIS1 | turquoise | turquoise | turquoise | turquoise | turquoise |
| LAYN | turquoise | turquoise | turquoise | turquoise | turquoise |
| CALD1 | turquoise | turquoise | turquoise | turquoise | turquoise |
| FERMT2 | turquoise | turquoise | turquoise | turquoise | turquoise |
| TNS1 | turquoise | turquoise | turquoise | turquoise | turquoise |
| MYL9 | turquoise | turquoise | turquoise | turquoise | turquoise |
| DDR2 | turquoise | turquoise | turquoise | turquoise | turquoise |
| TAGLN | turquoise | turquoise | turquoise | turquoise | turquoise |
| JAM3 | turquoise | turquoise | turquoise | turquoise | turquoise |
| ACTA2 | turquoise | turquoise | turquoise | turquoise | turquoise |
| MSRB3 | turquoise | turquoise | turquoise | turquoise | turquoise |
| C1S | turquoise | turquoise | turquoise | turquoise | turquoise |
| CCDC80 | turquoise | turquoise | turquoise | turquoise | turquoise |
| MXRA8 | turquoise | turquoise | turquoise | turquoise | turquoise |
| OSMR | turquoise | turquoise | turquoise | turquoise | turquoise |
| MXRA5 | turquoise | turquoise | turquoise | turquoise | turquoise |
| COL6A1 | turquoise | turquoise | turquoise | turquoise | turquoise |
| ISLR | turquoise | turquoise | turquoise | turquoise | turquoise |
| LGALS1 | turquoise | turquoise | turquoise | turquoise | turquoise |

TABLE 5-continued

Genes for identification of subtypes and sub-subtypes

| | CCMS | ccs | CRCA1 | CRCA2 | potential 1 |
|---|---|---|---|---|---|
| ADAMTS2 | turquoise | turquoise | turquoise | turquoise | turquoise |
| ANGPTL2 | turquoise | turquoise | turquoise | turquoise | turquoise |
| COL1A1 | turquoise | turquoise | turquoise | turquoise | turquoise |
| OLFML2B | turquoise | turquoise | turquoise | turquoise | turquoise |
| NTM | turquoise | turquoise | turquoise | turquoise | turquoise |
| COL11A1 | turquoise | turquoise | turquoise | turquoise | turquoise |
| FRMD6 | turquoise | turquoise | turquoise | turquoise | turquoise |
| MMP2 | turquoise | turquoise | turquoise | turquoise | turquoise |
| TUBB6 | turquoise | turquoise | turquoise | turquoise | turquoise |
| BGN | turquoise | turquoise | turquoise | turquoise | turquoise |
| MRC2 | turquoise | turquoise | turquoise | turquoise | turquoise |
| SPOCK1 | turquoise | turquoise | turquoise | turquoise | turquoise |
| ADAMTS12 | turquoise | turquoise | turquoise | turquoise | turquoise |
| PCOLCE | turquoise | turquoise | turquoise | turquoise | turquoise |
| COL8A1 | turquoise | turquoise | turquoise | turquoise | turquoise |
| FNDC1 | turquoise | turquoise | turquoise | turquoise | turquoise |
| SULF1 | turquoise | turquoise | turquoise | turquoise | turquoise |
| EFEMP2 | turquoise | turquoise | turquoise | turquoise | turquoise |
| PDGFRB | turquoise | turquoise | turquoise | turquoise | turquoise |
| AEBP1 | turquoise | turquoise | turquoise | turquoise | turquoise |
| THBS2 | turquoise | turquoise | turquoise | turquoise | turquoise |
| THY1 | turquoise | turquoise | turquoise | turquoise | turquoise |
| VIM | turquoise | turquoise | turquoise | turquoise | turquoise |
| VCAN | turquoise | turquoise | turquoise | turquoise | turquoise |
| FSTL1 | turquoise | turquoise | turquoise | turquoise | turquoise |
| COL12A1 | turquoise | turquoise | turquoise | turquoise | turquoise |
| ANTXR1 | turquoise | turquoise | turquoise | turquoise | turquoise |
| COL5A2 | turquoise | turquoise | turquoise | turquoise | turquoise |
| COL5A1 | turquoise | turquoise | turquoise | turquoise | turquoise |
| TIMP2 | turquoise | turquoise | turquoise | turquoise | turquoise |
| COL6A3 | turquoise | turquoise | turquoise | turquoise | turquoise |
| COL3A1 | turquoise | turquoise | turquoise | turquoise | turquoise |
| RAB31 | turquoise | turquoise | turquoise | turquoise | turquoise |
| SPARC | turquoise | turquoise | turquoise | turquoise | turquoise |
| COL1A2 | turquoise | turquoise | turquoise | turquoise | turquoise |
| FBN1 | turquoise | turquoise | turquoise | turquoise | turquoise |
| DCN | turquoise | turquoise | turquoise | turquoise | turquoise |
| GPC6 | turquoise | turquoise | turquoise | turquoise | turquoise |
| VASH2 | turquoise | turquoise | gray | turquoise | turquoise |
| CLDN11 | turquoise | turquoise | turquoise | turquoise | turquoise |
| SMCR8 | black | gray | black | gray | |
| C3orf67 | turquoise | gray | turquoise | gray | |
| NKX2-1 | turquoise | gray | gray | gray | |
| APBA1 | turquoise | gray | gray | gray | |
| TRDV3 | turquoise | gray | turquoise | gray | |
| FOXG1 | red | gray | gray | red | |
| TF | turquoise | gray | gray | turquoise | |
| KCNAB1 | turquoise | turquoise | gray | gray | |
| BAIAP2-AS1 | turquoise | turquoise | gray | gray | |
| SMPDL3B | red | gray | gray | red | |
| FIBCD1 | turquoise | gray | turquoise | gray | |
| HOXA6 | turquoise | turquoise | gray | gray | |
| AKR1C1 | turquoise | turquoise | gray | gray | |
| IL11 | turquoise | gray | gray | turquoise | |
| TMEM184A | yellow | yellow | yellow | gray | |
| NFASC | turquoise | gray | turquoise | gray | |
| TNFRSF10C | turquoise | gray | gray | gray | |
| KCNQ4 | turquoise | gray | turquoise | gray | |
| TFR2 | turquoise | gray | turquoise | gray | |

REFERENCES

Andre, T., C. Boni, et al, (2009). "Improved overall survival with oxaliplatin, fluorouracil, and leucovorin as adjuvant treatment in stage II or III colon cancer in the MOSAIC trial." *J Clin Oncol* 27(19): 3109-3116.

Cersosimo, R. J. (2005) "Oxaliplatin-associated neuropathy: a review." *Ann Pharmacother* 39(1): 128-135.

De Sousa, E. M. F. X. Wang, et al. (2013). "Poor-prognosis colon cancer is defined by a molecularly distinct subtype and develops from serrated precursor lesions." *Nat Med* 19(5): 614-618.

Isella, C., A. Terrasi, et al., (2015), "Stromal contribution to the colorectal cancer transcriptome." *Nat Genet* 47(4): 312-319.

Kuebler, J. P., H. S. Wieand, et al (2007). "Oxaliplatin combined with weekly bolus fluorouracil and leucovorin as surgical adjuvant chemotherapy for stage II and III colon cancer: results from NSABP C-07." *J Clin Oncol* 25(16): 2198-2204.

Marisa, L., A. de Reynies, et al. (2013). "Gene expression classification of colon cancer into molecular subtypes: characterization, validation, and prognostic value." *PLoS Med* 10(5): e1001453.

Sadanandam, A., C. A. Lyssiotis, et al. (2013): "A colorectal cancer classification system that associates cellular phenotype and responses to therapy." *Nat Med* 19(5): 619-625.

Tournigand, C., T. Andre. et al. (2012). "Adjuvant therapy with fluorouracil and oxaliplatin in stage II and elderly patients (between ages 70 and 75 years) with colon cancer subgroup analyses of the Multicenter International Study of Oxaliplatin, Fluorouracil, and Leucovorin in the Adjuvant Treatment of Colon Cancer trial." *J Clinc Oncol* 30(27): 3353-3360.

The invention claimed is:

1. A method of treating stage III colon cancer patients comprising:
   a) obtaining a colon cancer tumor tissue sample from a patient with stage III colon cancer,
   b) contacting a genetic sample from said colon cancer tumor tissue sample with a plurality of specific genetic sequence binding targets and measuring the expression level of a panel of 72 genes, wherein the 72 genes are AKAP12, ANKRD44, BGN, BHLHE41, BMP7 C8orf84, CAB39L, CDKN2B, CKMT2, COL11A1, COMP, CPE, CSGALNACT1, CXCL10, CXCL11, CXCL13, CXCL2, CXCL9, CYP1B1, DAPK1, DCBLD2, DPEP1, EPB41L4B, ERAP2, F5, FAP, FGL2, FN1, FNDC1, GBP1, GBP4, GPX3, GRM8, GZMB, HGD, HOXA13, HSD17B2, ID4, IDO1, IL8, INHBA, MFAP5, MGP, MMP11, MMP28, NFIB, OAS2, PAPPA, PIGR, PLA2G12B, POU2AF1, PRAP1, PROM2, PSMB9, PTPRC, ROBO1, SDC2, SELL, SERPINE1, SFRP2, SGK2, SLC4A4, SPARC, SPP1, SSPN, STC1, TACSTD2, TGFBR3, TM4SF1, TYMS, VCAN, and VNN1,
   c) obtaining a gene expression signature for said colon cancer tumor tissue from the gene expression level of the panel of 72 genes in b),
   d) identifying said colon cancer tumor tissue as being a subtype responsive to oxaliplatin, and
   e) administering oxaliplatin in combination with 5'fluorouracil and leucovorin (FULV) to said patient with Stage III colon cancer in a).

2. The method of claim 1, wherein the genetic sample comprises cDNA or RNA either in purified form or as a tissue lysate.

3. The method of claim 1, wherein the identified tumor tissue subtype is of the enterocyte tissue type.

4. A method for treating colon cancer in a patient with Stage III colon cancer comprising:
   a) obtaining a colon cancer tumor tissue sample from a patient with stage III colon cancer,
   b) isolating RNA or producing a lysate from the colon cancer tumor tissue sample,
   c) contacting said RNA or said lysate with a plurality of sequence specific probes capable of determining the level of expression of a panel of 72 genes, wherein the panel of 72 genes are AKAP12, ANKRD44, BGN, BHLHE41, BMP7 C8orf84, CAB39L, CDKN2B, CKMT2, COL11A1, COMP, CPE, CSGALNACT1, CXCL10, CXCL11, CXCL13, CXCL2, CXCL9, CYP1B1, DAPK1, DCBLD2, DPEP1, EPB41L4B, ERAP2, F5, FAP, FGL2, FN1, FNDC1, GBP1, GBP4, GPX3, GRM8, GZMB, HGD, HOXA13, HSD17B2, ID4, IDO1, IL8, INHBA, MFAP5, MGP, MMP11, MMP28, NFIB, OAS2, PAPPA, PIGR, PLA2G12B, POU2AF1, PRAP1, PROM2, PSMB9, PTPRC, ROBO1, SDC2, SELL, SERPINE1, SFRP2, SGK2, SLC4A4, SPARC, SPP1, SSPN, STC1, TACSTD2, TGFBR3, TM4SF1, TYMS, VCAN, and VNN1,
   d) measuring the gene expression level of the panel of 72 genes and obtaining a gene expression signature for said colon cancer tumor tissue from the gene expression level of said genes in c),
   e) identifying said colon cancer tumor tissue as being a subtype responsive to oxaliplatin, and
   f) administering oxaliplatin to said patient with Stage III colon cancer in a).

5. The method of claim 4, wherein the oxaliplatin in administered in combination with 5'fluorouracil and leucovorin (FULV).

6. The method of claim 4, wherein the colon cancer tumor tissue sample is a subtype of the enterocyte tissue type.

* * * * *